(12) United States Patent
Kong et al.

(10) Patent No.: US 6,617,346 B1
(45) Date of Patent: Sep. 9, 2003

(54) CIS-IMIDAZOLINES

(75) Inventors: Norman Kong, West Caldwell, NJ (US); Emily Aijun Liu, Nutley, NJ (US); Binh Thanh Vu, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/316,696

(22) Filed: Dec. 11, 2002

Related U.S. Application Data

(60) Provisional application No. 60/341,729, filed on Dec. 18, 2001, and provisional application No. 60/390,876, filed on Jun. 21, 2002.

(51) Int. Cl.[7] .................... A61K 31/415; C07D 233/06
(52) U.S. Cl. .................... 514/399; 514/400; 548/354.1
(58) Field of Search ................ 514/399, 400; 548/354.1

(56) References Cited

FOREIGN PATENT DOCUMENTS

| EP | 0 363 061 | 4/1990 |
|----|-----------|--------|
| WO | WO 92/03421 | 3/1992 |
| WO | WO 0078725 | 12/2000 |

OTHER PUBLICATIONS

Hunter, et al, 1972, Canadian Journal of Chemistry, 50, 669–677.*
Karaman, et al, 1973, Croatia Chemica Acta, 45, 519–522.*
Claudi et al., J. Med. Chem., 43, pp. 599–608 (2000).
Wells et al., J. Org. Chem., 37, pp. 2158–2161 (1972).
Harris et al., J. Org. Chem., 64, pp. 6019–6022 (1999).
Wells et al., Tetrahedron Letters, 37, pp. 6439–6442 (1996).
Hammouda et al., Egypt. J. Chem., 30, pp. 239–247 (1987).
Hunter, Duncan Harvey, et al., Canadian Journal of Chemistry, 50(5), pp. 669–677 (1972).
Karaman, B., et al., Chemical Abstracts, vol. 80, No. 11, p. 354 (1974).
Goerlitzer, K., et al., Pharmazie, 54(1), pp. 35–41 (1999).

* cited by examiner

*Primary Examiner*—Joseph K. McKane
*Assistant Examiner*—Andrea D. Small
(74) *Attorney, Agent, or Firm*—George W. Johnston; Patricia S. Rocha-Tramaloni; Bernard Lau

(57) ABSTRACT

The present invention provides compounds according to formula I and formula II and pharmaceutically acceptable salts and esters thereof, having the designations provided herein and which inhibit the interaction of MDM2 protein with a p53-like peptide and have antiproliferative activity

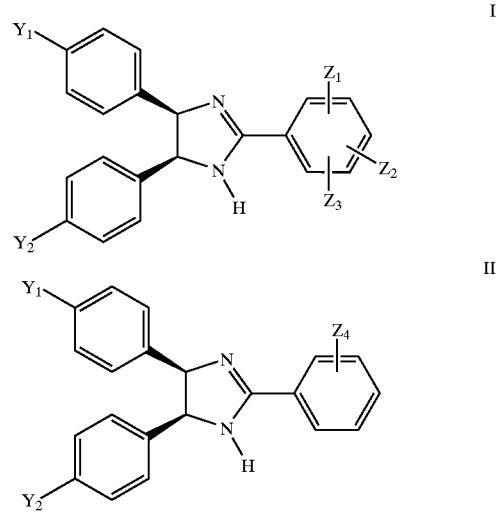

11 Claims, No Drawings

CIS-IMIDAZOLINES

This application claims priority under 35 U.S.C. §119(e) of provisional applications Ser. No. 60/341,729, filed Dec. 18, 2001 and Ser. No. 60/390,876, filed Jun. 21, 2002.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination.with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Wells et al. *J. Org. Chem.*, 1972, 37, 2158–2161, report synthesis of imidazolines. Hunter et al. *Can. J. Chem.*, 1972, Vol. 50, 669–77, report the preparation of amarine and isoamarine compounds which had previously been studied for chemiluminescence (McCapra et al. *Photochem. and Photobiol.* 1965, 4, 1111–1121). Zupanc et al. *Bull. Soc. Chem. & Tech.* (Yugoslavia) 1980–81, 27/28, 71–80, report the use of triaryl imidazolines as starting materials in the preparation of EDTA derivatives. EP 363 061 to Matsumoto reports imidazoline derivaties useful as immunomodulators. The compounds were indicated to have low toxicity. Treatment and/or prevention of rheumatoid arthritis, multiple sclerosis, systemic lupus, erythemathodes, and rheumatic fever were implicated. WO 00/78725 to Choueiry et al. report a method for making substituted amidine compounds, and indicate that imidazoline-type compounds may be useful in the treatment of diabetes or related diseases involving impaired glucose disposal.

SUMMARY OF THE INVENTION

The present invention provides at least one compound selected from a compound of formula I

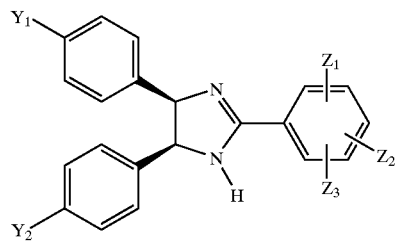

and the pharmaceutically acceptable salts and esters thereof, wherein $Z_1$, $Z_2$ and $Z_3$ are each independently selected from lower alkoxy, —$CH_2OCH_3$, and —$CH_2OCH_2CH_3$, or one of $Z_1$, $Z_2$ or $Z_3$ is —H and the other two are each independently selected from lower alkyl, lower alkoxy, —Cl, —Br, —F, —$CF_3$, —$CH_2OCH_3$, —$CH_2OCH_2CH_3$, —$OCH_2CH_2R_1$, —$CH_2$-morpholino, —$OR_2$, —$CH_2R_2$, —$OCH_2CF_3$, —$OCH(CH_3)CH_2OH$ and —COOQ, wherein Q is selected from —H and lower alkyl, or one of $Z_1$, $Z_2$ or $Z_3$ is —H and the other two taken together with the two carbon atoms and the bonds between them from the benzene ring to which they are substituted form a ring selected from 5- and 6-membered unsaturated rings, and 5- and 6-membered saturated rings that contain at least one hetero atom selected from S, N, and O, wherein $R_1$ is selected from —F, —$OCH_3$, —$N(CH_3)_2$, and unsaturated 5-membered rings containing at least one hetero atom wherein the hetero atom is selected from S, N and O, wherein $R_2$ is a 3- to 6-membered saturated ring, and $Y_1$ and $Y_2$ are each independently selected from —Cl, —Br, —$NO_2$, —C≡N and C≡CH.

The present invention also provides at least one compound selected from a compound of formula II

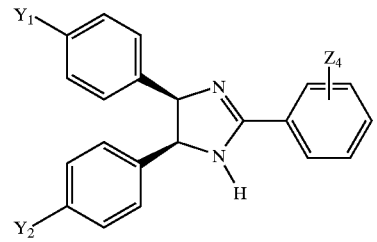

and the pharmaceutically acceptable salts and esters thereof, wherein $Z_4$ is selected from C1–C2 alkyl, lower alkoxy, —OH, —$SCH_3$, —$CF_3$, —$NO_2$, —$COOQ_2$, —$N(CH_3)_2$, —$OCH_2$-phenyl, —Cl, —Br, —F, —$OCH_2C$=$OOQ_1$, saturated 5- and 6-membered rings containing at least one hetero atom wherein the hetero atom is selected from S, N and O, wherein $Q_1$ is selected from —H, —$NH_2$, and lower alkyl, wherein $Q_2$ is selected from —H and lower alkyl, $Y_1$ and $Y_2$ are independently selected from —Cl, —Br, —$NO_2$ and —CN with the proviso that where $Y_1$ and $Y_2$ are both —Cl, then $Z_4$ is not —Cl, with the proviso that where $Y_1$ and $Y_2$ are both —$NO_2$, then $Z_4$ is not —$NO_2$, and with the proviso that where $Y_1$ and $Y_2$ are both —CN, then $Z_4$ is not —CN.

DETAILED DESCRIPTION OF THE INVENTION

The present invention provides cis-imidazolines which are small molecule inhibitors of the MDM2-p53 interaction. In cell-free and cell-based assays, compounds of the present invention are shown to inhibit the interaction of MDM2 protein with a p53-like peptide with a potency that is approximately 100 fold greater than a p53-derived peptide. In cell-based assays, these compounds have demonstrated mechanistic activity. Incubation of cancer cells with wild-type p53 has led to accumulation of p53 protein, induction of p53-regulated p21 gene, and cell cycle arrest in G1 and G2 phase. This resulted in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

The present invention provides at least one compound selected from a compound of formula I

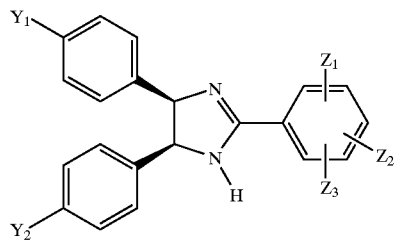

I and the pharmaceutically acceptable salts and esters thereof, wherein $Z_1$, $Z_2$ and $Z_3$ are each independently selected from lower alkoxy, —$CH_2OCH_3$, and —$CH_2OCH_2CH_3$, or one of $Z_1$, $Z_2$ or $Z_3$ is —H and the other two are each independently selected from lower alkyl, lower alkoxy, —Cl, —Br, —F, —$CF_3$, —$CH_2OCH_3$, —$CH_2OCH_2CH_3$, —$OCH_2CH_2R_1$, —$CH_2$-morpholino, —$OR_2$, —$CH_2R_2$, —$OCH_2CF_3$, —$OCH(CH_3)CH_2OH$ and —COOQ, wherein Q is selected from —H and lower alkyl, or one of $Z_1$, $Z_2$ or $Z_3$ is —H and the other two taken together with the two carbon atoms and the bonds between them from the benzene ring to which they are substituted form a ring selected from 5- and 6-membered unsaturated rings, and 5- and 6-membered saturated rings that contain at least one hetero atom selected from S, N, and O, wherein $R_1$ is selected from —F, —$OCH_3$, —$N(CH_3)_2$, and unsaturated 5-membered rings containing at least one hetero atom wherein the hetero atom is selected from S, N and O, wherein $R_2$ is a 3- to 6-membered saturated ring, and $Y_1$ and $Y_2$ are each independently selected from —Cl, —Br, —$NO_2$ and —C≡N and —C≡CH.

The present invention also provides at least one compound selected from a compound of formula II

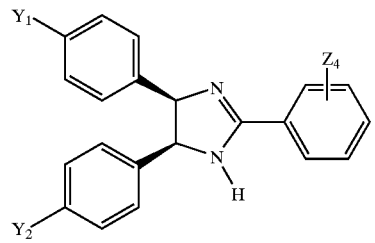

II and the pharmaceutically acceptable salts and esters thereof, wherein $Z_4$ is selected from C1–C2 alkyl, lower alkoxy, —OH, —$SCH_3$, —$CF_3$, —$NO_2$, —$COOQ_2$, —$N(CH_3)_2$, —$OCH_2$-phenyl, —Cl, —Br, —F, —$OCH_2C$=$OOQ_1$, saturated 5- and 6-membered rings containing at least one hetero atom wherein the hetero atom is selected from S, N and O, wherein $Q_1$ is selected from —H, —$NH_2$, and lower alkyl, wherein $Q_2$ is selected from —H and lower alkyl, $Y_1$ and $Y_2$ are independently selected from —Cl, —Br, —$NO_2$, —C≡N and —C≡CH.

with the proviso that where $Y_1$ and $Y_2$ are both —Cl, then $Z_4$ is not —Cl, with the proviso that where $Y_1$ and $Y_2$ are both —$NO_2$, then $Z_4$ is not —$NO_2$, and with the proviso that where $Y_1$ and $Y_2$ are both —CN, then $Z_4$ is not —CN.

"Effective amount" means an amount that is effective to prevent, alleviate or ameliorate symptoms of disease or prolong the survival of the subject being treated.

"Halogen" means fluorine, chlorine, bromine or iodine.

"Hetero atom" means an atom selected from N, O and S.

"$IC_{50}$" refers to the concentration of a particular compound required to inhibit 50% of a specific measured activity. $IC_{50}$ can be measured, inter alia, as is described subsequently.

"Alkyl" denotes a straight-chained or branched saturated aliphatic hydrocarbon. "Lower alkyl" groups denote C1–C6 alkyl groups and include methyl, ethyl, propyl, isopropyl, butyl, t-butyl, 2-butyl, pentyl, hexyl, and the like. Generally, lower alkyl is preferably C1–C4 alkyl, and more preferably C1–C3 alkyl.

"Alkoxy" denotes —O-alkyl. "Lower alkoxy" denotes —O-lower alkyl.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., Textbook of Drug Design and Development (2d Ed. 1996) at pp. 152–191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

"Therapeutically effective amount" means an amount of at least one compound of the present invention, that significantly inhibits proliferation and/or prevents differentiation of a human tumor cell, including human tumor cell lines.

Compounds of the present invention as exemplified advantageously show IC50s from about 0.5 $\mu$M to about 300 $\mu$M.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The compounds of the present invention can be prepared according to the following schemes. The following definitions are provided as applicable to the synthesis schemes:

$V^1$, $V^2$, $V^3$, $V^4$, $V^5$ are each independently selected from the group of:
hydrogen,
—$OV^6$,
—$SV^7$,
—$NV^8V^9$,
—$CONV^8V^9$,
—$COOV^{10}$
halogen,
nitro,
trifluoromethyl,
lower alkyl, which optionally may be substituted by $V^{11}$, and
cycloalkyl;

$V^1$, $V^2$ together may form part of a heterocycle with one or more hetereoatoms, which optionally may be substituted by $V^{10}$.

$V^2$, $V^3$ together may form part of a heterocycle with one or more hetereoatoms, which optionally may be substituted by $V^{10}$.

$Y^1$, $Y^2$ are each independently selected from the group of:
—Cl,
—Br,
nitro,
cyano, and
—C≡CH;

$V^6$ is selected from the group of:
hydrogen,
lower alkyl, which optionally may be substituted by $V^{11}$, and
cycloalkyl;

$V^7$ is selected from the group of:
hydrogen, and
lower alkyl;

$V^8$, $V^9$ are each independently selected from the group of:
hydrogen,
lower alkyl,
cycloalkyl; or $V^8$, $V^9$ together may form part of a hetereocycle with one or more hetereoatoms;

$V^{10}$ is selected from the group of:
hydrogen,
lower alkyl, and
cycloalkyl;

$V^{11}$ is selected from the group of:
—$CONV^8V^9$
—$NV^8V^9$,
—$COOV^{10}$,
aryl,
halogen,
lower alkoxy,
morpholinyl, and
5-membered heterocycles;

The cis isomers of formula I are preferred.

Scheme I

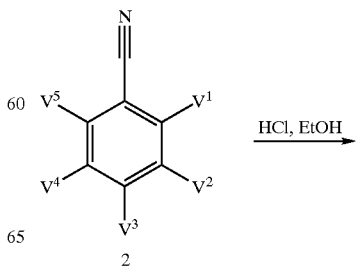

2

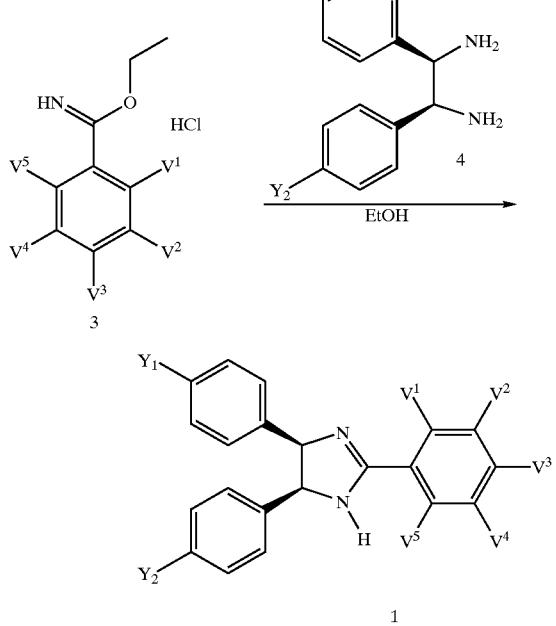

Many benzonitriles of formula 2 are commercially available. They are converted to the imidate salts (3) using HCl gas in ethanol. The rate of the reaction depends on the substituents on the phenyl ring. In cases where $V^1 \neq H$, it may be necessary to run the reaction under pressure of HCl over a longer period of time. Condensation of the imidates (3) with the 1,2-diamines (4) is carried out in ethanol at 40–100° C. in the presence or absence of a base such as triethylamine.

The meso-1,2-diamines of formula 4 ($Y^1 = Y^2$) are known compounds and prepared according to the literature procedures (see Jennerwein, M. et al. *Cancer Res. Clin. Oncol.* 1988, 114, 347–58; Vogtle, F.; Goldschmitt, E. *Chem. Ber.* 1976, 109, 1–40).

If it is desired to prepare the 1,2-diamines of formula 4 wherein $Y^1 \neq Y^2$, modifications to the existing procedures (vide supra) can be made. An equal molar mixture of the benzaldehydes and meso-1,2-bis-(2-hydroxy-phenyl)-ethane-1,2-diamine can be used to afford a mixture of 1,2-diamines (Scheme II). It was then reacted with compound of formula 3 to give a mixture of products. The desired compound (1) can be isolated from the mixture by preparative chromatography techniques.

Scheme II

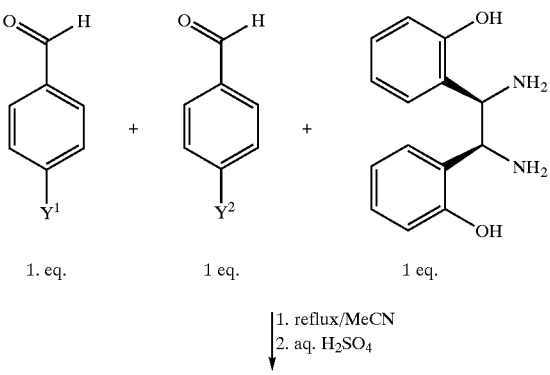

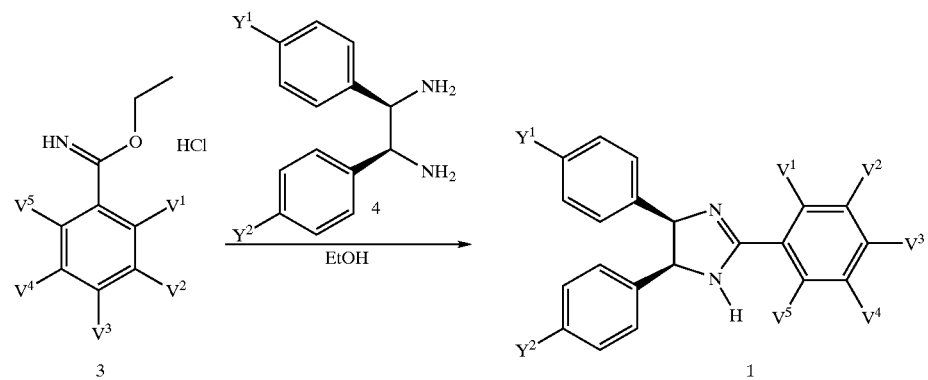

The imidate salts (6) can be prepared from the amides of formula 5 using triethyloxonium tetrafluoroborate in methylene chloride (Scheme III), a method known in the art (Weintraub, L.; Oles, S. R.; Kalish, N. *J. Org. Chem.* 1968, 33, 1679–1681). The imidate salts (6) are then condensed with the diamines (4) in the same manner as described for the imidates (3).

Scheme III

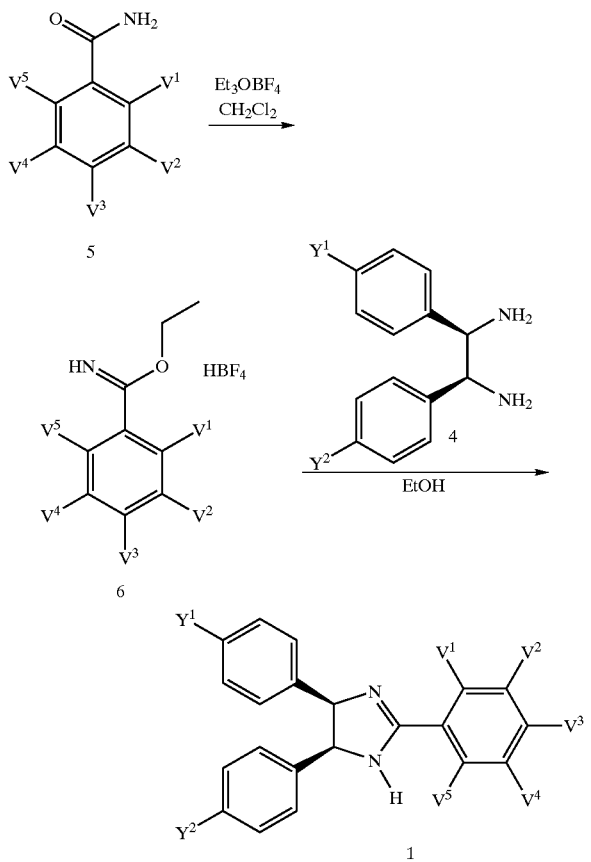

The compounds of formula 1 can be prepared directly by a condensation reaction of the benzoic acids (7) with the 1,2-diamines (4) (Scheme IV). The yields are low and thus it can be useful in cases where methods of preparation of imidates (3 and 4) have failed (see Hammouda, H. A.; Abd-Allah, S. O.; Sharaf, M. A. F. *Egypt. J. Chem.* 1987, 30, 239–247).

Scheme IV

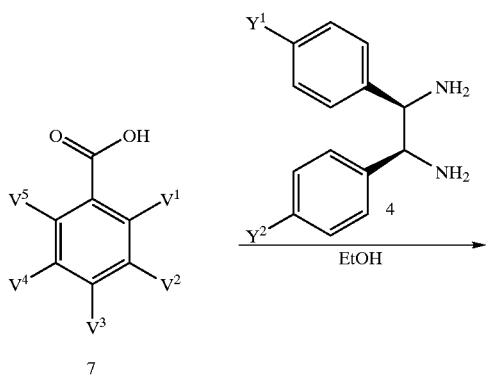

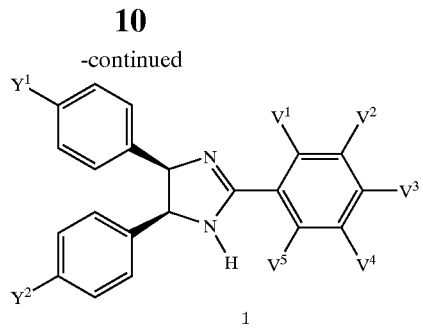

Benzonitriles of formula 2 (of Scheme I) may be prepared in accordance with the following methods.

The benzonitriles of formula 9 (V can be any suitable group such as for $V^1$, $V^2$, $V^3$, $V^4$, or $V^5$) can be prepared by alkylation of phenols 8 with $V^6X$ (X=Cl, Br, I) using conventional methods (Scheme V). The phenoxide anion is generated by a base such as cesium carbonate or potassium carbonate. The reaction typically runs at reflux temperature of a solvent such as ethanol. $V^6$ can also be introduced using Mitsunobu reaction (see for example, Hughes, D. L. *Org. React.* 1992, 42, 335–656).

Scheme V

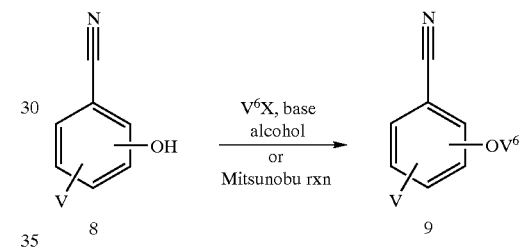

Aromatic aldehydes 10 (V can be any suitable group such as for $V^1$, $V^2$, $V^3$, $V^4$, or V5) can be converted into benzonitriles using literature procedures (Karmarkar, S. N; Kelkar, S. L.; Wadia, M. S. *Synthesis* 1985, 510–512; Bergeron, R. J. et al. *J. Med. Chem.* 1999, 42, 95–108). $V^6$ group can then be introduced using $V^6X$ (X=Cl, Br, I) or Mitsunobu reaction to give the benzonitriles 11 (Scheme VI).

Scheme VI

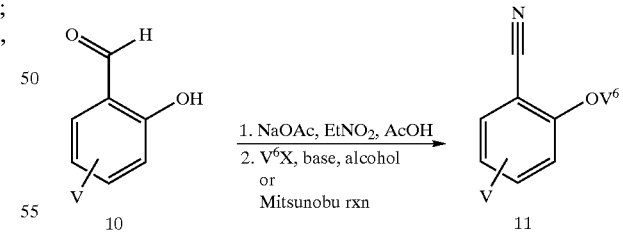

The halides of formula 13 can be prepared by bromination or iodination of phenols (12) (Scheme VII, V can be any suitable group such as for $V^1$, $V^2$, $V^3$, $V^4$, or $V^5$). Reaction conditions such as N-bromosuccinimide/tetrahydrofuran or iodine/thallium acetate can be utilized (see for example, Carreno, M. C.; Garcia Ruano, J. L.; Sanz, G.; Toledo, M. A.; Urbano, A. *Synlett* 1997, 1241–1242; Cambie, R. C.; Rutledge, P. S.; Smith-Palmer, T.; Woodgate, P. D. *J. Chem. Soc., Perkin Trans.* 1 1976, 1161–4). $V^6$ group can then be introduced using $V^6X$ (X=Cl, Br, I) or Mitsunobu reaction.

Methods of converting aromatic halides to the corresponding nitrites are known in the art (see for example, Okano, T.; Iwahara, M.; Kiji, J., *Synlett* 1998, 243). Cyanation of halides 13 (X'=Br, I) is accomplished using zinc cyanide with a catalyst such as tetrakis(triphenyl-phosphine) palladium. Solvents such dimethylformamide can be used and the reaction temperature is between 80–110° C.

Scheme VII

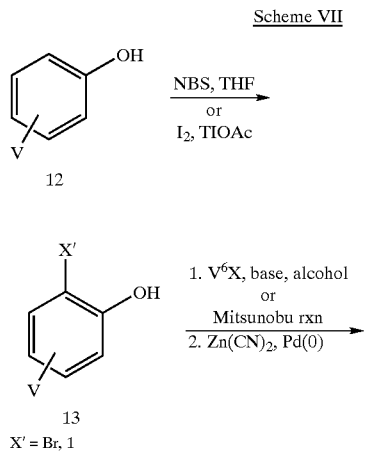

In Scheme VIII, amination of aromatic halides using $HNV^8V^9$ and palladium catalyst can be utilized to provide the benzonitriles of formula 15 (see for example, Harris, M. C.; Geis, O.; Buchwald, S. L. *J. Org. Chem.* 1999, 64, 6019).

Scheme VIII

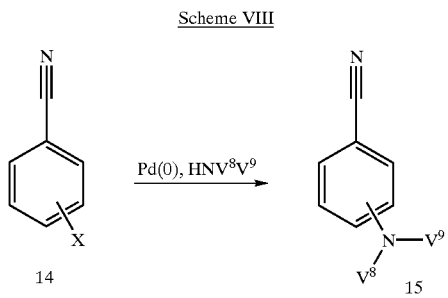

Various benzonitriles of formula 11 (V can be any suitable group such as $V^1$, $V^2$, $V^3$, $V^4$, or $V^5$) can be prepared by nucleophilic substitution of benzonitriles (16) (Scheme 9). Procedures to affect that transformation are reported in the literature (see for example, X=F: Wells, K. M.; Shi, Y.-J.; Lynch, J. E.; Humphrey, G. R.; Volante, R. P.; Reider, P. J. *Tetrahedron Lett.* 1996, 37, 6439–6442; X=NO$_2$: Harrison, C. R.; Lett, R. M.; McCann, S. F.; Shapiro, R.; Stevenson, T. M. WO 92/03421, 1992).

Scheme IX

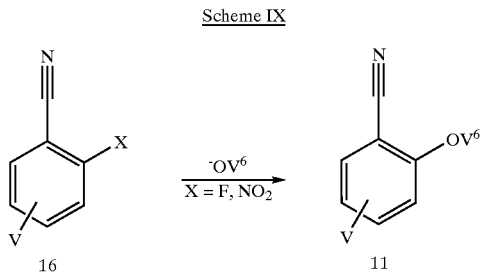

Methyl ester of 5-bromoisophthalic acid can be utilized to prepare a variety of 3,5-disubstituted benzonitriles (18) wherein $W=-CH_2OV^6$, $-CH_2NV^8V^9$, $-CH_2$-(morpholine), $-CONV^8V^9$, $-COOV^{10}$ (Scheme X). Suitable functional group transformations (FGT) can convert the ester moiety to various other groups (e.g. carboxylic acid, amide, alcohol, halide, ether, amine, etc.), as is known in the art.

Scheme X

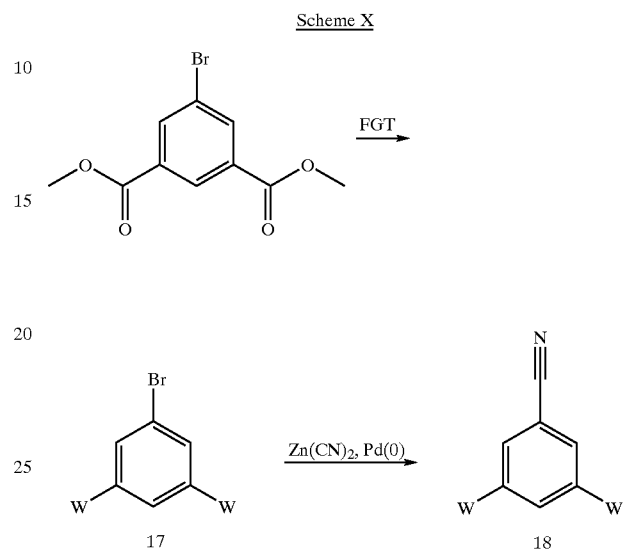

To prepare benzonitriles of formula 21 wherein $V^1$, $V^2$, $V^3$, $V^4$, or $V^5$=$OV^6$, sequential alkylation of the diols (19) with suitable $V^6X$ (X=Cl, Br, I) are used. The bromides (20) are then converted to the nitrites (21) using zinc cyanide and Pd(0) catalyst (Scheme XI).

Scheme XI

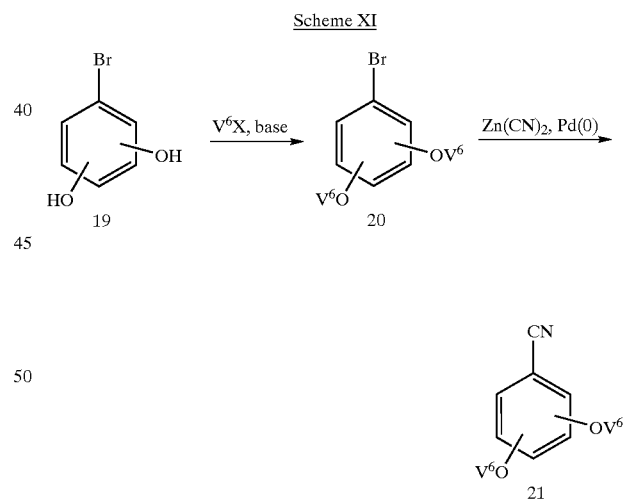

Method of preparation of 3-bromo-5-methoxy-phenyl-methanol from 3-bromo-5-methyl-phenol (see Claudi, F. et al. *J. Med. Chem.* 2000, 43, 599–608) can be adapted to provide various benzonitriles of formula 24 (Scheme XII). The phenols 22 can be alkylated with $V^6X$ (X=Cl, Br, I). Oxidation of methyl group using potassium permanganate provides the carboxylic acid (23). Manipulation of the carboxylic acid moiety leads to various other groups such as amide, alcohol, halide, ether, amine, etc. The bromides are then converted into nitrites (24) using zinc cyanide and Pd(0) catalyst.

Scheme XII

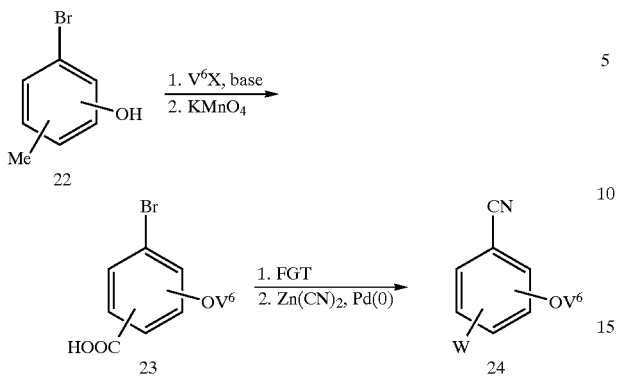

The present invention encompasses the following Examples. Structural formulas follow. With regard to structural formulas, it is understood that oxygen and nitrogen atoms with available electrons have a hydrogen bound thereto, as indicated by compound name.

EXAMPLE 1

4,5-bis-(4-Chloro-phenyl)-2-(2-methoxy-phenyl)-4,5-dihydro-1H-imidazole

Hydrogen chloride gas was passed through a solution of 2-methoxy-benzonitrile (760 mg, 5.708 mmol) in anhydrous ethanol (125 mL) cooled to 0° C. After 3.5 h, hydrogen chloride gas was stopped and the reaction mixture was stirred at room temperature overnight. The solvent was removed and the residue was triturated in diethyl ether to afford ethyl 2-methoxy-benzimidate hydrochloride (865 mg, 70%). It was used without further purification.

A solution of meso-1,2-bis-(4-chloro-phenyl)-ethane-1,2-diamine (50 mg, 0.178 mmol, prepared according to the procedure described by Jennerwein, M. et al. *Cancer Res. Clin. Oncol.* 1988, 114, 347–58; Vogtle, F.; Goldschmitt, E. *Chem. Ber.* 1976, 109, 1–40) and ethyl 2-methoxy-benzimidate hydrochloride (38.4 mg, 0.178 mmol) in ethanol (5 mL) was heated at reflux for 18 h. The solvent was removed, and the residue was taken in methylene chloride (10 mL). The reaction mixture was washed with sodium bicarbonate solution (1 mL) and dried over anhydrous sodium sulfate. The solid was then filtered off, and the filtrate was concentrated in vacuo. Purification of the crude residue by flash chromatography (Biotage system, KP-Sil™ 32–63 μm, 60 Å silica gel) eluting with 1% methanol in methylene chloride yielded 4,5-bis-(4-chloro-phenyl)-2-(2-methoxy-phenyl)-4,5-dihydro-1H-imidazole (59 mg, 84%). HR-MS (ES, m/z) calculated for $C_{22}H_{19}N_2OCl_2$ [(M+H)$^+$] 397.0870, observed 397.0870.

EXAMPLE 2

In an analogous manner as described in Example 1, there were obtained:

a. 4,5-Bis-(4-chloro-phenyl)-2-(2-methylsulfanyl-phenyl)-4,5-dihydro-1H-imidazole from meso-1,2-bis-(4-chloro-phenyl)-ethane-1,2-diamine and 2-methylsulfanyl-benzonitrile. HR-MS (EI, m/z) calculated for $C_{22}H_{16}N_2SCl_2$ [(M−2H)$^+$] 410.0411, observed 410.0423.

b. 2-[4,5-Bis-(4-chloro-phenyl)-4,5-dihydro-1H-imidazol-2-yl]-phenol from meso-1,2-bis-(4-chloro-phenyl)-ethane-1,2-diamine and 2-hydroxy-benzonitrile. HR-MS (EI, m/z) calculated for $C_{21}H_{14}N_2OCl_2$ [(M−2H)$^+$] 380.0483, observed 380.0481.

c. 4,5-Bis-(4-chloro-phenyl)-2-(2-fluoro-phenyl)-4,5-dihydro-1H-imidazole from meso-1,2-bis-(4-chloro-phenyl)-ethane-1,2-diamine and 2-fluoro-benzonitrile. HR-MS (EI, m/z) calculated for $C_{21}H_{15}N_2Cl_2F$ (M$^+$) 384.0596, observed 384.0591.

d. 2-(2-Chloro-phenyl)-4,5-bis-(4-chloro-phenyl)-4,5-dihydro-1H-imidazole from meso-1,2-bis-(4-chloro-phenyl)-ethane-1,2-diamine and 2-chloro-benzonitrile. HR-MS (ES, m/z) calculated for $C_{21}H_{16}N_2Cl_3$ [(M+H)$^+$] 401.0375, observed 401.0377.

e. 3-[4,5-Bis-(4-chloro-phenyl)-4,5-dihydro-1H-imidazol-2-yl]-phenol from meso-1,2-bis-(4-chloro-phenyl)-ethane-1,2-diamine and 3-hydroxy-benzonitrile. HR-MS (EI, m/z) calculated for $C_{21}H_{16}N_2OCl_2$ (M$^+$) 382.0640, observed 382.0631.

f. 3-[4,5-Bis-(4-chloro-phenyl)-4,5-dihydro-1H-imidazol-2-yl]-benzoic acid ethyl ester from meso-1,2-bis-(4-chloro-phenyl)-ethane-1,2-diamine and 3-cyano-benzoic acid. HR-MS (EI, m/z) calculated for $C_{24}H_{20}N_2O_2Cl_2$ (M$^+$) 438.0902, observed 438.0901.

g. 4,5-Bis-(4-chloro-phenyl)-2-(3-fluoro-phenyl)-4,5-dihydro-1H-imidazole from meso-1,2-bis-(4-chloro-phenyl)-ethane-1,2-diamine and 3-fluoro-benzonitrile. HR-MS (EI, m/z) calculated for $C_{21}H_{15}N_2Cl_2$ F (M$^+$) 384.0596, observed 384.0588.

h. 4,5-Bis-(4-chloro-phenyl)-2-(3-methoxy-phenyl)-4,5-dihydro-1H-imidazole from meso-1,2-bis-(4-chloro-phenyl)-ethane-1,2-diamine and 3-methoxy-benzonitrile. HR-MS (ES, m/z) calculated for $C_{22}H_{18}N_2OCl_2$ (M$^+$) 396.0789, observed 396.0796.

i. 2-(4-Bromo-phenyl)-4,5-bis-(4-chloro-phenyl)-4,5-dihydro-1H-imidazole from meso-1,2-bis-(4-chloro-phenyl)-ethane-1,2-diamine and 4-bromo-benzonitrile. HR-MS (FAB, m/z) calculated for $C_{21}H_{16}N_2Cl_2Br$ (M$^+$) 444.9875, observed 449.9877.

j. 4,5-Bis-(4-chloro-phenyl)-2-p-tolyl-4,5-dihydro-1H-imidazole from meso-1,2-bis-(4-chloro-phenyl)-ethane-1,2-diamine and 4-methyl-benzonitrile. HR-MS (EI, m/z) calculated for $C_{22}H_{16}N_2Cl_2$ [(M−2H)$^+$] 378.0690, observed 378.0689.

k. 4,5-Bis-(4-chloro-phenyl)-2-(4-methoxy-phenyl)-4,5-dihydro-1H-imidazole from meso-1,2-bis-(4-chloro-phenyl)-ethane-1,2-diamine and 4-methoxy-benzonitrile. HR-MS (EI, m/z) calculated for $C_{22}H_{16}N_2OCl_2$ [(M−2H)$^+$] 394.0639, observed 394.0644.

l. 4,5-Bis-(4-bromo-phenyl)-2-(4-chloro-phenyl)-4,5-dihydro-1H-imidazole from meso-1,2-bis-(4-bromo-phenyl)-ethane-1,2-diamine (prepared according to the procedure described by Jennerwein, M. et al. *Cancer Res. Clin. Oncol.* 1988, 114, 347–58; Vogtle, F.; Goldschmitt, E. *Chem. Ber.* 1976, 109, 1–40) and 4-chloro-benzonitrile. HR-MS (FAB, m/z) calculated for $C_{21}H_{16}N_2ClBr_2$ [(M+H)$^+$] 488.9368, observed 488.9368.

m. 4-[4,5-Bis-(4-chloro-phenyl)-4,5-dihydro-1H-imidazol-2-yl]-phenol from meso-1,2-bis-(4-chloro-phenyl)-ethane-1,2-diamine and 4-hydroxy-benzonitrile. HR-MS (EI, m/z) calculated for $C_{21}H_{14}N_2OCl_2$ [(M−2H)$^+$] 380.0483, observed 380.0481.

n. 4,5-Bis-(4-chloro-phenyl)-2-(4-trifluoromethyl-phenyl)-4,5-dihydro-1H-imidazole from meso-1,2-bis-(4-chloro-phenyl)-ethane-1,2-diamine and 4-trifluoromethyl-benzonitrile. HR-MS (EI, m/z) calculated for $C_{22}H_{15}N_2Cl_2 F_3$ (M$^+$) 434.0565, observed 434.0567.

o. 2-(4-Chloro-phenyl)-4,5-bis-(4-nitro-phenyl)-4,5-dihydro-1H-imidazole from meso-1,2-bis-(4-nitro-phenyl)-ethane-1,2-diamine (prepared according to the procedure described by Jennerwein, M. et al. *Cancer Res. Clin. Oncol.* 1988, 114, 347–58; Vogtle, F.; Goldschmitt, E. *Chem. Ber.* 1976, 109, 1–40) and 4-chloro-benzonitrile. HR-MS (EI, m/z) calculated for $C_{21}H_{15}N_4O_4Cl$ (M$^+$) 422.0782, observed 422.0778.

p. 2-(4-Chloro-phenyl)-4,5-bis-(4-cyano-phenyl)-4,5-dihydro-1H-imidazole from meso-1,2-bis-(4-cyano-phenyl)-ethane-1,2-diamine (prepared according to the procedure described by Jennerwein, M. et al. *Cancer Res. Clin. Oncol.* 1988, 114, 347–58; Vogtle, F.; Goldschmitt, E. *Chem. Ber.* 1976, 109, 1–40) and 4-chloro-benzonitrile. HR-MS (EI, m/z) calculated for $C_{23}H_{15}N_4Cl$ (M$^+$) 382.0985, observed 382.0990.

q. 4,5-Bis-(4-chloro-phenyl)-2-(4-nitro-phenyl)-4,5-dihydro-1H-imidazole from meso-1,2-bis-(4-chloro-phenyl)-ethane-1,2-diamine and 4-nitro-benzonitrile. HR-MS (EI, m/z) calculated for $C_{21}H_{13}N_3O_2Cl_2$ [(M−2H)$^+$] 409.0385, observed 409.0385.

r. 4,5-Bis-(4-chloro-phenyl)-2-(4-fluoro-phenyl)-4,5-dihydro-1H-imidazole from meso-1,2-bis-(4-chloro-phenyl)-ethane-1,2-diamine and 4-fluoro-benzonitrile. HR-MS (EI, m/z) calculated for $C_{21}H_{15}N_2Cl_2F$ (M$^+$) 384.0596, observed 384.0605.

s. 4,5-Bis-(4-chloro-phenyl)-2-(4-ethoxy-phenyl)-4,5-dihydro-1H-imidazole from meso-1,2-bis-(4-chloro-phenyl)-ethane-1,2-diamine and 4-ethoxy-benzonitrile. HR-MS (ES, m/z) calculated for $C_{23}H_{21}N_2OCl_2$ [(M+H)$^+$] 411.1025, observed 411.1029.

t. 4,5-Bis-(4-chloro-phenyl)-2-(4-methylsulfanyl-phenyl)-4,5-dihydro-1H-imidazole from meso-1,2-bis-(4-chloro-phenyl)-ethane-1,2-diamine and 4-methylsulfanyl-benzonitrile. HR-MS (ES, m/z) calculated for $C_{22}H_{16}N_2Cl_2S$ [(M−2H)$^+$] 410.0409, observed 410.0411.

u. 4,5-Bis-(4-chloro-phenyl)-2-(2,3,4-trimethoxy-phenyl)-4,5-dihydro-1H-imidazole from meso-1,2-bis-(4-chloro-phenyl)-ethane-1,2-dimaine and 2,3,4-trimethoxy-benzonitrile. HR-MS (ES, m/z) calculated for $C_{24}H_{23}N_2O_3Cl_3$ [(M+H)$^+$] 457.1081, observed 457.1084.

v. 4,5-Bis-(4-chloro-phenyl)-2-(2,3-dimethoxy-phenyl)-4,5-dihydro-1H-imidazole from meso-1,2-bis-(4-chloro-phenyl)-ethane-1,2-diamine and 2,3-dimethoxy-benzonitrile. HR-MS (ES, m/z) calculated for $C_{23}H_{21}N_2O_2Cl_2$ [(M+H)$^+$] 427.0975, observed 427.0979.

w. 4,5-Bis-(4-chloro-phenyl)-2-(2,5-dimethoxy-phenyl)-4,5-dihydro-1H-imidazole from meso-1,2-bis-(4-chloro-phenyl)-ethane-1,2-diamine and 2,5-dimethoxy-benzonitrile. HR-MS (ES, m/z) calculated for $C_{23}H_{21}N_2O_2Cl_2$ [(M+H)$^+$] 427.0979, observed 427.0975.

x. 3-[4,5-Bis-(4-chloro-phenyl)-4,5-dihydro-1H-imidazol-2-yl]-4-methoxy-benzoic acid ethyl ester from meso-1,2-bis-(4-chloro-phenyl)-ethane-1,2-diamine and ethyl 3-cyano-4-methoxy-benzoate. HR-MS (ES, m/z) calculated for $C_{25}H_{23}N_2O_3Cl_2$ [(M+H)$^+$] 469.1080, observed 469.1078.

y. 4,5-Bis-(4-chloro-phenyl)-2-(2-fluoro-6-methoxy-phenyl)-4,5-dihydro-1H-imidazole from meso-1,2-bis-(4-chloro-phenyl)-ethane-1,2-diamine and 2-fluoro-6-methoxy-benzonitrile. HR-MS (ES, m/z) calculated for $C_{22}H_{18}N_2OCl_2$ F [(M+H)$^+$] 415.0775, observed 415.0778.

aa. 4,5-Bis-(4-chloro-phenyl)-2-naphthalen-2-yl-4,5-dihydro-1H-imidazole from meso-1,2-bis-(4-chloro-phenyl)-ethane-1,2-diamine and naphthalene-2-carbonitrile. HR-MS (EI, m/z) calculated for $C_{25}H_{16}N_2Cl_2$ [(M−2H)$^+$] 414.0690, observed 414.0684.

bb. 4,5-Bis-(4-chloro-phenyl)-2-(3,4-dimethyl-phenyl)-4,5-dihydro-1H-imidazole from meso-1,2-bis-(4-chloro-phenyl)-ethane-1,2-diamine and 3,4-dimethyl-benzonitrile. HR-MS (EI, m/z) calculated for $C_{23}H_{18}N_2Cl_2$ [(M−2H)$^+$] 392.0847, observed 392.0847.

cc. 4,5-Bis-(4-chloro-phenyl)-2-(3,4-dimethoxy-phenyl)-4,5-dihydro-1H-imidazole from meso-1,2-bis-(4-chloro-phenyl)-ethane-1,2-diamine and 3,4-dimethoxy-benzonitrile. HR-MS (EI, m/z) calculated for $C_{23}H_{18}N_2O_2Cl_2$ [(M−2H)$^+$] 424.0745, observed 424.0743.

dd. 2-Benzo[1,3]dioxol-5-yl-4,5-bis-(4-chloro-phenyl)-4,5-dihydro-1H-imidazole from meso-1,2-bis-(4-chloro-phenyl)-ethane-1,2-diamine and benzo[1,3]dioxole-5-carbonitrile. HR-MS (EI, m/z) calculated for $C_{22}H_{14}N_2O_2Cl_2$ [(M−2H)$^+$] 408.0432, observed 408.0432.

ee. 2-(3-Bromo-4-methoxy-phenyl)-4,5-bis-(4-chloro-phenyl)-4,5-dihydro-1H-imidazole from meso-1,2-bis-(4-chloro-phenyl)-ethane-1,2-diamine and 3-bromo-4-methoxy-benzonitrile. HR-MS (ES, m/z) calculated for $C_{22}H_{18}N_2O_2Cl_2$ Br [(M+H)$^+$] 474.9975, observed 474.9978.

ff. 4,5-Bis-(4-chloro-phenyl)-2-(3,5-dimethoxy-phenyl)-4,5-dihydro-1H-imidazole from meso-1,2-bis-(4-chloro-phenyl)-ethane-1,2-diamine and 3,5-dimethoxy-benzonitrile. HR-MS (EI, m/z) calculated for $C_{23}H_{18}N_2O_2Cl_2$ [(M−2H)$^+$] 424.0745, observed 424.0742.

gg. 4,5-Bis-(4-chloro-phenyl)-2-(2,4-dimethoxy-phenyl)-4,5-dihydro-1H-imidazole from meso-1,2-bis-(4-chloro-phenyl)-ethane-1,2-diamine and 2,4-dimethoxy-benzonitrile. HR-MS (EI, m/z) calculated for $C_{23}H_{18}N_2O_2Cl_2$ [(M−2H)$^+$] 424.0745, observed 424.0746.

hh. 4,5-Bis-(4-bromo-phenyl)-2-(2,4-dimethoxy-phenyl)-4,5-dihydro-1H-imidazole from meso-1,2-bis-(4-bromo-phenyl)-ethane-1,2-diamine and 2,4-dimethoxy-benzonitrile. HR-MS (ES, m/z) calculated for $C_{23}H_{19}N_2O_2Br_2$ [(M−2H)$^+$] 511.9735, observed 511.9740.

EXAMPLE 3

4-[2,5-bis-(4-Chloro-phenyl)-4,5-dihydro-3H-imidazol-4-yl]-benzonitrile

To a solution of meso-1,2-bis-(2-hydroxy-phenyl)-ethane-1,2-diamine (500 mg, 2.047 mmol, prepared according to the procedure described by Vogtle, F.; Goldschmitt, E. *Chem. Ber.* 1976, 109, 1–40) in acetonitrile were added 4-cyanobenzaldehyde (268.4 mg, 2.047 mmol) and 4-chlorobenzaldehyde (287.7 mg, 2.047 mmol). The reaction mixture was stirred at gentle reflux for 12 h. Upon cooling to room temperature, the solvent was removed in vacuo. The residue was suspended in 3 N sulfuric acid and the reaction mixture was heated at reflux for 2 h. Upon cooling to room temperature, the salicylaldehyde by-product was removed by extraction with ether (1×5 mL). The clear aqueous layer was neutralized with 5% sodium hydroxide solution to precipitate out the diamine product (pH>9). 4-[1,2-Diamino-2-(4-chloro-phenyl)-ethyl]-benzonitrile (300 mg, 56%) was collected by filtration, washed with water, and dried under vacuum overnight. It was used without further purification.

Hydrogen chloride gas was passed through a solution of 4-chloro-benzonitrile (1.0 g, 7.3 mmol) in anhydrous ethanol (100 mL) cooled to 0° C. After 3 h, hydrogen chloride gas was stopped and the reaction mixture was stirred at room temperature for 16 h. The solvent was removed and the residue was triturated in diethyl ether to afford ethyl 4-chloro-benzimidate hydrochloride (1.12 g, 83%). It was used without further purification.

A solution of 4-[1,2-diamino-2-(4-chloro-phenyl)-ethyl]-benzonitrile (81 mg, 0.298 mmol) and ethyl 4-chloro-benzimidate hydrochloride (55 mg, 0.249 mmol) in ethanol (5 mL) was heated at 72° C. for 5 h. The solvent was removed, and the residue was taken in methylene chloride (10 mL). The reaction mixture was washed with 1 N sodium hydroxide solution (1 mL) and dried over anhydrous sodium sulfate. The solid was then filtered off, and the filtrate was concentrated in vacuo. Purification of the crude residue by flash chromatography (Biotage system, KP-Sil™ 32–63 μm, 60 Å silica gel) eluting with 0.5% methanol in methylene chloride yielded 4-[2,5-bis-(4-chloro-phenyl)-4,5-dihydro-3H-imidazol-4-yl]-benzonitrile (62 mg, 76%). HR-MS (EI, m/z) calculated for $C_{22}H_{15}N_3Cl_2$ ($M^+$) 391.0643, observed 391.0648.

EXAMPLE 4

In an analogous manner as described in Example 3, there were obtained:

a. 4-[2-(4-Chloro-phenyl)-5-(4-nitro-phenyl)-4,5-dihydro-3H-imidazol-4-yl]-benzonitrile from meso-1,2-bis-(2-hydroxy-phenyl)-ethane-1,2-diamine, 4-chlorobenzaldehyde, 4-cyanobenzaldehyde and 4-chloro-benzonitrile. HR-MS (EI, m/z) calculated for $C_{22}H_{15}N_4O_2Cl$ ($M^+$) 402.0883, observed 402.0884.

b. 2,4-Bis-(4-chloro-phenyl)-5-(4-nitro-phenyl)-4,5-dihydro-1H-imidazole from meso-1,2-bis-(2-hydroxy-phenyl)-ethane-1,2-diamine, 4-chlorobenzaldehyde, 4-nitrobenzaldehyde and 4-chloro-benzonitrile. HR-MS (EI, m/z) calculated for $C_{21}H_{15}N_3O_2Cl_2$ ($M^+$) 411.0541, observed 411.0451.

c. 4-(4-Chloro-phenyl)-2-(4-methoxy-phenyl)-5-(4-nitro-phenyl)-4,5-dihydro-1H-imidazole from meso-1,2-bis-(2-hydroxy-phenyl)-ethane-1,2-diamine, 4-chlorobenzaldehyde, 4-nitrobenzaldehyde and 4-methoxy-benzonitrile. HR-MS (ES, m/z) calculated for $C_{22}H_{18}N_3O_3Cl$ ($M^+$) 407.1037, observed 407.1037.

EXAMPLE 5

2-(2-Benzyloxy-phenyl)-4,5-bis-(4-chloro-phenyl)-4,5-dihydro-1H-imidazole

To a solution of 2-[4,5-bis-(4-chloro-phenyl)-4,5-dihydro-1H-imidazol-2-yl]-phenol (30 mg, 0.0783 mmol) in 3 mL of ethanol were added potassium carbonate (16 mg, 0.117 mmol), benzyl bromide (11 μL, 0.0940 mmol) and tetrabutylammonium iodide (3 mg, 0.1 mmol). The reaction mixture was heated at gentle reflux for 54 h. Additional benzyl bromide (11 μL) and potassium carbonate (16 mg) were added after every 24-hr. Upon cooling to room temperature, the solvent was removed and the residue was taken in methylene chloride. The solution was washed with water, brine and dried over anhydrous sodium sulfate. The solid was then filtered off, and the filtrate was concentrated in vacuo. Purification of the crude residue by flash chromatography (Biotage, KP-Sil™ 32–63 μm, 60 Å silica gel) eluting with 1–6% methanol in methylene chloride yielded 2-(2-benzyloxy-phenyl)-4,5-bis-(4-chloro-phenyl)-4,5-dihydro-1H-imidazole (16.3 mg, 44%). HR-MS (ES, m/z) calculated for $C_{28}H_{23}N_2OCl_2$ [$(M+H)^+$] 473.1185, observed 473.1183.

EXAMPLE 6

In an analogous manner as described in Example 5, there were obtained:

a. 4,5-Bis-(4-chloro-phenyl)-2-(2-ethoxy-phenyl)-4,5-dihydro-1H-imidazole (26%) from 2-[4,5-bis-(4-chloro-phenyl)-4,5-dihydro-1H-imidazol-2-yl]-phenol and iodoethane. HR-MS (ES, m/z) calculated for $C_{23}H_{21}N_2OCl_2$ [$(M+H)^+$] 411.1024, observed 411.1030.

b. 4,5-Bis-(4-chloro-phenyl)-2-(2-isopropoxy-phenyl)-4,5-dihydro-1H-imidazole (38%) from 2-[4,5-bis-(4-chloro-phenyl)-4,5-dihydro-1H-imidazol-2-yl]-phenol and 2-iodopropane. HR-MS (ES, m/z) calculated for $C_{24}H_{23}N_2OCl_2$ [$(M+H)^+$] 425.1181, observed 425.1185.

c. 2-{2-[4,5-Bis-(4-chloro-phenyl)-4,5-dihydro-1H-imidazol-2-yl]-phenoxy}-acetamide (59%) from 2-[4,5-bis-(4-chloro-phenyl)-4,5-dihydro-1H-imidazol-2-yl]-phenol and 2-bromoacetamide. HR-MS (ES, m/z) calculated for $C_{23}H_{20}N_3O_2Cl_2$ [$(M+H)^+$] 440.0927, observed 440.0931.

EXAMPLE 7

4,5-bis-(4-Bromo-phenyl)-2-(2-isopropoxy-phenyl)-4,5-dihydro-1H-imidazole

A reaction mixture of 2-cyanophenol (5 g, 41.55 mmol), cesium carbonate (27.1 g, 83.10 mmol) and 2-iodopropane (7.634 mL, 74.79 mmol) in acetone (80 mL) was heated at 60° C. with vigorous stirring. After 45 min, the gray brown mixture was decanted and the acetone layer was concentrated in vacuo. Water was added to dissolve cesium carbonate, and the product was extracted with diethyl ether (3×200 mL). The organic layers were washed with water, 1 N ammonium hydroxide, brine and dried over anhydrous sodium sulfate. The solid was then filtered off, and the filtrate was concentrated in vacuo. Purification of the crude residue by flash chromatography (Biotage system, KP-Sil™ 32–63 μm, 60 Å silica gel) eluting with 5% ethyl acetate in hexanes yielded 2-isopropoxy-benzonitrile as a colorless liquid (6.6 g, 99%).

Hydrogen chloride gas was passed through a solution of 2-isopropoxy-benzonitrile (6.6 g, 40.49 mmol) in anhydrous ethanol at 0° C. After 30 min, hydrogen chloride gas was stopped. The reaction vessel was sealed with a Teflon stopper and stirred at room temperature for 3 d. The flask was cooled to 0° C. and the stopper was removed. The solvent was removed to give a pale-yellow oil (10.1 g). It was triturated in diethyl ether (100 mL) to afford a white solid. Ethyl 2-isopropoxy-benzimidate hydrochloride (9.17 g, 92%) was collected by filtration, washed with diethyl ether (3×25 mL), and dried in vacuo. It was used without further purification.

To a solution of triethylamine (558 μL, 4 mmol) in ethanol (3 mL) were added meso-1,2-bis-(4-bromo-phenyl)-ethane-1,2-diamine (370 mg, 1.0 mmol) and ethyl 2-isopropoxy-benzimidate hydrochloride (268 mg, 1.1 mmol). The reaction mixture was run on the Smith Microwave instrument at 140° C. under a pressure of 5 psi for 5 min, and at 160° C. under a pressure of 10 psi for 5 min. The reaction mixture was diluted with water, and the product was extracted with methylene chloride (3×50 mL). The organic extracts were washed with 1 N hydrogen chloride solution (2×50 mL), brine and dried over anhydrous sodium sulfate. The solid was then filtered off, and the filtrate was concentrated in vacuo to afford a tan residue (590 mg). It was taken into 20 mL of methylene chloride and diethyl ether (1:1 ratio) and stirred for 1 h. 4,5-Bis-(4-bromo-phenyl)-2-(2-isopropoxy-phenyl)-4,5-dihydro-1H-imidazole hydrochloride (a white solid, 390 mg, 71%) was collected by filtration, washed with diethyl ether (3×5 mL). HR-MS (ES, m/z) calculated for $C_{24}H_{23}N_2OBr_2$ $[(M+H)^+]$ 513.0172, observed 513.0172.

EXAMPLE 8

{4-[4,5-bis-(4-Chloro-phenyl)-4,5-dihydro-1H-imidazol-2-yl]-phenoxy}-acetic Acid Ethyl Ester To a solution of 4-hydroxy-benzonitrile (1 g, 8.395 mmol) in dimethylformamide (10 mL) were added potassium carbonate (2.321 g, 16.79 mmol) and ethyl bromoacetate (1.117 mL, 10.07 mmol), respectively. The reaction mixture was stirred at room temperature for 23 h. It was taken in ethyl acetate and diethyl ether (1:1 ratio), and the solid was filtered off. The filtrate was washed with water, brine and dried over anhydrous sodium sulfate. The solid was then filtered off, and the filtrate was concentrated in vacuo to afford ethyl (4-cyano-phenoxy)-acetate. It was used without further purification.

Hydrogen chloride gas was passed through a solution of ethyl (4-cyano-phenoxy)-acetate (1.48 g, 7.212 mmol) in anhydrous ethanol (160 mL) at 0° C. After 6 h, hydrogen chloride gas was stopped and the reaction vessel was sealed with a Teflon stopper. After being stirred at room temperature for 3 d, the reaction vessel was cooled to 0° C. and the stopper was removed. The solvent was evaporated in vacuo, and the residue was triturated in diethyl ether to give the product as a white solid. Ethyl (4-ethoxy-carbonimidoyl-phenoxy)-acetate hydrochloride (1.74 g, 84%) was collected by filtration and dried under vacuum. It was used without further purification.

A solution of meso-1,2-bis-(4-chloro-phenyl)-ethane-1,2-diamine (500 mg, 1.778 mmol) and ethyl (4-ethoxycarbonimidoyl-phenoxy)-acetate hydrochloride (614 mg, 2.134 mmol) in ethanol (15 mL) was heated at gentle reflux for 24 h. Upon cooling to room temperature, the solvent was removed and the residue was taken in ethyl acetate. It was washed with sodium bicarbonate solution, water, brine and dried over anhydrous sodium sulfate. The solid was then filtered off, and the filtrate was concentrated in vacuo. Purification of the residue by flash chromatography (Biotage system, KP-Sil™ 32–63 μm, 60 Å silica gel) eluting with 2–10% methanol in methylene chloride yielded {4-[4,5-bis-(4-chloro-phenyl)-4,5-dihydro-1H-imidazol-2-yl]-phenoxy}-acetic acid ethyl ester (781 mg, 94%). HR-MS (ES, m/z) calculated for $C_{25}H_{23}N_2O_3Cl_2$ $[(M+H)^+]$ 469.1083, observed 469.1079.

EXAMPLE 9

In an analogous manner as described in Example 8, there were obtained:

a. {2-[4,5-Bis-(4-chloro-phenyl)-4,5-dihydro-1H-imidazol-2-yl]-phenoxy}-acetic acid ethyl ester from meso-1,2-bis-(4-chloro-phenyl)-ethane-1,2-diamine and 2-hydroxy-benzonitrile. HR-MS (ES, m/z) calculated for $C_{25}H_{23}N_2O_3Cl_2$ $[(M+H)^+]$ 469.1080, observed 469.1083.

b. 4,5-Bis-(4-bromo-phenyl)-2-(2-ethoxy-phenyl)-4,5-dihydro-1H-imidazole, hydrochloride salt from meso-1,2-bis-(4-bromo-phenyl)-ethane-1,2-diamine and 2-hydroxy-benzonitrile. HR-MS (ES, m/z) calculated for $C_{23}H_{21}N_2OBr_2$ $[(M+H)^+]$ 499.0015, observed 499.0023.

c. 4,5-Bis-(4-chloro-phenyl)-2-(3-isopropoxy-phenyl)-4,5-dihydro-1H-imidazole, hydrochloride salt from meso-1,2-bis-(4-chloro-phenyl)-ethane-1,2-diamine and 3-hydroxy-benzonitrile. HR-MS (ES, m/z) calculated for $C_{24}H_{20}N_2OCl_2$ $[(M-2H)^+]$ 422.0953, observed 422.0953.

d. d.{3-[4,5-Bis-(4-chloro-phenyl)-4,5-dihydro-1H-imidazol-2-yl]-5-methoxy-phenoxy}-acetic acid ethyl ester from meso-1,2-bis-(4-chloro-phenyl)-ethane-1,2-diamine and 3-hydroxy-5-methoxy-benzonitrile. HR-MS (EI, m/z) calculated for $C_{26}H_{24}N_2O_4Cl_2$ $(M^+)$ 498.1113, observed 498.1117.

EXAMPLE 10

4,5-bis-(4-Chloro-phenyl)-2-(2-ethoxy-5-methyl-phenyl)-4,5-dihydro-1H-imidazole

To a solution of 2-bromo-4-methyl-phenol (1 g, 5.346 mmol) in acetone (10 mL) were added potassium carbonate (740 mg, 5.346 mmol) and ethyl iodide (868 μL, 10.69 mmol). The reaction mixture was heated at gentle reflux for 12 h. The solvent was removed to give a white paste. It was then taken in diethyl ether (5 mL) and water (2 mL). The product was extracted with diethyl ether (2×20 mL). The organic layers were washed with brine (1×5 mL) and dried over anhydrous sodium sulfate. The solid was then filtered off, and the filtrate was concentrated in vacuo. Purification of the crude residue by flash chromatography (Biotage system, KP-Sil™ 32–63 μm, 60 Å silica gel) eluting with 5% ethyl acetate in hexanes yielded 2-bromo-1-ethoxy-4-methyl-benzene (940 mg, 82%).

To a solution of 2-bromo-1-ethoxy-4-methyl-benzene (940 mg, 4.37 mmol) in dimethylformamide (5 mL) at room temperature was added zinc cyanide (513.1 mg, 4.37 mmol). The reaction mixture was degassed by passing argon through for 2 h before tetrakis(triphenylphosphine)palladium (505 mg, 0.437 mmol) was added. The reaction mixture was heated at 90–100° C. under argon for 12 h. The slurry reaction mixture was taken up in diethyl ether (10 mL) and sodium bicarbonate solution (2 mL). The product was extracted with diethyl ether (2×30 mL). The organic layers were washed with water (1×5 mL), brine (1×5 mL) and dried over anhydrous sodium sulfate. The solid was then filtered off, and the filtrate was concentrated in vacuo. Purification of the crude residue by flash chromatography (Biotage system, KP-Sil™ 32–63 μm, 60 Å silica gel) eluting with 10% ethyl acetate in hexanes yielded 2-ethoxy-5-methyl-benzonitrile (232 mg, 33%).

Hydrogen chloride gas was passed through a solution of 2-ethoxy-5-methyl-berzonitrile (200 mg, 1.241 mmol) in anhydrous ethanol (20 mL) at 0° C. After 1 h, hydrogen chloride gas was stopped and the reaction vessel was sealed. After stirring at room temperature for 2 d, the reaction vessel was cooled to 0° C. and opened. The solvent was evaporated in vacuo and the residue was triturated in diethyl ether to afford ethyl 2-ethoxy-5-methyl-benzimidate hydrochloride (300 mg, 99%). It was used without further purification.

A reaction mixture of meso-1,2-bis-(4-chloro-phenyl)-ethane-1,2-diamine (346 mg, 1.231 mmol), ethyl 2-ethoxy-5-methyl-benzimidate hydrochloride (300 mg, 1.231 mmol) and triethylamine (207 µL, 1.477 mmol) in ethanol (10 mL) was heated at reflux for 4 h. The solvent was removed and the residue was taken up in methylene chloride (2 mL) and sodium bicarbonate solution (1 mL). The product was extracted with methylene chloride (2×20 mL). The organic layers were washed with brine (1×5 mL) and dried over anhydrous sodium sulfate. The solid was then filtered off, and the filtrate was concentrated in vacuo. The residue was purified by flash chromatography (Biotage system, KP-Sil™ 32–63 µm, 60 Å silica gel) eluting with 70% ethyl acetate in hexanes to afford 4,5-bis-(4-chloro-phenyl)-2-(2-ethoxy-5-methyl-phenyl)-4,5-dihydro-1H-imidazole (410 mg, 78%). HR-MS (ES, m/z) calculated for $C_{24}H_{23}N_2OCl_2$ [(M+H)$^+$] 425.1182, observed 425.1187.

EXAMPLE 11

In an analogous manner as described in Example 10, there were obtained:
a. 4,5-Bis-(4-chloro-phenyl)-2-(2-ethoxy-4-fluoro-phenyl)-4,5-dihydro-1H-imidazole from meso-1,2-bis-(4-chloro-phenyl)-ethane-1,2-diamine and 2-bromo-5-fluoro-phenol. HR-MS (ES, m/z) calculated for $C_{23}H_{20}N_2OFCl_2$ [(M+H)$^+$] 429.031, observed 429.0936.
b. 4,5-Bis-(4-chloro-phenyl)-2-(4-fluoro-2-isopropoxy-phenyl)-4,5-dihydro-1H-imidazole from meso-1,2-bis-(4-chloro-phenyl)-ethane-1,2-diamine and 2-bromo-5-fluoro-phenol. HR-MS (ES, m/z) calculated for $C_{24}H_{22}N_2OFCl_2$ [(M+H)$^+$] 443.1088, observed 443.1089.

EXAMPLE 12

4,5-bis-(4-Chloro-phenyl)-2-(4-methoxy-2-propoxy-phenyl)-4,5-dihydro-1H-imidazole To a solution of 4-bromoresorcinol (1 g, 5.291 mmol) in acetone (10 mL) were added potassium carbonate (732 mg, 5.291 mmol) and 1-iodopropane (1.799 g, 10.58 mmol), respectively. The reaction mixture was heated at gentle reflux for 6 h. The solvent was removed and the residue was taken in diethyl ether (50 mL). The white solid was filtered off, and the filtrated was concentrated in vacuo. Purification of the crude residue by flash chromatography (Biotage system, KP-Sil™ 32–63 µm, 60 Å silica gel) eluting with 10% ethyl acetate in hexanes yielded 4-bromo-3-propoxy-phenol as a white solid (693 mg, 57%).

To a solution of 4-bromo-3-propoxy-phenol (500 mg, 2.164 mmol) in acetone (10 mL) were added potassium carbonate (299 mg, 2.164 mmol) and methyl iodide (674 µL, 10.82 mmol). The reaction mixture was heated at gentle reflux for 12 h. The solvent was removed and the residue was taken in diethyl ether (50 mL). The white solid was filtered off, and the filtrated was concentrated in vacuo. Purification of the crude residue by flash chromatography (Biotage system, KP-Sil™ 32–63 µm, 60 Å silica gel) eluting with 5–10% ethyl acetate in hexanes yielded 1-bromo-4-methoxy-2-propoxy-benzene as a clear oil (515 mg, 97%).

To a solution of 1-bromo-4-methoxy-2-propoxy-benzene (500 mg, 2.04 mmol) in dimethylformamide (10 mL) at room temperature was added zinc cyanide (240 mg, 2.04 mmol). The reaction mixture was degassed by passing argon through for 2 h before tetrakis(triphenylphosphine) palladium (236 mg, 0.204 mmol) was added. The reaction mixture was heated at 90–100° C. under argon for 12 h. The reaction mixture was taken up in diethyl ether (10 mL) and sodium bicarbonate solution (2 mL). The product was extracted with diethyl ether (2×20 mL). The organic layers were washed with water (1×5 mL), brine (1×5 mL), and dried over anhydrous sodium sulfate. The solid was then filtered off, and the filtrate was concentrated in vacuo. Purification of the crude residue by flash chromatography (Biotage system, KP-Sil™ 32–63 µm, 60 Å silica gel) eluting with 15–20% ethyl acetate in hexanes yielded 4-methoxy-2-propoxy-benzonitrile (290 mg, 74%) as white solids.

Hydrogen chloride gas was passed through a solution of 4-methoxy-2-propoxy-benzonitrile (280 mg, 1.464 mmol) in anhydrous ethanol (20 mL) at 0° C. After 1 h, hydrogen chloride gas was stopped and the reaction vessel was sealed with a stopper. After stirring at room temperature for 2 d, the reaction vessel was cooled to 0° C. and the stopper was removed. The solvent was evaporated in vacuo and the residue was triturated in diethyl ether to afford crude ethyl 4-methoxy-2-propoxy-benzimidate hydrochloride. It was dissolved in ethanol (10 mL), and meso-1,2-bis-(4-chloro-phenyl)-ethane-1,2-diamine (412 mg, 1.464 mmol) and triethylamine (308 µL, 2.194 mmol) were added. The reaction mixture was heated at reflux for 4 h. The solvent was removed and the residue was taken up in methylene chloride (2 mL) and sodium bicarbonate solution (2 mL). The product was extracted with methylene chloride (2×20 mL). The organic layers were washed with brine (1×5 mL) and dried over anhydrous sodium sulfate. The solid was then filtered off, and the filtrate was concentrated in vacuo. The residue was purified by flash chromatography (Biotage system, KP-Sil™ 32–63 µm, 60 Å silica gel) eluting with 70% ethyl acetate in hexanes to afford 4,5-bis-(4-chloro-phenyl)-2-(4-methoxy-2-propoxy-phenyl)-4,5-dihydro-1H-imidazole (303 mg, 46%). HR-MS (ES, m/z) calculated for $C_{25}H_{25}N_2O_2Cl_2$ [(M+H)$^+$] 455.1288, observed 455.1293.

EXAMPLE 13

In an analogous manner as described in Example 12, there were obtained:
a. 4,5-Bis-(4-chloro-phenyl)-2-(2,4-diethoxy-phenyl)-4,5-dihydro-1H-imidazole from meso-1,2-bis-(4-chloro-phenyl)-ethane-1,2-diamine and 4-bromo-resorcinol. HR-MS (ES, m/z) calculated for $C_{25}H_{25}N_2O_2Cl_2$ [(M+H)$^+$] 455.1288, observed 455.1292.
b. 4,5-Bis-(4-chloro-phenyl)-2-(2,4-diisopropoxy-phenyl)-4,5-dihydro-1H-imidazole from meso-1,2-bis-(4-chloro-phenyl)-ethane-1,2-diamine and 4-bromo-resorcinol. HR-MS (ES, m/z) calculated for $C_{27}H_{29}N_2O_2Cl_2$ [(M+H)$^+$] 483.1601, observed 483.1604.
c. 4,5-Bis-(4-bromo-phenyl)-2-(2,4-diethoxy-phenyl)-4,5-dihydro-1H-imidazole from meso-1,2-bis-(4-bromo-phenyl)-ethane-1,2-diamine and 4-bromo-resorcinol. HR-MS (ES, m/z) calculated for $C_{25}H_{25}N_2O_2Br_2$ [(M+H)$^+$] 543.0278, observed 543.0276.

d. 4,5-Bis-(4-chloro-phenyl)-2-[4-methoxy-2-(2-methoxy-ethoxy)-phenyl]-4,5-dihydro-1H-imidazole, trifluoroacetic acid salt from meso-1,2-bis-(4-chloro-phenyl)-ethane-1,2-diarnine and 4-bromo-resorcinol. HR-MS (ES, m/z) calculated for $C_{25}H_{25}N_2O_3Cl_2$ [(M+H)$^+$] 471.1237, observed 471.1239.

e. 4,5-Bis-(4-chloro-phenyl)-2-(4-ethoxy-2-isopropoxy-phenyl)-4,5-dihydro-1H-imidazole from meso-1,2-bis-(4-chloro-phenyl)-ethane-1,2-diamine and 4-bromo-resorcinol. HR-MS (ES, m/z) calculated for $C_{26}H_{26}N_2O_2Cl_2$ [(M+H)$^+$] 469.1444, observed 469.1446.

f. 4,5-Bis-(4-chloro-phenyl)-2-(2-isobutoxy-4-methoxy-phenyl)-4,5-dihydro-1H-imidazole from meso-1,2-bis-(4-chloro-phenyl)-ethane-1,2-diamine and 4-bromo-resorcinol. HR-MS (ES, m/z) calculated for $C_{26}H_{26}N_2O_2Cl_2$ (M$^+$) 469.1444, observed 469.1449.

g. 4,5-Bis-(4-chloro-phenyl)-2-(4-ethoxy-2-methoxy-phenyl)-4,5-dihydro-1H-imidazole from meso-1,2-bis-(4-chloro-phenyl)-ethane-1,2-diamine and 4-bromo-resorcinol. HR-MS (ES, m/z) calculated for $C_{24}H_{23}N_2O_2Cl_2$ [(M+H)$^+$] 441.1131, observed 441.1137.

h. 4,5-Bis-(4-chloro-phenyl)-2-(2-ethoxy-5-methoxy-phenyl)-4,5-dihydro-1H-imidazole from meso-1,2-bis-(4-chloro-phenyl)-ethane-1,2-diamine and 2-bromo-benzene-1,4-diol. HR-MS (ES, m/z) calculated for $C_{24}H_{23}N_2O_2Cl_2$ [(M+H)$^+$] 441.1131, observed 441.1136.

i. 4,5-Bis-(4-chloro-phenyl)-2-(2-isopropoxy-5-methoxy-phenyl)-4,5-dihydro-1H-imidazole from meso-1,2-bis-(4-chloro-phenyl)-ethane-1,2-diamine and 2-bromo-benzene-1,4-diol. HR-MS (ES, m/z) calculated for $C_{25}H_{24}N_2O_2Cl_2$ [(M+H)$^+$] 455.1288, observed 455.1293.

j. 4,5-Bis-(4-chloro-phenyl)-2-(5-ethoxy-2-isopropoxy-phenyl)-4,5-dihydro-1H-imidazole from meso-1,2-bis-(4-chloro-phenyl)-ethane-1,2-diamine and 2-bromo-benzene-1,4-diol. HR-MS (ES, m/z) calculated for $C_{26}H_{27}N_2O_2Cl_2$ [(M+H)$^+$] 469.1444, observed 469.1446.

EXAMPLE 14

2-(4-Chloro-2-ethoxy-phenyl)-4,5-bis-(4-chloro-phenyl)-4,5-dihydro-1H-imidazole

To a solution of 4-chloro-2-fluoro-benzonitrile (1 g, 6.428 mmol) in ethanol (10 mL) were added sodium ethoxide solution (4.8 mL, 12.86 mmol, 21% wt in ethanol). The reaction mixture was heated at gently reflux for 12 h. The solvent was removed and the residue was partitioned between water (10 mL) and diethyl ether (20 mL). The layers were separated and the product was extracted with diethyl ether (20 mL). The organic layers were washed with brine (5 mL) and dried over anhydrous sodium sulfate. The solid was filtered off, and the filtrate was concentrated in vacuo. Purification of the residue by flash chromatography (Biotage system, KP-Sil™ 32–63 μm, 60 Å silica gel) eluting with 5% ethyl acetate in hexanes yielded 4-chloro-2-ethoxy-benzonitrile (670 mg, 57%).

Hydrogen chloride gas was passed through a solution of 4-chloro-2-ethoxy-benzonitrile (670 mg, 3.689 mmol) in anhydrous ethanol (25 mL) cooled to 0° C. After 45 min, the hydrogen chloride gas was stopped and the reaction vessel was sealed with a Teflon stopper. It was stirred at room temperature for 5 d. The reaction vessel was cooled to 0° C. and the stopper was removed. The solvent was removed and the residue was triturated in diethyl ether to afford ethyl 4-chloro-2-ethoxy-benzimidate hydrochloride (913 mg, 94%). It was used without further purification.

To a solution of meso-1,2-bis-(4-chloro-phenyl)-ethane-1,2-diamine (810 mg, 2.879 mmol) and ethyl 4-chloro-2-ethoxy-benzimidate hydrochloride (913 mg, 3.455 mmol) in ethanol (10 mL) was added triethylamine (605 μL, 4.319 mmol). The reaction mixture was heated at gentle reflux for 4 h. The solvent was evaporated to dryness and the residue was purified by flash chromatography (Biotage system, KP-Sil™ 32–63 μm, 60 Å silica gel) eluting with 70% ethyl acetate in hexanes to afford 2-(4-chloro-2-ethoxy-phenyl)-4,5-bis-(4-chloro-phenyl)-4,5-dihydro-1H-imidazole (1.045 g, 81%). HR-MS (ES, m/z) calculated for $C_{23}H_{20}N_2OCl_3$ [(M+H)$^+$]445.0636, observed 445.0644.

EXAMPLE 15

4,5-bis-(4-Chloro-phenyl)-2-(2-ethoxy-4-trifluoromethyl-phenyl)-4,5-dihydro-1H-imidazole To a solution of 2-nitro-4-trifluoromethyl-benzonitrile (4.052 g, 18 mmol) in ethanol (25 mL) were added sodium ethoxide solution (13.4 mL, 36 mmol, 21% wt in ethanol) dropwise over 30 min. The reaction mixture was stirred at room temperature for 1 h. Water (50 mL) was added and the resulting mixture was stirred for 15 min. The solid was filtered off, washed with water and dried under vacuum for 3 d to give 2-ethoxy-4-trifluoromethyl-benzonitrile as a beige solid (2.85 g, 74%). It was used without further purification.

Hydrogen chloride gas was passed through a solution of 2-ethoxy-4-trifluoro-methyl-benzonitrile (1.506 g, 7 mmol) in anhydrous ethanol (60 mL) cooled to 0° C. After 45 min, the hydrogen chloride gas was stopped and the reaction vessel was sealed with a Teflon stopper. It was stirred at room temperature for 5 d. The reaction vessel was cooled to 0° C. and the stopper was removed. The solvent was removed and the residue was triturated in diethyl ether to afford ethyl 2-ethoxy-4-trifluoromethyl-benzimidate hydrochloride (1.84, 88%). It was used without further purification.

To a solution of meso-1,2-bis-(4-chloro-phenyl)-ethane-1,2-diamine (1.102 g, 3.92 mmol) and ethyl 2-ethoxy-4-trifluoromethyl-benzimidate hydrochloride (1.167 g, 3.92 mmol) in ethanol (30 mL) was added triethylamine (820 μL, 5.88 mmol). The reaction mixture was heated at gentle reflux for 4 h. The solvent was evaporated to dryness and the residue was partitioned between ethyl acetate and sodium bicarbonate solution. The aqueous layer was extracted with ethyl acetate. The organic layers were washed with brine and dried over anhydrous magnesium sulfate. The solid was filtered off, and the filtrate was concentrated in vacuo. The residue was purified by flash chromatography (Biotage system, KP-Sil™ 32–63 pm, 60 Å silica gel) eluting with 35% ethyl acetate in hexanes to afford 4,5-bis-(4-chloro-phenyl)-2-(2-ethoxy-4-trifluoromethyl-phenyl)-4,5-dihydro-1H-imidazole (1.3 g, 69%). HR-MS (ES, m/z) calculated for $C_{24}H_{19}N_2OF_3Cl_2$ [(M+H)$^+$] 479.0903, observed 479.0900.

EXAMPLE 16

4,5-Bis-(4-chloro-phenyl)-2-(2-isopropoxy-4-trifluoromethyl-phenyl)-4,5-dihydro-1H-imidazole was prepared from 2-nitro-4-trifluoromethyl-benzonitrile and meso-1,2-bis-(4-chloro-phenyl)-ethane-1,2-diamine in an analogous manner as described in example 15. HR-MS (ES, m/z) calculated for $C_{25}H_{22}N_2OF_3Cl_2$ [(M+H)$^+$] 493.1056, observed 493.1061.

EXAMPLE 17

4,5-bis-(4-Chloro-phenyl)-2-(3-pyrrolidin-1-yl-phenyl)-4,5-dihydro-1H-imidazole

A reaction mixture of 3-bromo-benzonitrile (0.91 g, 5 mmol), tris(dibenzylideneacetone)-dipalladium (229 mg), (S)-2,2'-bis(diphenylphosphino)-1,1'-binaphthyl (311 mg, 0.5 mmol), sodium tert-butoxide (740 mg, 7.7 mmol), pyrrolidine (0.58 mL, 6.9 mmol) in tetrahydrofuran (10 mL) was heated at 80° C. in a sealed tube for 6 h. The reaction mixture was worked up with water and diethyl ether. The organic layers were washed with brine and dried over anhydrous magnesium sulfate. The solid was then filtered off, and the filtrate was concentrated in vacuo. Purification of the crude residue by flash chromatography (Biotage system, KP-Sil™ 32–63 μm, 60 Å silica gel) eluting with 0–5% ethyl acetate in hexanes yielded 3-pyrrolidin-1-yl-benzonitrile (45 mg, 5%).

Hydrogen chloride gas was passed through a solution of 3-pyrrolidin-1-yl-benzonitrile (45 mg, 0.26 mmol) in ethanol (5 mL) at 0° C. for 2 h. The flask was sealed with a septum and stirred overnight at room temperature. The flask was cooled to 0° C. and the septum was removed. The reaction mixture was concentrated in vacuo to dryness then meso-1,2-bis-(4-chloro-phenyl)-ethane-1,2-diamine (73 mg, 0.26 mmol) and ethanol (3 mL) were added. The mixture was heated at reflux for 3 h. Sodium bicarbonate solution was added and the product was extracted with methylene chloride. The organic layers were washed with brine and dried over anhydrous potassium carbonate. The solid was then filtered off, and the filtrate was concentrated in vacuo. Purification of the residue by flash chromatography (Biotage system, KP-Sil™ 32–63 μm, 60 Å silica gel) eluting with 0–8% methanol in methylene chloride yielded 4,5-bis-(4-chloro-phenyl)-2-(3-pyrrolidin-1-yl-phenyl)-4,5-dihydro-1H-imidazole as an off-white solid (42 mg, 37%). HR-MS (ES, m/z) calculated for $C_{25}H_{24}N_3Cl_2$ [(M+H)$^+$] 436.1342, observed 436.1346.

EXAMPLE 18

4,5-bis-(4-Chloro-phenyl)-2-(2-isopropoxy-4-methoxy-phenyl)-4,5-dihydro-1H-imidazole A mixture of the 2-hydroxy-4-methoxybenzaldehyde (20 g, 128.8 mmol), sodium acetate (35.05 g, 257.6 mmol) and nitroethane (19 mL, 257.6 mmol) in glacial acetic acid (100 mL) was heated at gentle reflux for 12 h. The reaction mixture was then poured into ~1000 mL of ice water (1:1 ratio of ice and water). The product was extracted with ethyl acetate (3×200 mL). The organic extracts were washed with sodium bicarbonate solution until the aqueous layer had pH ~8. The organic layers were then dried over anhydrous magnesium sulfate, and concentrated in vacuo to afford 2-hydroxy-4-methoxy-benzonitrile as a yellow oil (16.5 g, 86%). It was used without further purification.

To a solution of 2-hydroxy-4-methoxy-benzonitrile (16.4 g, 134.1 mmol) in ethanol were added potassium carbonate (37.07 g, 268.2 mmol) and 2-iodopropane (40.16 mL, 402.3 mmol). The reaction mixture was heated at gentle reflux for 3.5 h. The solvent was removed to afford a brown paste. It was then taken in diethyl ether (300 mL) and water (200 mL). The layers were separated and the aqueous layer was extracted with diethyl ether (3×100 mL). The combined organic extracts were washed with brine and dried over anhydrous magnesium sulfate. The solid was then filtered off, and the filtrate was concentrated in vacuo. Purification of the crude residue by flash chromatography (Biotage system, KP-Sil™ 32–63 μm, 60 Å silica gel) eluting with 12% ethyl acetate in hexanes yielded 2-isopropoxy-4-methoxy-benzonitrile as a pale-yellow oil (11.8 g, 56%).

Hydrogen chloride gas was passed through a solution of 2-isopropoxy-4-methoxy-benzonitrile (11.5 g, 60.14 mmol) in anhydrous ethanol (250 mL) cooled to −10° C. After 45 min, hydrogen chloride gas was stopped and the reaction mixture was stirred at room temperature in a closed reaction vessel for 2 weeks. The reaction vessel was cooled to 0° C. before the stopper was removed. Argon gas was passed through the solution to remove excess hydrogen chloride gas. The solvent was evaporated and the residue was triturated in diethyl ether (100 mL) to afford ethyl 2-isopropoxy-4-methoxy-benzimidate hydrochloride (16.3 g, 99%). It was used without further purification.

To a solution of meso-1,2-bis-(4-chloro-phenyl)-ethane-1,2-diamine (7 g, 24.89 mmol) and ethyl 2-isopropoxy-4-methoxy-benzimidate hydrochloride (7.155 g, 26.13 mmol) in ethanol (100 mL) was added triethylamine (3.661 mL, 26.13 mmol). The reaction mixture was heated at gentle reflux for 4 h. The solvent was removed in vacuo and the residue was then taken in methylene chloride (100 mL) and sodium bicarbonate (20 mL). The product was extracted with methylene chloride (2×50 mL). The organic layers were washed with brine (1×10 mL) and dried over anhydrous sodium sulfate. The solid was then filtered off, and the filtrate was concentrated in vacuo. Purification of the crude residue by flash chromatography (Biotage system, KP-Sil™ 32–63 μm, 60 Å silica gel) eluting with 70% ethyl acetate in hexanes yielded 4,5-bis-(4-chloro-phenyl)-2-(2-isopropoxy-4-methoxy-phenyl)-4,5-dihydro-1H-imidazole as an off-white solid (8.505 g, 75%). HR-MS (ES, m/z) calculated for $C_{25}H_{24}N_2O_2Cl_2$ (M$^+$) 455.1288, observed 455.1291.

EXAMPLE 19

In an analogous manner as described in Example 18, there were obtained:

a. 4,5-Bis-(4-chloro-phenyl)-2-(2-ethoxy-4-methoxy-phenyl)-4,5-dihydro-1H-imidazole from 2-hydroxy-4-methoxy-benzonitrile and meso-1,2-bis-(4-chloro-phenyl)-ethane-1,2-diamine. HR-MS (ES, m/z) calculated for $C_{24}H_{23}N_2O_2Cl_2$ [(M+H)$^+$] 441.1131, observed 441.1136.

b. 4,5-Bis-(4-chloro-phenyl)-2-[2-(1-ethyl-propoxy)-4-methoxy-phenyl]-4,5-dihydro-1H-imidazole from 2-hydroxy-4-methoxy-benzonitrile and meso-1,2-bis-(4-chloro-phenyl)-ethane-1,2-diamine. HR-MS (ES, m/z) calculated for $C_{27}H_{29}N_2O_2Cl_2$ [(M+H)$^+$] 483.1601, observed 483.1606.

c. 4,5-Bis-(4-bromo-phenyl)-2-(2-ethoxy-4-methoxy-phenyl)-4,5-dihydro-1H-imidazole from 2-hydroxy-4-methoxy-benzonitrile and meso-1,2-bis-(4-bromo-phenyl)-ethane-1,2-diamine. HR-MS (ES, m/z) calculated for $C_{24}H_{23}N_2O_2Br_2$ [(M+H)$^+$] 529.0121, observed 529.0123.

d. 4,5-Bis-(4-bromo-phenyl)-2-(2-isopropoxy-4-methoxy-phenyl)-4,5-dihydro-1H-imidazole from 2-isopropoxy-4-methoxy-benzonitrile and meso-1,2-bis-(4-bromo-phenyl)-ethane-1,2-diamine. HR-MS (ES, m/z) calculated for $C_{25}H_{25}N_2O_2Br_2$ [(M+H)$^+$] 543.0278, observed 543.0284.

e. 4,5-Bis-(4-cyano-phenyl)-2-(2-isopropoxy-4-methoxy-phenyl)-4,5-dihydro-1H-imidazole from 2-isopropoxy-4-methoxy-benzonitrile and meso-1,2-bis-(4-cyano-phenyl)-ethane-1,2-diamine. HR-MS (ES, m/z) calculated for $C_{27}H_{25}N_4O_2$ [(M+H)$^+$] 437.1972, observed 437.1975.

f. 4-[5-(4-Chloro-phenyl)-2-(2-isopropoxy-4-methoxy-phenyl)-4,5-dihydro-1H-imidazol-4-yl]-benzonitrile from 2-isopropoxy4-methoxy-benzonitrile and 4-[1,2-diamino-2-(4-chloro-phenyl)-ethyl]-benzonitrile. HR-MS (ES, m/z) calculated for $C_{26}H_{25}N_3O_2Cl$ [(M+H)$^+$] 446.1630, observed 446.1631.

g. 4,5-Bis-(4-chloro-phenyl)-2-[2-(2-fluoro-ethoxy)-4-methoxy-phenyl]-4,5-dihydro-1H-imidazole, hydrochloride salt from 2-hydroxy-4-methoxy-benzonitrile and meso-1,2-bis-(4-cyano-phenyl)-ethane-1,2-diamine. HR-MS (ES, m/z) calculated for $C_{24}H_{21}N_2O_2FCl_2$ [(M+H)$^+$] 459.1037, observed 459.1042.

EXAMPLE 20

4,5-bis-(4-Chloro-phenyl)-2-chroman-8-yl-4,5-dihydro-1H-imidazole

To a solution of 8-bromo-chroman (1.434 g, 6.730 mmol, prepared from 2,6-dibromo-phenol using the procedure reported by Thomas, G. H. et al. *Tetrahedron Lett*. 1998, 39, 2219–22) in dimethylformamide (10 mL) at room temperature was added zinc cyanide (790 mg, 6.730 mmol). The mixture was degassed by passing argon through for 2 h before tetrakis(triphenylphosphine)palladium (778 mg, 0.673 mmol) was added. The reaction mixture was heated at 90° C. for 12 h. Upon cooling to room temperature, it was diluted with diethyl ether (100 mL) and washed with sodium bicarbonate, brine and dried over anhydrous sodium sulfate. The solid was filtered off, and the filtrate was concentrated in vacuo. Purification of the crude residue by flash chromatography (Biotage system, KP-Sil™ 32–63 μm, 60 Å silica gel) eluting with 10–20% ethyl acetate in hexanes yielded chroman-8-carbonitrile (370 mg, 35%).

Hydrogen chloride gas was passed through a solution of chroman-8-carbonitrile (370 mg, 1.736 mmol) in anhydrous ethanol (15 mL) at 0° C. After 1 h, hydrogen chloride gas was stopped and the reaction vessel was sealed with a stopper. After stirring at room temperature for 1 d, the reaction vessel was cooled to 0° C. and the stopper was removed. The solvent was evaporated in vacuo to afford chroman-8-carboximidic acid ethyl ester hydrochloride (491 mg, 88%). It was used without further purification.

A solution of meso-1,2-bis-(4-chloro-phenyl)-ethane-1,2-diamine (352 mg, 1.25 mmol), chroman-8-carboximidic acid ethyl ester hydrochloride (491 mg, 2.031 mmol) and triethylamine (350 μL, 2.5 mmol) in ethanol (10 mL) was heated at reflux for 12 h. The solvent was removed and the residue was purified by flash chromatography (Biotage system, KP-Sil™ 32–63 μm, 60 Å silica gel) eluting with 0–5% methanol in ethyl acetate to afford 4,5-bis-(4-chloro-phenyl)-2-chroman-8-yl-4,5-dihydro-1H-imidazole as an off-white foam (189 mg, 36%). HR-MS (ES, m/z) calculated for $C_{24}H_{21}N_2OCl_2$ [(M+H)$^+$] 423.126, observed 423.1026.

EXAMPLE 21

4,5-Bis-(4-chloro-phenyl)-2-(2,3-dihydro-benzofuran-7-yl)-4,5-dihydro-1H-imidazole was prepared from 7-bromo-2,3-dihydro-benzofuran (prepared from 2,6-dibromo-phenol using the procedure reported by Thomas, G. H. et al. *Tetrahedron Lett*. 1998, 39, 2219–22) and meso-1,2-bis-(4-chloro-phenyl)-ethane-1,2-diamine in an analogous manner as described in example 20. HR-MS (ES, m/z) calculated for $C_{23}H_{19}N_2OCl_2$ [(M+H)$^+$] 409.0869, observed 409.0871.

EXAMPLE 22

4,5-bis-(4-Chloro-phenyl)-2-(4-ethyl-2-isopropoxy-phenyl)-4,5-dihydro-1H-imidazole Iodine (6.35 g, 25 mmol) in methylene chloride (360 mL) was added dropwise over 3 h to a stirred suspension of 3-ethyl-phenol (3.05 g, 25 mmol) and thallium (I) acetate (7.90 g, 30 mmol) in methylene chloride (300 mL). The resulting mixture was stirred at room temperature for 24 h and filtered. The filtrate was concentrated in vacuo and the residue was purified by flash chromatography (Biotage system, KP-Sil™ 32–63 μm, 60 Å silica gel) eluting with 0–5% ethyl acetate in hexanes to afford 5-ethyl-2-iodophenol (3.49g, 56%).

A mixture of 5-ethyl-2-iodophenol (1.0 g, 4 mmol), potassium carbonate (1.10 g, 8 mmol) and 2-iodopropane (0.80 mL, 8 mmol) was heated at reflux for 6 h. The reaction mixture was cooled to room temperature and water was added. The mixture was extracted with diethyl ether. The combined organic extracts were washed with brine and dried over anhydrous magnesium sulfate. The solid was then filtered off, and the filtrate was concentrated in vacuo. Purification of the residue by flash chromatography (Biotage system, KP-Sil™ 32–63 μm, 60 Å silica gel) eluting with hexanes, 5% ethyl acetate in hexanes yielded 4-ethyl-1-iodo-2-isopropoxy-benzene (0.93 g, 80%).

4-Ethyl-1-iodo-2-isopropoxy-benzene (0.93 g, 3.2 mmol) was dissolved in dimethylformamide (5 mL). Zinc cyanide (226 mg, 1.92 mmol) was added. Argon gas was passed through the mixture for 10 min. Tetrakis (triphenylphosphine)-palladium(184 mg, 0.16 mmol) was added and the mixture was heated at 90° C. for 5 h. The reaction mixture was cooled to room temperature and poured into water. The mixture was extracted with diethyl ether. The organic extracts were washed with brine and dried over anhydrous magnesium sulfate. The solid was then filtered off, and the filtrate was concentrated in vacuo. Purification of the residue by flash chromatography (Biotage system, KP-Sil™ 32–63 μm, 60 Å silica gel) eluting with 10% diethyl ether in hexanes yielded 4-ethyl-2-isopropoxy-benzonitrile (0.34 g, 56%).

Hydrogen chloride gas was passed through a solution of 4-ethyl-2-isopropoxy-benzonitrile (0.34 g, 1.80 mmol) in ethanol (5 mL) at 0° C. for 2 h. The flask was sealed with a septum and stirred for 2 d at room temperature. The flask was cooled to 0° C. and the septum was removed. The reaction mixture was concentrated in vacuo to dryness, then a solution of meso-1,2-bis-(4-chloro-phenyl)-ethane-1,2-diamine (0.458 g, 1.62 mmol) in ethanol (5 mL) was added. The mixture was heated at reflux for 5 h. Sodium bicarbonate solution was added and the product was extracted with ethyl acetate. The organic layers were washed with brine and dried over anhydrous sodium sulfate. The solids were then filtered off, and the filtrate was concentrated in vacuo. Purification of the residue by flash chromatography (Biotage system, KP-Sil™ 32–63 μm, 60 Å silica gel) eluting with 1–2% methanol in methylene chloride yielded 4,5-bis-(4-chloro-phenyl)-2-(4-ethyl-2-isopropoxy-phenyl)-4,5-dihydro-1H-imidazole as a white foam (0.295 g, 36%). HR-MS (ES, m/z) calculated for $C_{26}H_{27}N_2OCl_2$ [(M+H)$^+$] 453.1495, observed 453.1498.

EXAMPLE 23

In an analogous manner as described in Example 22, there were obtained:

a. 4,5-Bis-(4-chloro-phenyl)-2-(2-ethoxy-4-ethyl-phenyl)-4,5-dihydro-1H-imidazole from 5-ethyl-2-iodophenol and meso-1,2-bis-(4-chloro-phenyl)-ethane-1,2-diamine. HR-MS (ES, m/z) calculated for $C_{25}H_{25}N_2OCl_2$ [(M+H)$^+$] 439.1339, observed 439.1343.

b. 4,5-Bis-(4-chloro-phenyl)-2-(2-ethoxy-4-methyl-phenyl)-4,5-dihydro-1H-imidazole from m-cresol and meso-1,2-bis-(4-chloro-phenyl)-ethane-1,2-diamine. HR-MS (ES, m/z) calculated for $C_{24}H_{23}N_2OCl_2$ [(M+H)$^+$] 425.1182, observed 425.1185.

c. {4-[4,5-Bis-(4-chloro-phenyl)-4,5-dihydro-1H-imidazol-2-yl]-3-ethoxy-phenyl}-dimethyl-amine from 3-dimethylamino-phenol and meso-1,2-bis-(4-chloro-phenyl)-ethane-1,2-diamine. HR-MS (ES, m/z) calculated for $C_{25}H_{26}N_3OCl_2$ [(M+H)$^+$] 454.1448, observed 454.1452.

EXAMPLE 24

(2-{2-[4,5-bis-(4-Chloro-phenyl)-4,5-dihydro-1H-imidazol-2-yl]-5-methoxy-phenoxy}-ethyl)-dimethyl-amine To a solution of 3-methoxy-phenol (1 g, 8.055 mmol) in tetrahydrofuran (30 mL) at room temperature was added N-bromosuccinimide (1.478 g, 8.055 mmol) in several portions. The yellow reaction mixture was stirred at room temperature for 12 h. Sodium bicarbonate solution (5 mL) was added and the product was extracted with diethyl ether (2×100 mL). The organic layers were washed with brine (1×20 mL) and dried over anhydrous sodium sulfate. The solid was then filtered off, and the filtrate was concentrated in vacuo. Purification of the crude residue by flash chromatography (Biotage system, KP-Sil™ 32–63 µm, 60 Å silica gel) eluting with 10–30% ethyl acetate in hexanes yielded 2-bromo-5-methoxy-phenol (0.801 g, 49%) and 4-bromo-5-methoxy-phenol (0.396 g, 24%).

Zinc cyanide (1.282 g, 0.770 mmol) and 2-bromo-5-methoxy-phenol (3 g, 14.18 mmol) were taken into dimethylformamide (15 mL) and the mixture was degassed with argon for 45 min. To this was added tetrakis (triphenylphosphine)palladium (993 mg, 0.852 mmol), and the reaction mixture was sealed after being degassed for 30 min. After heated at 95° C. for 2 d, the reaction mixture was cooled to room temperature and worked up with water and diethyl ether. The ethereal extracts were washed with brine and dried over anhydrous sodium sulfate. The solid was then filtered off, and the filtrate was concentrated in vacuo. Purification of the crude residue by flash chromatography (Biotage system, KP-Sil™ 32–63 µm, 60 Å silica gel) eluting with 0–25% ethyl acetate in hexanes yielded 2-hydroxy-4-methoxy-benzonitrile (334 mg, 16%).

To a solution of 2-hydroxy-4-methoxy-benzonitrile (200 mg, 1.341 mmol) in acetone (5 mL) were added cesium carbonate (1.312 g, 4.023 mmol) and (2-chloroethyl)-dimethylamine hydrochloride (390 mg, 2.682 mmol). The resulting mixture was heated at 60° C. for overnight. The solid was filtered off and washed with methylene chloride (6×10 mL). The filtrate was washed with sodium bicarbonate solution, brine and dried over anhydrous sodium sulfate. The solid was then filtered off, and the filtrate was concentrated in vacuo. Purification of the residue by flash chromatography (Biotage system, KP-Sil™ 32–63 µm, 60 Å silica gel) eluting with 0–5% methanol in methylene chloride yielded 2-(2-dimethylamino-ethoxy)-4-methoxy-benzonitrile as a pale-yellow oil (210 mg, 71%).

Hydrogen chloride gas was passed through a solution of 2-(2-dimethylamino-ethoxy)-4-methoxy-benzonitrile (200 mg, 0.908 mmol) in anhydrous ethanol (10 mL) at 0° C. After 45 min, hydrogen chloride gas was stopped and the reaction vessel was sealed with a septum. After stirring at room temperature for 3 d, the reaction vessel was cooled to 0° C. and the septum was removed. The solvent was removed in vacuo to afford ethyl 2-(2-dimethylamino-ethoxy)-4-methoxy-benzimidate hydrochloride as a pale-yellow foam (310 mg, 96%). It was used without further purification.

A solution of meso-1,2-bis-(4-chloro-phenyl)-ethane-1,2-diamine (180 mg, 0.640 mmol), ethyl 2-(2-dimethylamino-ethoxy)-4-methoxy-benzimidate hydrochloride (290 mg, 0.768 mmol) and triethylamine (178 µL, 1.28 mmol) in ethanol (3 mL) was heated at 85° C. overnight. The solvent was removed and the residue was taken into methylene chloride. It was washed with sodium bicarbonate solution and dried over anhydrous sodium sulfate. The residue was purified by flash chromatography (Biotage system, KP-Sil™ 32–63 µm, 60 Å silica gel) eluting with 0–20% methanol in hexanes to afford (2-{2-[4,5-bis-(4-chloro-phenyl)-4,5-dihydro-1H-imidazol-2-yl]-5-methoxy-phenoxy}-ethyl)-dimethyl-amine as a white foam (153 mg, 49%). HR-MS (ES, m/z) calculated for $C_{26}H_{28}N_3O_2Cl_2$ [(M+H)$^+$] 484.1553, observed 484.1560.

EXAMPLE 25

4,5-bis-(4-Chloro-phenyl)-2-(2-cyclopentyloxy-4-methoxy-phenyl)-4,5-dihydro-1H-imidazole To a solution of 2-hydroxy-4-methoxy-benzonitrile (90 mg, 0.573 mmol), cyclopentanol (55 mg, 0.630 mmol) and triphenylphosphine (167 mg, 0.630 mmol) in tetrahydrofuran (3 mL) cooled to −78° was added diethylazodicarboxalate (0.16 mL, 0.860 mmol). The cooling bath was removed and the reaction was allowed to warm up to room temperature over 1.5 h. The reaction mixture was concentrated in vacuo, and purification of the residue by flash chromatography (Biotage system, KP-Sil™ 32–63 µm, 60 Å silica gel) eluting with 0–8% diethyl ether in hexanes yielded 2-cyclopentyloxy-4-methoxy-benzonitrile as a clear liquid (125 mg, 96%).

Hydrogen chloride gas was passed through a solution of 2-cyclopentyloxy-4-methoxy-benzonitrile (120 mg, 0.552 mmol) in anhydrous ethanol (15 mL) at 0° C. After 45 min, hydrogen chloride gas was stopped and the reaction vessel was sealed with a septum. After stirring at room temperature for 3 d, the reaction vessel was cooled to 0° C. and the septum was removed. The solvent was removed in vacuo to afford ethyl 2-cyclopentyloxy-4-methoxy-benzimidate hydrochloride as a yellow oil (169 mg). It was dissolved methanol (2 mL) and meso-1,2-bis-(4-chloro-phenyl)-ethane-1,2-diamine (160 mg, 0.569 mmol) was added. The solution was heated at 85° C. for 2 h. The solvent was removed and the residue was taken into diethyl ether. It was washed with sodium bicarbonate solution, water and dried over anhydrous sodium sulfate and concentrated in vacuo. The residue was purified by flash chromatography (Biotage system, KP-Sil™ 32–63 µm, 60 Å silica gel) eluting with 0–25% diethyl ether in methylene chloride to afford 4,5-bis-(4-chloro-phenyl)-2-(2-cyclopentyloxy-4-methoxy-phenyl)-

4,5-dihydro-1H-imidazole as a white foam (102 mg, 37%). HR-MS (ES, m/z) calculated for $C_{27}H_{27}N_2O_2Cl_2$ [(M+H)$^+$] 481.1448, observed 481.1444.

EXAMPLE 26

1-(2-{2-[4,5-Bis-(4-chloro-phenyl)-4,5-dihydro-1H-imidazol-2-yl]-5-methoxy-phenoxy}-ethyl)-1H-imidazole was prepared from 2-hydroxy-4-methoxy-benzonitrile and meso-1,2-bis-(4-chloro-phenyl)-ethane-1,2-diamine in an analogous manner as described in example 25. HR-MS (ES, m/z) calculated for $C_{27}H_{25}N_4O_2Cl_2$ [(M+H)$^+$] 507.1349, observed 507.1349.

EXAMPLE 27

3-[4,5-bis-(4-Chloro-phenyl)-4,5-dihydro-1H-imidazol-2-yl]-5-methoxymethyl-benzoic Acid Ethyl Ester To a mixture of activated manganese dioxide (1.75 g, 2 mmol) and Celite (~50 mg) in methylene chloride (6 mL) at room temperature was added a solution of 3-hydroxymethyl-5-methoxymethyl-benzonitrile (178 mg, 1 mmol) in methylene chloride (2 mL) was added. The reaction mixture was stirred at room temperature for 4 h, then the solid was filtered off and washed with methylene chloride and ethyl acetate. The filtrated was concentrated in vacuo to afford 3-fornyl-5-methoxymethyl-benzonitrile (128 mg, 73%).

To a reaction mixture of 3-formyl-5-methoxymethyl-benzonitrile (128 mg, 0.73 mmol) in tert-butyl alcohol (3 mL) and water (1.5 mL) were added 2-methyl-2-butene (1.5 mL) and sodium chlorite (198 mg, 80% technical grade, dissolved in 1.5 mL of water), respectively. The resulting mixture was stirred at room temperature for 5 h then partitioned between water and methylene chloride. The aqueous layer was extracted with methylene chloride. The organic layers were dried over anhydrous sodium sulfate and concentrated in vacuo to dryness to afford 3-cyano-5-methoxymethyl-benzoic acid (90 mg, 64%).

To a solution of 3-cyano-5-methoxymethyl-benzoic acid (90 mg, 0.469 mmol) in acetonitrile (3 mL) was added cesium carbonate (199 mg, 0.1 mmol) and ethyl iodide (44 μL, 0.563 mmol), respectively. The reaction mixture was stirred at reflux for 4 h. Upon cooling to room temperature, the reaction mixture was filtered and the filtrated was concentrated in vacuo. The residue was taken up in ethyl acetate and washed with water, brine and dried over anhydrous sodium sulfate. The solid was then filtered off, and the filtrate was concentrated in vacuo to afford ethyl 3-cyano-5-methoxymethyl-benzoate (88 mg, 70%).

Hydrogen chloride gas was passed through a solution of ethyl 3-cyano-5-methoxymethyl-benzoate (300 mg, 1.368 mmol) in anhydrous ethanol (15 mL) at 0° C. After 3 h, hydrogen chloride gas was stopped and the reaction vessel was sealed with a septum. After stirring at room temperature overnight, the reaction vessel was cooled to 0° C. and the septum was removed. The solvent was evaporated in vacuo and the residue was triturated in diethyl ether to afford ethyl 3-ethoxycarbonimidoyl-5-methoxymethyl-benzoate (200 mg, 49%).

A reaction mixture of meso-1,2-bis-(4-chloro-phenyl)-ethane-1,2-diamine (100 mg, 0.356 mmol), ethyl 3-ethoxycarbonimidoyl-5-methoxymethyl-benzoate (118 mg, 0.391 mmol) in ethanol (5 mL) was heated at reflux for 5 h. The solvent was removed and the residue was taken up in methylene chloride. It was washed with 1 N sodium hydroxide solution (1 mL) and dried over anhydrous sodium sulfate. The solid was then filtered off, and the filtrate was concentrated in vacuo. The residue was purified by flash chromatography (Biotage system, KP-Sil™ 32–63 μm, 60 Å silica gel) eluting with 1% methanol in methylene chloride to afford 3-[4,5-bis-(4-chloro-phenyl)-4,5-dihydro-1H-imidazol-2-yl]-5-methoxymethyl-benzoic acid ethyl ester (157 mg, 91%). HR-MS (EI, m/z) calculated for $C_{26}H_{24}N_2O_3Cl_2$ [(M–2H)$^+$] 480.1007, observed 480.1004.

EXAMPLE 28

4,5-bis-(4-Chloro-phenyl)-2-(5-hydroxymethyl-2-methoxy-phenyl)-4,5-dihydro-1H-imidazole To a solution of 2-bromo-1-methoxy-4-methyl-benzene (10 g, 49.74 mmol) in pyridine (27 mL) and water (80 mL) at 75° C. was added potassium permanganate (25.39 g, 160.7 mmol) in several portions. The reaction mixture was heated at reflux for 24 h and stirred at room temperature for 2 d. The black solid was filtered off using Celite and washed with a copious amount of water. The filtrate was concentrated in vacuo (to remove pyridine) to afford about 100–200 mL of aqueous solution. After extraction with diethyl ether (2×50 mL), the aqueous solution was acidified with 1 N hydrogen chloride to precipitate out 3-bromo-4-methoxy-benzoic acid as a white solid (8.202 g, 71%).

To a solution of 3-bromo-4-methoxy-benzoic acid (8 g, 34.62 mmol) in diethyl ether (120 mL) cooled to 0° C. was added lithium aluminum hydride (1.49 g, 38.08 mmol) in several portions. At the end of addition, the reaction mixture was stirred at 0° C. for 15 min before the icebath was removed. The reaction was continued at room temperature for 12 h. It was cooled back to 0° C. and water (2–5 mL) was carefully added to quench the excess lithium aluminum hydride. Sodium hydroxide (5% solution, 5–10 mL) was then added and the layers were separated after 1 h of stirring. The product was extracted with diethyl ether (2×100 mL). The organic layers were washed with sodium bicarbonate solution (1×10 mL), brine (1×10 mL) and dried over anhydrous sodium sulfate. The solid was then filtered off, and the filtrate was concentrated in vacuo. Purification of the crude residue by flash chromatography (Biotage system, KP-Sil™ 32–63 μm, 60 Å silica gel) eluting with 40% ethyl acetate in hexanes yielded (3-bromo-4-methoxy-phenyl)-methanol as a white solid (6.262 g, 83%).

To a solution of (3-bromo-4-methoxy-phenyl)-methanol (1 g, 4.607 mmol) in dimethylformamide (10 mL) at room temperature was added zinc cyanide (324.5 mg, 2.764 mmol). The reaction mixture was degassed by passing argon through for 30 min before tetrakis(triphenylphosphine) palladium (319 mg, 0.276 mmol) was added. The reaction mixture was heated at 80° C. for 12 h and stirred at room temperature for 2 d. It was diluted with diethyl ether (50 mL) and washed with sodium bicarbonate solution, brine and dried over anhydrous sodium sulfate. The solid was then filtered off, and the filtrate was concentrated in vacuo. Purification of the crude residue by flash chromatography (Biotage system, KP-Sil™ 32–63 μm, 60 Å silica gel) eluting with 40% ethyl acetate in hexanes yielded 5-hydroxymethyl-2-methoxy-benzonitrile (385 mg, 51%) as a white solid.

Hydrogen chloride gas was passed through a solution of 5-hydroxymethyl-2-methoxy-benzonitrile (250 mg, 1.226 mmol) in anhydrous ethanol (25 mL) at room temperature. After 2 h, hydrogen chloride gas was stopped and the reaction vessel was sealed. After stirring at room temperature for 12 h, the reaction vessel was cooled to 0° C. and opened. The solvent was evaporated in vacuo to dryness to afford crude ethyl 5-hydroxymethyl-2-methoxy-benzimidate hydrochloride. meso-1,2-Bis-(4-chloro-phenyl)-ethane-1,2-diamine (200 mg, 0.711 mmol), triethylamine (145 µL, 1.422 mmol) and ethanol (10 mL) were added and the resulting mixture was heated at reflux for 12 h. The solvent was removed and the residue was taken up in methylene chloride (2 mL) and sodium bicarbonate solution (2 mL). The product was extracted with methylene chloride (2×30 mL). The organic layers were washed with brine (1×5 mL) and dried over anhydrous sodium sulfate. The solid was then filtered off, and the filtrate was concentrated in vacuo. The residue was purified by flash chromatography (Biotage system, KP-Sil™ 32–63 µm, 60 Å silica gel) eluting with 0–20% methanol in ethyl acetate to afford 4,5-bis-(4-chloro-phenyl)-2-(5-hydroxymethyl-2-methoxy-phenyl)-4,5-dihydro-1H-imidazole (17 mg, 6%). LR-MS (APCI): 427 [(M+H)$^+$].

EXAMPLE 29

4,5-bis-(4-Chloro-phenyl)-2-(5-ethoxymethyl-2-methoxy-phenyl)-4,5-dihydro-1H-imidazole To a solution of 5-hydroxymethyl-2-methoxy-benzonitrile (500 mg, 3.064 mmol) in toluene (10 mL) cooled to 0° C. was added thionyl chloride (338 µL, 4.596 mmol). The reaction mixture was heated at reflux for 3 h. The reaction mixture was concentrated in vacuo to afford 5-chloromethyl-2-methoxy-benzonitrile as a white solid (500 mg, 90%). The product was used without further purification.

To a solution of 5-chloromethyl-2-methoxy-benzonitrile (254 mg, 1.399 mmol) in ethanol (10 mL) was added potassium carbonate (387 mg, 2.798 mmol). The mixture was heated at reflux for 12 h. Upon cooling to room temperature, the solvent was removed. Water (2–5 mL) was added and the product was extracted with diethyl ether (2×20 mL). The organic layers were washed with brine (1×5 mL) and dried over anhydrous sodium sulfate. The solid was then filtered off, and the filtrate was concentrated in vacuo. Purification of the crude residue by flash chromatography (Biotage system, KP-Sil™ 32–63 µm, 60 Å silica gel) eluting with 20% ethyl acetate in hexanes yielded 5-ethoxymethyl-2-methoxy-benzonitrile (182 mg, 68%).

Hydrogen chloride gas was passed through a solution of 5-ethoxymethyl-2-methoxy-benzonitrile (181 mg, 0.947 mmol) in anhydrous ethanol (30 mL) at room temperature. After 2 h, hydrogen chloride gas was stopped and the reaction vessel was sealed. After stirring at room temperature for 12 h, the reaction vessel was cooled to 0° C. and opened. The solvent was evaporated in vacuo to dryness to afford crude ethyl 5-ethoxymethyl-2-methoxy-benzimidate hydrochloride. meso-1,2-Bis-(4-chloro-phenyl)-ethane-1,2-diamine (253 mg, 0.9 mmol), triethylamine (186 µL, 1.5 mmol) and ethanol (10 mL) were added and the resulting mixture was heated at reflux for 12 h. The solvent was removed and the residue was taken up in methylene chloride (2 mL) and sodium bicarbonate solution (2 mL). The product was extracted with methylene chloride (2×30 mL). The organic layers were washed with brine (1×5 mL) and dried over anhydrous sodium sulfate. The solid was then filtered off, and the filtrate was concentrated in vacuo. The residue was purified by flash chromatography (Biotage system, KP-Sil™ 32–63 µm, 60 Å silica gel) eluting with 70–100% ethyl acetate in hexanes to afford 4,5-bis-(4-chloro-phenyl)-2-(5-ethoxymethyl-2-methoxy-phenyl)-4,5-dihydro-1H-imidazole (136 mg, 33%). LR-MS (APCI): 455 [(M+H)$^+$].

EXAMPLE 30

4,5-bis-(4-Chloro-phenyl)-2-(2-methoxy-5-methoxymethyl-phenyl)-4,5-dihydro-1H-imidazole To a solution of (3-bromo-4-methoxy-phenyl)-methanol (500 mg, 2.304 mmol, example 28) in tetrahydrofuran (5 mL) cooled to 0° C. was added sodium hydride (70 mg, 2.765 mmol). After 5 min, methyl iodide (287 µL, 4.608 mmol) was added. The reaction was then stirred at room temperature for 30 min. Thin layer chromatography (KP-Sil™ 32–63 µm, 60 Å silica gel, 40% ethyl acetate in hexanes) showed a mixture of starting material and product (higher Rf spot). Additional sodium hydride (58 mg) and methyl iodide (0.287 µL) were added and the reaction mixture was stirred at room temperature for 12 h. Water (5 mL) was added to quench the excess sodium hydride and the product was extracted with diethyl ether (2×50 mL). The organic layers were washed with brine (1×5 mL) and dried over anhydrous sodium sulfate. The solid was then filtered off, and the filtrate was concentrated in vacuo. Purification of the crude residue by flash chromatography (Biotage system, KP-Sil™ 32–63 µm, 60 Å silica gel) eluting with 20% ethyl acetate in hexanes yielded 2-bromo-1-methoxy-4-methoxymethyl-benzene (467 mg, 88%).

To a solution of 2-bromo-1-methoxy-4-methoxymethyl-benzene (460 mg, 1.991 mmol) in dimethylformamide (5 mL) at room temperature was added zinc cyanide (140.3 mg, 1.195 mmol). The reaction mixture was degassed by passing argon through for 30 min before tetrakis(triphenylphosphine)palladium (138 mg, 0.119 mmol) was added. The reaction mixture was heated at 80° C. for 12 h and stirred at room temperature for 2 d. It was diluted with diethyl ether (50 mL) and washed with sodium bicarbonate solution, brine and dried over anhydrous sodium sulfate. The solid was then filtered off, and the filtrate was concentrated in vacuo. Purification of the crude residue by flash chromatography (Biotage system, KP-Sil™ 32–63 µm, 60 Å silica gel) eluting with 30% ethyl acetate in hexanes yielded 2-methoxy-5-methoxymethyl-benzonitrile (268 mg, 76%) as a clear oil.

Hydrogen chloride gas was passed through a solution of 2-methoxy-5-methoxymethyl-benzonitrile (235 mg, 1.326 mmol) in anhydrous ethanol (15 mL) at room temperature. After 2 h, hydrogen chloride gas was stopped and the reaction vessel was sealed. After stirring at room temperature for 12 h, the reaction vessel was cooled to 0° C. and opened. The solvent was evaporated in vacuo and the residue was triturated in diethyl ether to afford ethyl 2-methoxy-5-methoxymethyl-benzimidate hydrochloride (340 mg, 99%).

A reaction mixture of meso-1,2-bis-(4-chloro-phenyl)-ethane-1,2-diamine (281 mg, 1 mmol), ethyl 2-methoxy-5-methoxymethyl-benzimidate hydrochloride (340 mg, 1.309 mmol) and triethylamine (210 µL, 1.5 mmol) in ethanol (10 mL) was heated at reflux for 12 h. The solvent was removed and the residue was taken up in methylene chloride (2 mL) and sodium bicarbonate solution (2 mL). The product was extracted with methylene chloride (2×30 mL). The organic layers were washed with brine (1×5 mL) and dried over anhydrous sodium sulfate. The solid was then filtered off, and the filtrate was concentrated in vacuo. The residue was purified by flash chromatography (Biotage system, KP-Sil™ 32–63 µm, 60 Å silica gel) eluting with 70% ethyl acetate in hexanes to afford 4,5-bis-(4-chloro-phenyl)-2-(2-methoxy-5-methoxymethyl-phenyl)-4,5-dihydro-1H-imidazole (233 mg, 53%). LR-MS (APCI): 441 [(M+H)$^+$].

EXAMPLE 31

4-{3-[4,5-bis-(4-Chloro-phenyl)-4,5-dihydro-1H-imidazol-2-yl]-4-methoxy-benzyl}-morpholine To a solution of 5-chloromethyl-2-methoxy-benzonitrile (246 mg, 1.354 mmol, example 29) in tetrahydrofuran (10 mL) at room temperature was added morpholine (1.193 mL, 13.54 mmol). The reaction mixture was heated at reflux for 4 h. The reaction was concentrated in vacuo (with heating) to remove morpholine and tetrahydrofuran to afford 2-methoxy-5-morpholin-4-ylmethyl-benzonitrile as a yellow oil (311.2 mg, 99%). The crude product was used without further purification.

Hydrogen chloride gas was passed through a solution of 2-methoxy-5-morpholin-4-ylmethyl-benzonitrile (300 mg, 1.292 mmol) in anhydrous ethanol (30 mL) at room temperature. After 2 h, hydrogen chloride gas was stopped and the reaction vessel was sealed. After stirring at room temperature for 12 h, the reaction vessel was cooled to 0° C. and opened. The solvent was evaporated in vacuo to dryness to afford crude ethyl 2-methoxy-5-morpholin-4-ylmethyl-benzimidate hydrochloride. meso-1,2-Bis-(4-chloro-phenyl)-ethane-1,2-diamine (150 mg, 0.533 mmol), triethylamine (373 µL, 5 mmol) and ethanol (10 mL) were added and the resulting mixture was heated at reflux for 12 h. The solvent was removed and the residue was taken up in methylene chloride (2 mL) and sodium bicarbonate solution (2 mL). The product was extracted with methylene chloride (2×30 mL). The organic layers were washed with brine (1×5 mL) and dried over anhydrous sodium sulfate. The solid was then filtered off, and the filtrate was concentrated in vacuo. The residue was purified by flash chromatography (Biotage system, KP-Sil™ 32–63 µm, 60 Å silica gel) eluting with 0–20% methanol in ethyl acetate to afford 4-{3-[4,5-bis-(4-chloro-phenyl)-4,5-dihydro-1H-imidazol-2-yl]-4-methoxy-benzyl}-morpholine (164 mg, 62%). LR-MS (APCI): 496 [(M+H)$^+$].

EXAMPLE 32

4,5-bis-(4-Chloro-phenyl)-2-(5-ethoxymethyl-2,4-dimethoxy-phenyl)-4,5-dihydro-1H-imidazole To solution of 5-bromo-2,4-dihydroxy-benzoic acid (5 g, 21.46 mmol) in dimethylformamide (30 mL) were added dimethyl sulfate (5.413 g, 42.92 mmol) and potassium carbonate (8.907 g, 64.38 mmol). The reaction mixture was heated at 80–90° C. for 12 h. Upon cooling to room temperature, the white solid was filtered off and the filtrate was concentrated in vacuo. The product was extracted with diethyl ether (2×100 mL). The organic layers were washed with water (1×10 mL), brine (1×10 mL) and dried over anhydrous sodium sulfate. The solid was filtered off and the filtrate was concentrated in vacuo. Purification of the crude residue by flash chromatography (Biotage system, KP-Sil™ 32–63 µm, 60 Å silica gel) eluting with 20–30% ethyl acetate in hexanes yielded methyl 5-bromo-2,4-dimethoxy-benzoate as a white solid (5.137 g, 87%).

To a solution of methyl 5-bromo-2,4-dimethoxy-benzoate (5.137 g, 22.05 mmol) in tetrahydrofuran (60 mL) cooled to 0° C. was added lithium aluminum hydride (863 mg, 22.05 mmol) in several portions. At the end of addition, the reaction mixture was stirred at 0° C. for 15 min before the icebath was removed. The reaction was continued at room temperature for 48 h. It was cooled to 0° C. and water (~5 mL) was carefully added to quench the excess lithium aluminum hydride. Sodium hydroxide (5% solution, 20 mL) was then added and the layers were separated after 2 h of stirring. The product was extracted with diethyl ether (2×100 mL). The organic layers were washed with sodium bicarbonate solution (1×10 mL), brine (1×10 mL) and dried over anhydrous sodium sulfate. The solid was filtered off and the filtrate was concentrated in vacuo. Purification of the crude residue by flash chromatography (Biotage system, KP-Sil™ 32–63 µm, 60 Å silica gel) eluting with 40% ethyl acetate in hexanes yielded (5-bromo-2,4-dimethoxy-phenyl)-methanol as off-white solids (3.743 g, 81%).

To a solution of (5-bromo-2,4-dimethoxy-phenyl)-methanol (2.75 g, 11.13 mmol) in dimethylformamide (15 mL) at room temperature was added zinc cyanide (784 mg, 6.678 mmol). The reaction mixture was degassed by passing argon through for 2 h before tetrakis(triphenylphosphine) palladium (772 mg, 0.668 mmol) was added. The reaction mixture was heated at 90° C. for 12 h. After the reaction mixture was cooled to room temperature, it was diluted with diethyl ether (100 mL) and washed with sodium bicarbonate solution, brine and dried over anhydrous sodium sulfate. The solid was filtered off and the filtrate was concentrated in vacuo. Purification of the crude residue by flash chromatography (Biotage system, KP-Sil™ 32–63 µm, 60 Å silica gel) eluting with 40–50% ethyl acetate in hexanes yielded 5-hydroxymethyl-2,4-dimethoxy-benzonitrile as a white solid (1.089 g, 51%).

To a solution of 5-hydroxymethyl-2,4-dimethoxy-benzonitrile (218 mg, 1.128 mmol) in tetrahydrofuran (10 mL) cooled to 0° C. were sequentially added sodium hydride (34.2 mg, 1.354 mmol) and iodomethane (140 µL, 2.256 mmol). The icebath was removed after 5 min and the reaction mixture was stirred at room temperature under argon for 12 h. Water was added and the product was extracted with methylene chloride (2×15 mL). The organic layers were washed with brine (1×2 mL) and dried over anhydrous sodium sulfate. The solid was filtered off and the filtrate was concentrated in vacuo. Purification of the crude residue by flash chromatography (Biotage system, KP-Sil™ 32–63 µm, 60 Å silica gel) eluting with 40% ethyl acetate in hexanes yielded 2,4-dimethoxy-5-methoxymethyl-benzonitrile as a white solid (221 mg, 95%).

Hydrogen chloride gas was passed through a solution of 2,4-dimethoxy-5-methoxymethyl-benzonitrile (220 mg, 1.062 mmol) in anhydrous ethanol (5 mL) cooled to 0° C. After 1 h, hydrogen chloride gas was stopped and the reaction vessel was sealed with a stopper. The reaction mixture was stirred at room temperature for 12 h. It was cooled to 0° C. and the stopper was removed. The solvent was evaporated in vacuo to dryness and the residue was dissolved in ethanol (10 mL). meso-1,2-Bis-(4-chloro-phenyl)-ethane-1,2-diamine (278 mg, 0.989 mmol) and triethylamine (208 µL, 1.484 mmol) were added. The reaction mixture was heated at gentle reflux for 12 h. The solvent was removed in vacuo and the residue was partitioned between methylene chloride (2 mL) and sodium bicarbonate solution (2 mL). The layers were separated and the aqueous layer was extracted with methylene chloride (2×30 mL). The organic layers were washed with brine (1×5 mL) and dried over sodium sulfate. The solid was filtered off and the filtrate was concentrated in vacuo. Purification of the crude residue by flash chromatography (Biotage system, KP-Sil™ 32–63 µm, 60 Å silica gel) eluting with 70% ethyl acetate in hexanes yielded 4,5-bis-(4-chloro-phenyl)-2-(5-ethoxymethyl-2,4-dimethoxy-phenyl)-4,5-dihydro-1H-imidazole. LR-MS (APCI): 485 [(M+H)$^+$].

EXAMPLE 33

{3-[4,5-bis-(4-Chloro-phenyl)-4,5-dihydro-1H-imidazol-2-yl]-5-methoxy-phenyl}-methanol To a solution of 3-bromo-5-methoxy-phenyl-methanol (460 mg, 2.119 mmol, prepared according to the procedure reported by Claudi, F. et al. *J. Med. Chem.* 2000, 43, 599–608) in dimethylformamide (3 mL) at room temperature was added zinc cyanide (149 mg, 1.271 mmol). The reaction mixture was degassed by passing argon through for 30 min before tetrakis(triphenylphosphine)palladium (147 mg, 0.127 mmol) was added. The reaction mixture was heated at 100° C. for 12 h. It was diluted with diethyl ether and washed with sodium bicarbonate solution, brine and dried over anhydrous sodium sulfate. The solid was then filtered off, and the filtrate was concentrated in vacuo. Purification of the crude residue by flash chromatography (Biotage system, KP-Sil™ 32–63 µm, 60 Å silica gel) eluting with 40% ethyl acetate in hexanes yielded 3-hydroxymethyl-5-methoxy-benzonitrile as white solids (269 mg, 78%).

Hydrogen chloride gas was passed through a solution of 3-hydroxymethyl-5-methoxy-benzonitrile (265 mg, 1.624 mmol) in ethanol (10 mL) at 0° C. for 1 h. The reaction vessel was sealed with a Teflon stopper and stirred for 1 d at room temperature. The reaction vessel was cooled to 0° C. and the stopper was removed. The reaction mixture was concentrated in vacuo to dryness, then a solution of meso-1,2-bis-(4-chloro-phenyl)-ethane-1,2-diamine (457 mg, 1.624 mmol) and triethylamine (340 µL, 2.436 mmol) in ethanol (6 mL) was added. The mixture was heated at reflux for 12 h. The solvent was evaporated in vacuo and the residue was partitioned between ethyl acetate (10 mL) and sodium bicarbonate solution (3 mL). The layers were separated and the product was extracted with methylene chloride. The organic layers were washed with brine and dried over anhydrous magnesium sulfate. The solid was then filtered off, and the filtrate was concentrated in vacuo. Purification of the residue by flash chromatography (Biotage system, KP-Sil™ 32–63 µm, 60 Å silica gel) eluting with ethyl acetate yielded {3-[4,5-bis-(4-chloro-phenyl)-4,5-dihydro-1H-imidazol-2-yl]-5-methoxy-phenyl}-methanol as an off-white solid (415 mg, 60%). HR-MS (ES, m/z) calculated for $C_{23}H_{21}N_2O_2Cl_2$ [(M+H)$^+$] 427.0975, observed 427.0978.

EXAMPLE 34

4,5-bis-(4-Chloro-phenyl)-2-(3-methoxy-5-methoxymethyl-phenyl)-4,5-dihydro-1H-imidazole To a solution of 3-hydroxymethyl-5-methoxy-benzonitrile (261.1 mg, 1.6 mmol, example 33) in tetrahydrofuran (5 mL) cooled to 0° C. was added sodium hydride (43 mg, 1.68 mmol). The ice-bath was removed and the reaction mixture was stirred at room temperature for 15 min before methyl iodide (149 µL, 2.4 mmol) was added. The reaction mixture was stirred at room temperature for 3 h before being quenched with several drops of saturated ammonium chloride solution. The solvent was removed and the residue was taken up in diethyl ether. The organic layer was washed with brine and dried over anhydrous sodium sulfate. The solid was then filtered off, and the filtrate was concentrated in vacuo. Purification of the residue by flash chromatography (Biotage system, KP-Sil™ 32–63 µm, 60 Å silica gel) eluting with 12% ethyl acetate in hexanes yielded 3-methoxy-5-methoxymethyl-benzonitrile as a colorless oil (213 mg, 75%).

Hydrogen chloride gas was passed through a solution of 3-methoxy-5-methoxymethyl-benzonitrile (213 mg, 1.2 mmol) in ethanol (10 mL) at 0° C. for 1 h. The reaction vessel was sealed with a Teflon stopper and stirred for 1 d at room temperature. The reaction vessel was cooled to 0° C. and the stopper was removed. The reaction mixture was concentrated in vacuo to dryness, then a solution of meso-1,2-bis-(4-chloro-phenyl)-ethane-1,2-diamine (346 mg, 1.232 mmol) and triethylamine (259 µL, 1.848 mmol) in ethanol (6 mL) was added. The mixture was heated at reflux for 12 h. The solvent was evaporated in vacuo and the residue was partitioned between ethyl acetate and sodium bicarbonate solution. The layers were separated and the product was extracted with ethyl acetate. The organic layers were washed with brine and dried over anhydrous magnesium sulfate. The solid was then filtered off, and the filtrate was concentrated in vacuo. Purification of the residue by flash chromatography (Biotage system, KP-Sil™ 32–63 µm, 60 Å silica gel) eluting with 75% ethyl acetate in hexanes yielded 4,5-bis-(4-chloro-phenyl)-2-(3-methoxy-5-methoxymethyl-phenyl)-4,5-dihydro-1H-imidazole (244 mg, 45%). HR-MS (ES, m/z) calculated for $C_{24}H_{23}N_2O_2Cl_2$ [(M+H)$^+$] 441.1131, observed 441.1135.

EXAMPLE 35

{3-[4,5-bis-(4-Chloro-phenyl)-4,5-dihydro-1H-imidazol-2-yl]-5-methoxymethyl-phenyl}-methanol To a solution of 5-bromo-isophthalic acid dimethyl ester (4.54 g, 16.63 mmol) in methylene chloride (50 mL) cooled to 0° C. under argon was added diisobutylaluminum hydride (80 mL, 80 mmol, 1 M in toluene) via syringe. The reaction was quenched by Rochelle salt solution after 1 h of stirring at 0° C. The biphasic mixture was then stirred at room temperature for 12 h before work-up. The product was extracted with diethyl ether (2×50 mL). The organic layers were washed with water, brine and dried over anhydrous sodium sulfate. The solid was then filtered off, and the filtrate was concentrated in vacuo to afford (3-bromo-5-hydroxymethyl-phenyl)-methanol as a white solid (3.582 g, 99%).

To a solution of (3-bromo-5-hydroxymethyl-phenyl)-methanol (3.582 g, 16.50 mmol) in methylene chloride (40 mL) was added triethylamine (2.774 mL, 19.80 mmol), tert-butyldimethylsilyl chloride (2.820 g, 18.15 mmol), dimethylaminopyridine (100.8 mg, 0.825 mmol), respectively. The reaction mixture was stirred at room temperature for 12 h. Water was added, and the product was extracted with diethyl ether. The organic layers were washed with brine and dried over anhydrous sodium sulfate. The solid was then filtered off, and the filtrate was concentrated in vacuo to afford a mixture of [3-bromo-5-(tert-butyl-dimethyl-silanyloxymethyl)-phenyl]-methanol, 1-bromo-3,5-bis-(tert-butyl-dimethyl-silanyloxymethyl)-benzene and (3-bromo-5-hydroxymethyl-phenyl)-methanol. Yield: 5.828 g To a solution of the mixture of [3-bromo-5-(tert-butyl-dimethyl-silanyloxymethyl)-phenyl]-methanol, 1-bromo-3,5-bis-(tert-butyl-dimethyl-silanyloxymethyl)-benzene and (3-bromo-5-hydroxymethyl-phenyl)-methanol (5.828 g) in tetrahydrofuran (20 mL) cooled to 0° C. was added sodium hydride (422.2 mg, 17.59 mmol). After 15 min at 0° C., iodomethane (2.190 mL, 35.18 mmol) was added via syringe and the icebath was removed. The reaction was quenched after 45 min of stirring at room temperature by addition of saturated ammonium chloride solution. The product was extracted with diethyl ether (2×30 mL). The organic layers were washed with water (1×10 mL), brine (1×10 mL) and dried over anhydrous sodium sulfate. The solid was then filtered off, and the filtrate was concentrated in vacuo. Purification of the crude residue by flash chromatography (Biotage system, KP-Sil™ 32–63 µm, 60 Å silica gel) eluting with 5–10% ethyl acetate in hexanes yielded 1-bromo-3,5-bis-(tert-butyl-dimethyl-silanyloxymethyl)- benzene (2.165 g), (3-bromo-5-methoxymethyl-benzyloxy)-tert-butyl-dimethyl-silane (2.1 g), and 1-bromo-3,5-bis-methoxymethyl-benzene (433 mg).

To a solution of (3-bromo-5-methoxymethyl-benzyloxy)-tert-butyl-dimethylsilane (2.1 g, 6.081 mmol) in dimethylformamide (10 mL) at room temperature was added zinc cyanide (428.4 mg, 3.649 mmol). The reaction mixture was degassed by passing argon through for 2 h before tetrakis (triphenylphosphine)palladium (422 mg, 0.365 mmol) was added. The reaction mixture was heated at 80° C. under argon for 8 h. The reaction mixture was taken up in diethyl ether and washed with ammonium hydroxide, brine and dried over anhydrous sodium sulfate. The solid was then filtered off, and the filtrate was concentrated in vacuo. Purification of the crude residue by flash chromatography (Biotage system, KP-Sil™ 32–63 μm, 60 Å silica gel) eluting with 5–10% ethyl acetate in hexanes yielded 3-(tert-butyl-dimethylsilanyloxymethyl)-5-methoxymethyl-benzonitrile (1.402 g, 79%).

To a solution of 3-(tert-butyl-dimethyl-silanyloxymethyl)-5-methoxymethyl-benzonitrile (1.402 g, 4.810 mmol) in tetrahydrofuran (10 mL) at room temperature was added tetrabutylammonium fluoride (5.051 mL, 5.051 mmol, 1 M in tetrahydrofuran). The reaction mixture was stirred at room temperature for 2 h then concentrated in vacuo. Purification of the residue by flash chromatography (Biotage system, KP-Sil™ 32–63 μm, 60 Å silica gel) eluting with 40% ethyl acetate in hexanes yielded 3-hydroxymethyl-5-methoxymethyl-benzonitrile (713 mg, 84%).

Hydrogen chloride gas was passed through a solution of 3-hydroxymethyl-5-methoxymethyl-benzonitrile (720 mg, 4.063 mmol) in anhydrous ethanol (25 mL) at 0° C. After 1 h, hydrogen chloride gas was stopped and the reaction vessel was sealed with a septum. After stirring at room temperature for 1 d, the reaction vessel was cooled to 0° C. and the septum was removed. The solvent was evaporated in vacuo to afford ethyl 3-hydroxymethyl-5-methoxymethyl-benzimidate hydrochloride as a white solid (1.05 g, 100%).

A solution of meso-1,2-bis-(4-chloro-phenyl)-ethane-1,2-diamine (82 mg, 0.291 mmol), ethyl 3-hydroxymethyl-5-methoxymethyl-benzimidate hydrochloride (63 mg, 0.243 mmol) in ethanol (5 mL) was heated at reflux for 6 h. The solvent was removed and the residue was taken up in methylene chloride. It was washed with sodium bicarbonate solution, water, brine and dried over anhydrous sodium sulfate. The residue was purified by flash chromatography (Biotage system, KP-Sil™ 32–63 μm, 60 Å silica gel) eluting with 1–4% methanol in ethyl acetate to afford {3-[4,5-bis-(4-chloro-phenyl)-4,5-dihydro-1H-imidazol-2-yl]-5-methoxymethyl-phenyl}-methanol as an off-white foam (45 mg, 42%). HR-MS (EI, m/z) calculated for $C_{24}H_{22}N_2O_2Cl_2$ (M$^+$) 440.1058, observed 440.1054.

EXAMPLE 36

{3-[5-(4-Chloro-phenyl)-4-(4-nitro-phenyl)-4,5-dihydro-1H-imidazol-2-yl]-5-methoxymethyl-phenyl}-methanol was prepared from 3-hydroxymethyl-5-methoxymethyl-benzonitrile and 1-(4-chloro-phenyl)-2-(4-nitro-phenyl)-ethane-1,2-diamine in an analogous manner as described in example 35. LR-MS (ES): 452 [(M+H)$^+$], 493 [(M+H+CH$_3$CN)$^+$].

EXAMPLE 37

2-(3,5-bis-Methoxymethyl-phenyl)-4,5-bis-(4-chloro-phenyl)-4,5-dihydro-1H-imidazole To a solution of (3-bromo-5-hydroxymethyl-phenyl)-methanol (500 mg, 2.304 mmol, example 35) in tetrahydrofuran (12 mL) cooled to 0° C. was added sodium hydride (125 mg, 4.954 mmol). After 15 min, methyl iodide (430 μL, 6.912 mmol) was added. The reaction was then stirred at room temperature for 12 h. The solvent was removed in vacuo and the residue was taken in ethyl acetate (20 mL) and water (30 mL). The layers were separated and the product was extracted with ethyl acetate (2×20 mL). The organic layers were washed with brine (1×5 mL) and dried over anhydrous magnesium sulfate. The solid was then filtered off, and the filtrate was concentrated in vacuo to afford 1-bromo-3,5-bis-methoxymethyl-benzene (522 mg, 92%). It was used without further purification.

To a solution of 1-bromo-3,5-bis-methoxymethyl-benzene (522 mg, 2.130 mmol) in dimethylformamide (5 mL) at room temperature was added zinc cyanide (150 mg, 1.278 mmol). The reaction mixture was degassed by passing argon through for I h before tetrakis(triphenylphosphine) palladium (148 mg, 0.128 mmol) was added. The reaction mixture was heated at 80° C. under argon for 12 h. The reaction mixture was taken up in toluene (30 mL) and washed with 10% ammonium hydroxide (2×40 mL), brine and dried over anhydrous magnesium sulfate. The solid was then filtered off, and the filtrate was concentrated in vacuo. Purification of the crude residue by flash chromatography (Biotage system, KP-Sil™ 32–63 μm, 60 Å silica gel) eluting with 20% ethyl acetate in hexanes yielded 3,5-bis-methoxymethyl-benzonitrile (320 g, 79%).

Hydrogen chloride gas was passed through a solution of 3,5-bis-methoxymethyl-benzonitrile (1 g, 5.2 mmol) in anhydrous ethanol (150 mL) at room temperature. After 5.5 h, hydrogen chloride gas was stopped. The solvent was evaporated in vacuo and the residue was triturated in diethyl ether to afford ethyl 3,5-bis-methoxymethyl-benzimidate hydrochloride (658 mg, 46%). It was used without further purification.

A solution of meso-1,2-bis-(4-chloro-phenyl)-ethane-1,2-diamine (50 mg, 0.178 mmol), ethyl 3,5-bis-methoxymethyl-benzimidate hydrochloride (58 mg, 0.213 mmol) in ethanol (5 mL) was heated at reflux for 5 h. The solvent was removed and the residue was taken up in methylene chloride. It was washed with 1 N sodium hydroxide and dried over anhydrous sodium sulfate. The solid was filtered off and the filtrate was concentrated in vacuo. The residue was purified by flash chromatography (Biotage system, KP-Sil™ 32–63 μm, 60 Å silica gel) eluting with 0.5–4% methanol in methylene chloride to afford 2-(3,5-bis-methoxymethyl-phenyl)-4,5-bis-(4-chloro-phenyl)-4,5-dihydro-1H-imidazole (54 mg, 67%). HR-MS (EI, m/z) calculated for $C_{25}H_{24}N_2O_2Cl_2$ (M$^+$) 454.1207, observed 454.1215.

EXAMPLE 38

{3-[4,5-bis-(4-Chloro-phenyl)-4,5-dihydro-1H-imidazol-2-yl]-5-hydroxymethyl-phenyl}-methanol To a solution of 1-bromo-3,5-bis-(tert-butyl-dimethyl-silanyloxymethyl)-benzene (2.05 g, 4.601 mmol, example 35) in dimethylformamide (8 mL) at room temperature was added zinc cyanide (324 mg, 2.761 mmol). The reaction mixture was degassed by passing argon through for 1 h before tetrakis(triphenylphosphine)palladium (319 mg, 0.276 mmol) was added. The reaction mixture was heated at 80° C. under argon for 12 h. The reaction mixture was taken up in toluene (40 mL) and washed with 2 N ammonium hydroxide (2×40 mL), brine and dried over anhydrous magnesium sulfate. The solid was then filtered off, and the filtrate was concentrated in vacuo. Purification of the crude residue by flash chromatography (Biotage system, KP-Sil™ 32–63 μm, 60 Å silica gel) eluting with 5% ethyl acetate in hexanes yielded 3,5-bis-(tert-butyl-dimethyl-silanyloxymethyl)-benzonitrile (1.47 g, 82%).

To a solution of 3,5-bis-(tert-butyl-dimethyl-silanyloxymethyl)-benzonitrile (1.45 g, 3.702 mmol) in tetrahydrofuran (30 mL) at room temperature was added tetrabutylammonium fluoride (9.255 mL, 9.255 mmol, 1 M in tetrahydrofuran). The reaction mixture was stirred at room temperature for 2 h then concentrated in vacuo. The residue was partitioned between ethyl acetate (20 mL) and water (30 mL). The layers were separated and the product was extracted with ethyl acetate (3×20 mL). The organic layers were washed with brine and dried over anhydrous magnesium sulfate. The solid was filtered off, and the filtrate was concentrated in vacuo. Purification of the residue by flash chromatography (Biotage system, KP-Sil™ 32–63 μm, 60 Å silica gel) eluting with 75% ethyl acetate in hexanes yielded 3,5-bis-hydroxymethyl-benzonitrile (465 mg, 77%).

Hydrogen chloride gas was passed through a solution of 3,5-bis-hydroxymethyl-benzonitrile (50 mg, 0.23 mmol) in anhydrous ethanol (100 mL) at room temperature. After 5 h, hydrogen chloride gas was stopped. The solvent was evaporated in vacuo and the residue was triturated in diethyl ether to afford ethyl 3,5-bis-hydroxymethyl-benzimidate hydrochloride (52 mg, 92%). It was used without further purification.

A solution of meso-1,2-bis-(4-chloro-phenyl)-ethane-1,2-diamine (50 mg, 0.178 mmol), ethyl 3,5-bis-hydroxymethyl-benzimidate hydrochloride (52 mg, 0.213 mmol) in ethanol (5 mL) was heated at reflux for 5 h. The solvent was removed and the residue was taken up in methylene chloride. It was washed with 1 N sodium hydroxide and dried over anhydrous sodium sulfate. The solid was filtered off and the filtrate was concentrated in vacuo. The residue was purified by flash chromatography (Biotage system, KP-Sil™ 32–63 μm, 60 Å silica gel) eluting with 10% methanol in methylene chloride to afford {3-[4,5-bis-(4-chloro-phenyl)-4,5-dihydro-1H-imidazol-2-yl]-5-hydroxymethyl-phenyl}-methanol (7 mg, 10%). HR-MS (EI, m/z) calculated for $C_{23}H_{18}N_2O_2Cl_2$ [(M–2H)$^+$] 424.0745, observed 424.0749.

EXAMPLE 39

Sodium {2-[4,5-bis-(4-Chloro-phenyl)-4,5-dihydro-1H-imidazol-2-yl]-phenoxy}-acetate {2-[4,5-Bis-(4-chloro-phenyl)-4,5-dihydro-1H-imidazol-2-yl]-phenoxy)-acetic acid ethyl ester (35 mg, 0.075 mmol) was dissolved in 1.5 mL of dioxane, and 0.5 M sodium hydroxide solution (1.5 mL, 0.75 mmol) was added. The reaction mixture was stirred at room temperature for 23 h. The reaction mixture was concentrated in vacuo and the residue was purified by flash chromatography (Biotage system, 12S-C18 reverse phase) eluting with 0–25% acetonitrile in water to afford sodium {2-[4,5-bis-(4-chloro-phenyl)-4,5-dihydro-1H-imidazol-2-yl]-phenoxy}-acetate (22 mg, 63%). HR-MS (ES, m/z) calculated for $C_{23}H_{19}N_2O_3Cl_2$ [(M–Na+2H)$^+$] 441.0767, observed 441.0767.

EXAMPLE 40

In an analogous manner as described in Example 39, there were obtained:

a. Sodium{4-[4,5-bis-(4-chloro-phenyl)-4,5-dihydro-1H-imidazol-2-yl]-phenoxy}-acetate (43%) from {4-[4,5-bis-(4-chloro-phenyl)-4,5-dihydro-1H-imidazol-2-yl]-phenoxy}-acetic acid ethyl ester (example 8). HR-MS (ES, m/z) calculated for $C_{23}H_{19}N_2O_2Cl_2$ [(M+H)$^+$] 441.0768, observed 441.0772.

b. Sodium 3-[4,5-bis-(4-chloro-phenyl)-4,5-dihydro-1H-imidazol-2-yl]-benzoate (36%) from 3-[4,5-bis-(4-chloro-phenyl)-4,5-dihydro-1H-imidazol-2-yl]-benzoic acid ethyl ester (example 2f). HR-MS (EI, m/z) calculated for $C_{22}H_{14}N_2O_2Cl_2$ [(M–HNa)$^+$] 408.0432, observed 408.0438.

c. Sodium 3-[4,5-bis-(4-chloro-phenyl)-4,5-dihydro-1H-imidazol-2-yl]-5-methoxymethyl-benzoate (75%) from 3-[4,5-bis-(4-chloro-phenyl)-4,5-dihydro-1H-imidazol-2-yl]-5-methoxymethyl-benzoic acid ethyl ester (example 27). HR-MS (ES, m/z) calculated for $C_{24}H_{21}N_2O_3Cl_2$ [(M–Na+2H)$^+$] 455.0929, observed 455.0925.

d. Sodium {3-[4,5-bis-(4-chloro-phenyl)-4,5-dihydro-1H-imidazol-2-yl]-5-methoxy-phenoxy}-acetate (34%) from {3-[4,5-bis-(4-chloro-phenyl)-4,5-dihydro-1H-imidazol-2-yl]-5-methoxy-phenoxy}-acetic acid ethyl ester (example 9d). HR-MS (ES, m/z) calculated for $C_{24}H_{21}N_2O_4Cl_2$ [(M–Na+2H)$^+$] 471.0874, observed 471.0875.

e. Sodium 3-[4,5-bis-(4-chloro-phenyl)-4,5-dihydro-1H-imidazol-2-yl]-4-methoxy-benzoate (61%) from 3-[4,5-bis-(4-chloro-phenyl)-4,5-dihydro-1H-imidazol-2-yl]-4-methoxy-benzoic acid ethyl ester (example 2x). HR-MS (ES, m/z) calculated for $C_{23}H_{19}N_2O_3Cl_2$ [(M–Na+2H)$^+$] 441.0767, observed 441.0771.

EXAMPLE 41

4,5-bis-(4-Chloro-phenyl)-2-o-tolyl-4,5-dihydro-1H-imidazole

To a degassed suspension of o-toluamide (1.35 g, 9.788 mmol) in methylene chloride (5 mL) was added triethyloxonium tetrafluoroborate (9.788 mL, 9.788 mmol, 1 M in methylene chloride). After the clear solution was stirred at room temperature overnight, it was concentrated in vacuo. The residue was triturated in methylene chloride and diethyl ether. The white solid was filtered off and washed with diethyl ether to afford ethyl 2-methyl-benzimidate tetrafluoroborate (1.4 g, 80%). It was used without further purification.

A reaction mixture of meso-1,2-bis-(4-chloro-phenyl)-ethane-1,2-diamine (200 mg, 0.71 1 mmol) and ethyl 2-methyl-benzimidate tetrafluoroborate (134 mg, 0.711 mmol) in ethanol (2 mL) was heated at 85° C. for 12 h. The reaction mixture was concentrated in vacuo and the residue was purified by flash chromatography (Biotage system, KP-Sil™ 32–63 μm, 60 Å silica gel) eluting with 0%, 25%, 50%, 100% diethyl ether in methylene chloride to afford 4,5-bis-(4-chloro-phenyl)-2-o-tolyl-4,5-dihydro-1H-imidazolea sa white solid (106 mg, 39%). HR-MS (ES, m/z) calculated for $C_{22}H_{19}N_2Cl_2$ [(M+H)$^+$] 381.0920, observed 381.0925.

EXAMPLE 42

{2-[4,5-bis-(4-Chloro-phenyl)-4,5-dihydro-1H-imidazol-2-yl]-phenyl}-dimethyl-amine A solution of methyl 2-dimethylamino-benzoate (1.79 g, 10 mmol) in 2 M ammonia in methanol (20 mL) was heated at 80° C. in a sealed reaction vessel for 3 d. Upon cooling to room temperature, it was diluted with water. The product was extracted with diethyl ether. The ethereal extracts were washed with brine and dried over anhydrous magnesium sulfate. The solid was then filtered off, and the filtrate was concentrated in vacuo. Purification of the residue by flash chromatography (Biotage system, KP-Sil™ 32–63 μm, 60 Å silica gel) eluting with 20% ethyl acetate in hexanes yielded 2-dimethylamino-benzamide (85 m g, 5%).

To a solution of 2-dimethylamino-benzamide (85 mg, 0.52 mmol) in diethyl ether (2 mL) was added triethyloxonium tetrafluoroborate (0.52 mL, 0.52 mmol, 1 M in methylene chloride). The reaction mixture was stirred at room temperature overnight and concentrated to dryness. A solution of meso-1,2-bis-(4-chloro-phenyl)-ethane-1,2-diamine (114 mg, 0.405 mmol) in ethanol (2 mL) was added. The reaction mixture was heated at reflux for 3 h and worked up with sodium bicarbonate solution and methylene chloride. The organic extracts were dried over anhydrous sodium sulfate and concentrated in vacuo. The residue was purified by flash chromatography (Biotage system, KP-Sil™ 32–63 μm, 60 Å silica gel) eluting with 1–2% methanol in diethyl ether to afford {2-[4,5-bis-(4-chloro-phenyl)-4,5-dihydro-1H-imidazol-2-yl]-phenyl}-dimethyl-amine (66 mg, 31%). HR-MS (ES, m/z) calculated for $C_{23}H_{21}N_3Cl_2$ $(M^+)$ 410.1186, observed 410.1189.

EXAMPLE 43

4,5-bis-(4-Chloro-phenyl)-2-(2-ethoxy-6-methoxyphenyl)-4,5-dihydro-1H-imidazole

To a solution of 2,6-dihydroxybenzamide (2 g, 12.66 mmol) in dimethylformamide (100 mL) were added cesium carbonate (3.922 g, 12.03 mmol) and methyl iodide (756 μL, 12.03 mmol). The reaction mixture was stirred at room temperature for 36 h and was taken in 200 mL of ethyl acetate and diethyl ether (1:1 ratio). It was washed with water, brine and dried over anhydrous sodium sulfate. The solid was then filtered off, and the filtrate was concentrated in vacuo. Purification of the residue by flash chromatography (Biotage system, KP-Sil™ 32–63 μm, 60 Å silica gel) eluting with 25% ethyl acetate in hexanes yielded 2-hydroxy-6-methoxy-benzamide (1.4 g, 66%).

To a solution of 2-hydroxy-6-methoxy-benzanide (500 mg, 2.991 mmol) in dimethylformamide (50 mL) were added cesium carbonate (1.463 g, 4.487 mmol) and ethyl iodide (364 μL, 4.487 mmol). The reaction mixture was stirred at room temperature for 24 h and was taken in 100 mL of ethyl acetate and diethyl ether (1:1 ratio). It was washed with water, brine and dried over anhydrous sodium sulfate. The solid was then filtered off, and the filtrate was concentrated in vacuo Purification of the residue by flash chromatography (Biotage system, KP-Sil™ 32–63 μm, 60 Å silica gel) eluting with 10% ethyl acetate in hexanes yielded 2-ethoxy-6-methoxy-benzamide (222 mg, 38%).

To a degassed solution of 2-ethoxy-6-methoxybenzamide (222 mg, 1.137 mmol) in methylene chloride (4 mL) was added triethyloxonium tetrafluoroborate (1.137 mL, 1.137 mmol, 1 M in methylene chloride). The reaction mixture was stirred at room temperature overnight and concentrated to dryness. meso-1,2-Bis-(4-chloro-phenyl)-ethane-1,2-diamine (141 mg, 0.503 mmol) and ethanol (10 mL) were added. The re action mixture was heated at reflux for 17 h. Upon cooling to room temperature, the solvent was removed in vacuo. The residue was taken in methylene chloride and washed with sodium bicarbonate solution, water, brine and dried over anhydrous sodium sulfate. The solid was then filtered off, and the filtrate was concentrated in vacuo. The residue was purified by flash chromatography (Biotage system, KP-Sil™ 32–63 μm, 60 Å silica gel) eluting with 2–12% methanol in methylene chloride to afford 4,5-bis-(4-chloro-phenyl)-2-(2-ethoxy-6-methoxyphenyl)-4,5-dihydro-1H-imidazole (28 mg, 16%). HR-MS (ES, m/z) calculated for $C_{24}H_{23}N_2O_2Cl_2$ $[(M+H)^+]$ 441.1131, observed 441.1134.

EXAMPLE 44

4,5-bis-(4-Chloro-phenyl)-2-(2,6-dimethoxyphenyl)-4,5-dihydro-1H-imidazole, Trifluoroacetic Acid Salt A mixture of 2,6-dimethoxy-benzoic acid (1.295 g, 7.110 mmol) and meso-1,2-bis-(4-chloro-phenyl)-ethane-1,2-diamine (200 mg, 0.711 mmol) in ethanol was heated in the pressure tube at 100° C. for 3 d. The yellow mixture was transferred to a round-bottom flask and ethanol was removed. The residue was taken up in methylene chloride (10 mL) and saturated sodium carbonate solution (5 mL). The product was extracted with methylene chloride (2×10 mL). The organic layers were washed with saturated sodium carbonate solution (1×5 mL), brine (1×5 mL) and dried over anhydrous sodium sulfate. The solid was then filtered off, and the filtrate was concentrated in vacuo. The crude residue was passed through a Biotage column (Biotage system, KP-Sil™ 32–63 μm, 60 Å silica gel) eluting with 0–5% methanol in ethyl acetate to afford a mixture of 4,5-bis-(4-chloro-phenyl)-2-(2,6-dimethoxy-phenyl)-4,5-dihydro-1H-imidazole and meso-1,2-bis-(4-chloro-phenyl)-ethane-1,2-diamine (~236 mg, yellow solids). HPLC purification (C18, 5–95% acetonitrile in water) of the mixture yielded 4,5-bis-(4-chloro-phenyl)-2-(2,6-dimethoxy-phenyl)-4,5-dihydro-1H-imidazole as a white solid (13 mg, 4%). HR-MS (ES, m/z) calculated for $C_{23}H_{21}N_2O_2Cl_2$ $[(M+H)^+]$ 427.0975, observed 427.0981.

EXAMPLE 45

2-(4-Chloro-2-isopropoxy-phenyl)-4,5-bis-(4-chlorophenyl)-4,5-dihydro-1-imidazole was prepared from 4-chloro-2-fluoro-benzonitrile and meso-1,2-bis-(4-chlorophenyl)ethane-1,2-diamine in an analogous manner as described in example 14. HR-MS (ES, m/z) calculated for $C_{24}H_{22}N_2OCl_3$ $[(M+H)^+]$ 459.0792, observed 459.0797.

EXAMPLE 46

2-(5-Chloro-2-isopropoxy-phenyl)-4,5-bis-(4-chlorophenyl)-4,5-dihydro-1H-imidazole was prepared from meso-1,2-bis-(2-hydroxy-phenyl)-ethane-1,2-diamine and 2-bromo-4-chloro-phenol in an analogous manner as described in example 10. HR-MS (ES, m/z) calculated for $C_{24}H_{22}N_2OCl_3$ $[(M+H)^+]$ 459.0792, observed 459.0795.

EXAMPLE 47

In an analogous manner as described in example 18, there were obtained:
a. 4,5-Bis-(4-chloro-phenyl)-2-[4-methoxy-2-(2,2,2-trifluoro-ethoxy)-phenyl]-4,5-dihydro-1H-imidazole from 2-hydroxy-4-methoxy-benzaldehyde and meso-1,2-bis-(4-chloro-phenyl)-ethane-1,2-diamine. HR-MS (ES, m/z) calculated for $C_{24}H_{20}N_2O_2F_3Cl_2$ $[(M+H)^+]$ 495.0849, observed 495.0854.
b. 4,5-Bis-(4-bromo-phenyl)-2-[4-methoxy-2-(2,2,2-trifluoro-ethoxy)-phenyl]-4,5-dihydro-1H-imidazole from 2-hydroxy-4-methoxy-benzaldehyde and meso-1, 2-bis-(4-bromo-phenyl)-ethane-1,2-diamine. HR-MS (ES, m/z) calculated for $C_{24}H_{20}N_2O_2F_3Br_2$ $[(M+H)^+]$ 582.9838, observed 582.9847.

c. 2-{2-[4,5-Bis-(4-chloro-phenyl)-4,5-dihydro-1H-imidazol-2-yl]-5-methoxy-phenoxy}-propan-1-ol from 2-hydroxy-4-methoxy-benzaldehyde and meso-1,2-bis-(4-chloro-phenyl)-ethane-1,2-diamine. HR-MS (ES, m/z) calculated for $C_{25}H_{25}N_2O_3Cl_2$ $[(M+H)^+]$ 471.1237, observed 471.1236.

d. 4,5-Bis-(4-ethynyl-phenyl)-2-(2-isopropoxy-4-methoxy-phenyl)-4,5-dihydro-1H-imidazole from 2-hydroxy-4-methoxy-benzaldehyde and meso-1,2-bis-(4-ethynyl-phenyl)-ethane-1,2-diamine (prepared according to the procedure described by Jennerwein, M. et al. Cancer Res. Clin. Oncol. 1988, 114, 347–58; Vogtle, F.; Goldschmitt, E. Chem. Ber. 1976, 109, 1–40). HR-MS (ES, m/z) calculated for $C_{29}H_{27}N_2O_2$ $[(M+H)^+]$ 435.2067, observed 435.2071.

e. 4-(4-Chloro-phenyl)-5-(4-ethynyl-phenyl)-2-(2-isopropoxy-4-methoxy-phenyl)-4,5-dihydro-1H-imidazole from 2-hydroxy-4-methoxy-benzaldehyde and 1-(4-chloro-phenyl)-2-(4-ethynyl-phenyl)-ethane-1,2-diamine (prepared from meso-1,2-bis-(2-hydroxy-phenyl)-ethane-1,2-diamine in an analogous manner as described in example 3). HR-MS (ES, m/z) calculated for $C_{27}H_{26}N_2O_2Cl$ $[(M+H)^+]$ 445.1678, observed 445.1682.

EXAMPLE 48

In Vitro Activity Assay

The ability of the compounds to inhibit the interaction between p53 and MDM2 proteins was measured by an ELISA (Enzyme-Linked Immuno Sorbent Assay) in which recombinant GST-tagged MDM2 binds to a peptide that resembles the MDM2-interacting region of p53 (Böttger et al., J. Mol. Bio. 1997, Vol. 269, pgs. 744–756). This peptide is immobilized to the surface of a 96 well plate via N-terminal biotin which binds to streptavidin-coated wells. MDM2 is added to each well in the presence of anti-MDM2 mouse monoclonal antibody (SMP-14, Santa Cruz Biotech). After removal of the unbound MDM2 protein, a peroxydase-linked secondary antibody (anti-mouse IgG, Roche Molecular Biochemicals) and the amount of peptide-bound MDM2 is determined calorimetrically by the addition of a peroxydase substrate (MTB Microwell Peroxydase Substrate System, Kirkegaard & Perry Labs).

Test plates were prepared by coating with streptavidin (5 mg/ml in PBS) for 2 hours followed by a PBS (phosphate-buffered saline) wash and overnight blocking with 150 μl of blocking buffer containing 2 mg/ml bovine serum albumin (Sigma) and 0.05% Tween 20 (Sigma) in PBS at 4° C. Biotinylated peptide (1 μM) is added to each well in 50 μl of blocking buffer and washed extensively after 1 h incubation. Test compounds were diluted in a separate 96 well plate and added in triplicate to a compound incubation plate containing a mix of the MDM2 protein and anti-MDM2 antibody. After 20 min incubation, the content of the plate is transferred to the test plate and incubated for an additional 1 hour. The secondary anti-mouse IgG antibody is added to the test plate preceeded and followed by a triple wash with 0.05% Tween 20 in PBS. Finally, peroxydase substrate is added to each well and the absorption was read using a plate reader (MR7000, Dynatech) at 450nm. The inhibitory activity of the test compounds was measured as a percentage of the bound MDM2 in treated vs. untreated wells and $IC_{50}$ was calculated.

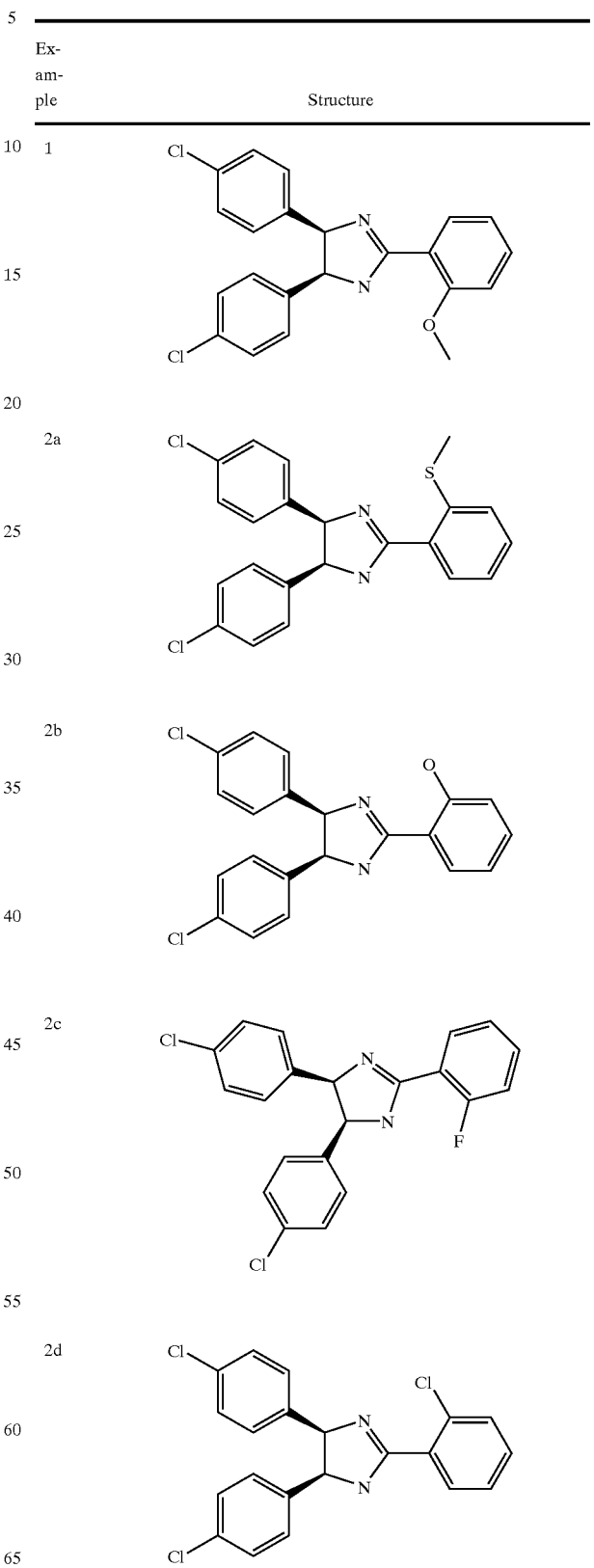

| Example | Structure |
|---|---|
| 1 | 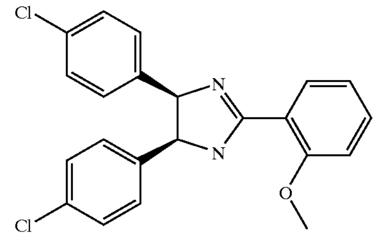 |
| 2a | 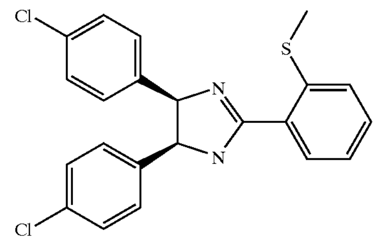 |
| 2b | 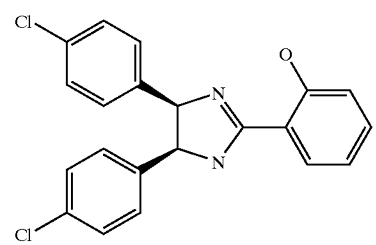 |
| 2c | 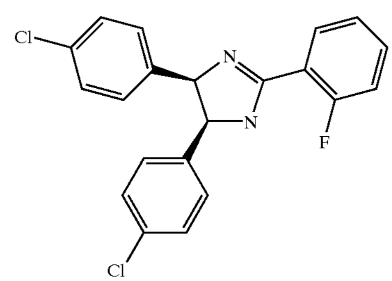 |
| 2d | 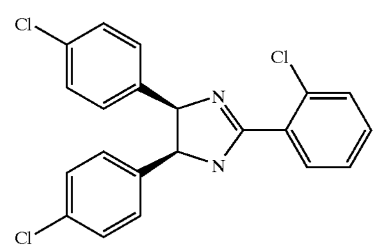 |

-continued

| Example | Structure |
|---|---|
| 2e | 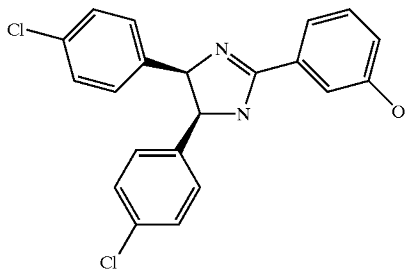 |
| 2f | 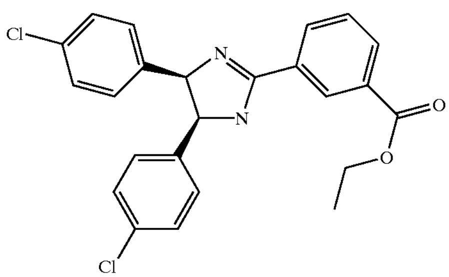 |
| 2g | 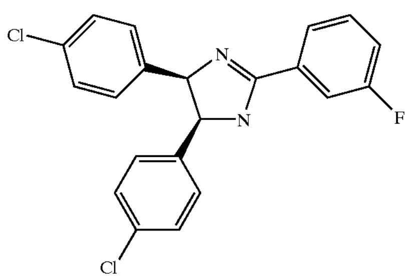 |
| 2h | 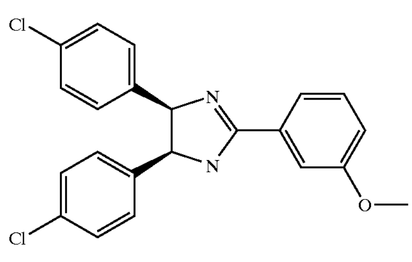 |
| 2i | 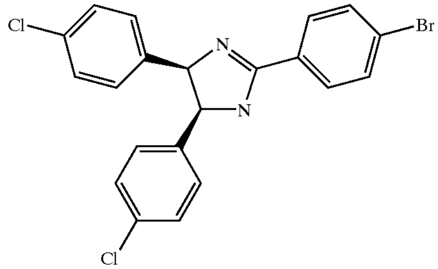 |

-continued

| Example | Structure |
|---|---|
| 2j | 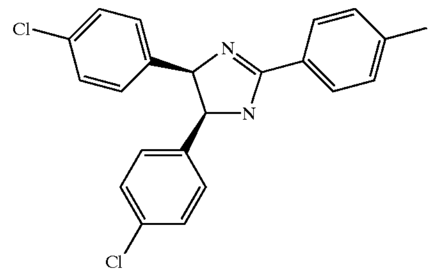 |
| 2k | 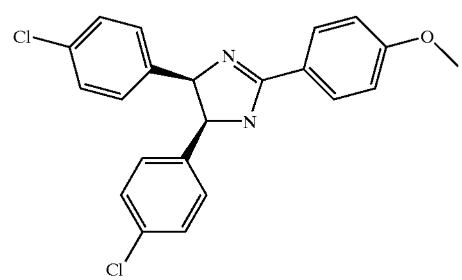 |
| 2l | 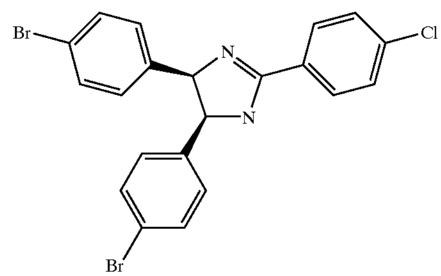 |
| 2m | 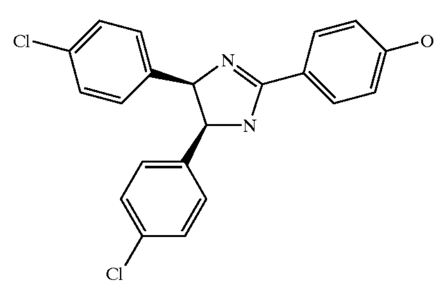 |
| 2n | 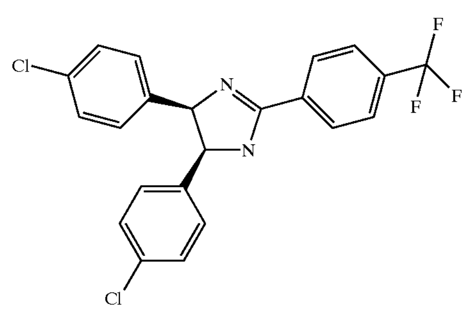 |

-continued

| Example | Structure |
|---------|-----------|
| 2o | 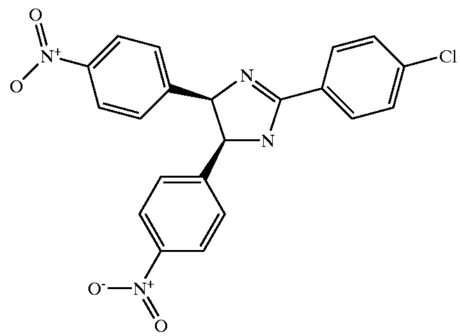 |
| 2p | 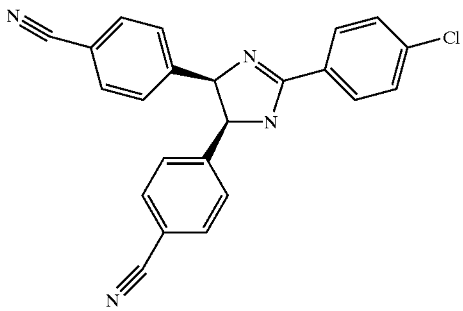 |
| 2q | 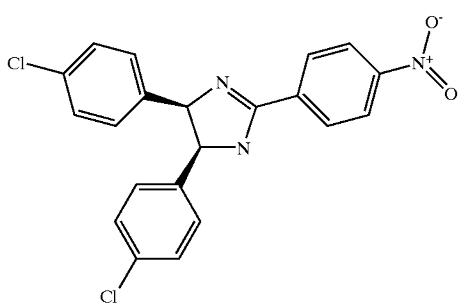 |
| 2r | 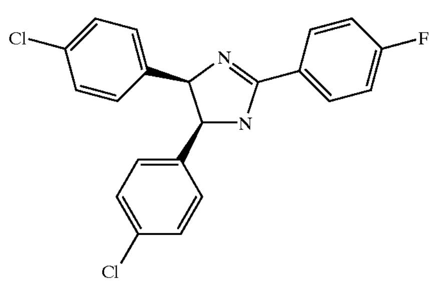 |
| 2s | 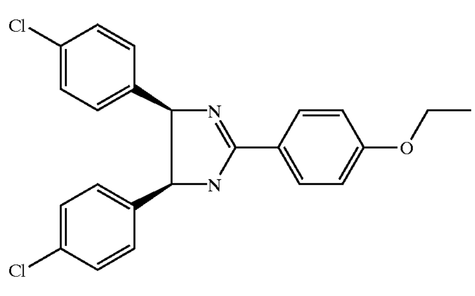 |

-continued

| Example | Structure |
|---------|-----------|
| 2t | 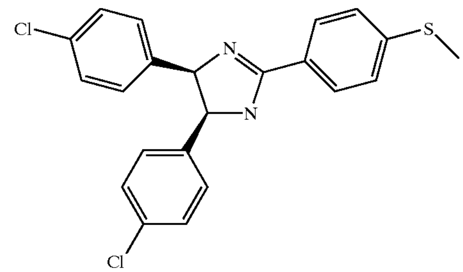 |
| 2u | 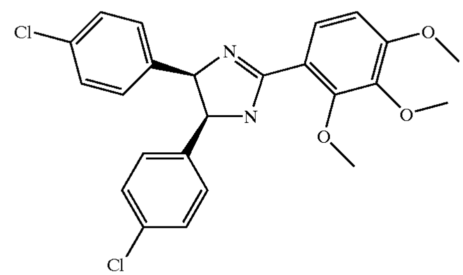 |
| 2v | 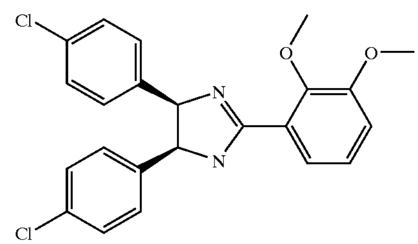 |
| 2w | 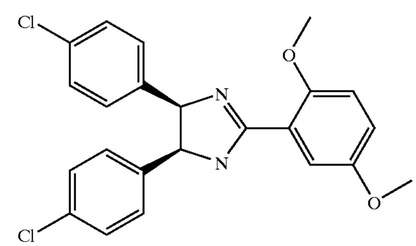 |
| 2x | 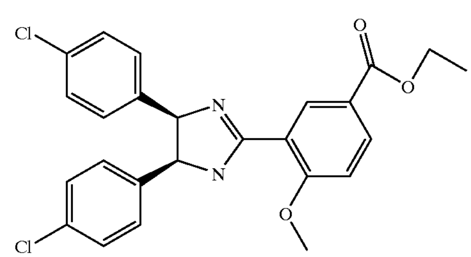 |
| 2y | 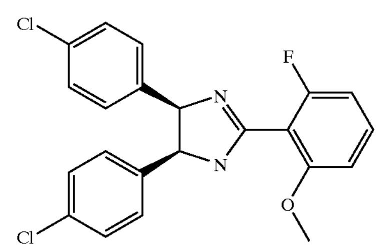 |

| Example | Structure |
|---|---|
| 2z | 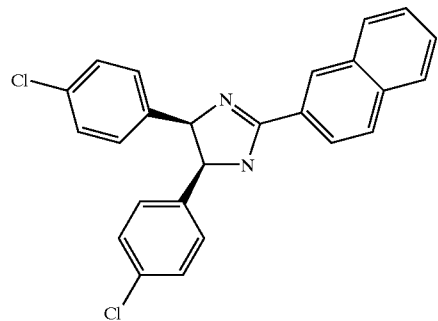 |
| 2aa | 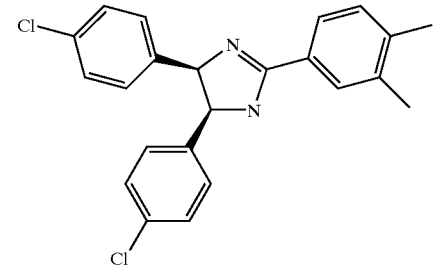 |
| 2bb | 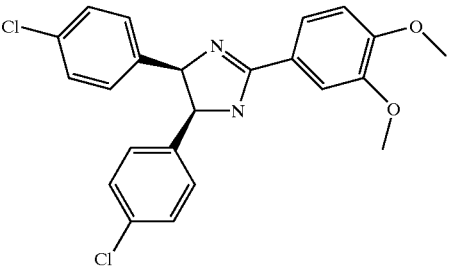 |
| 2cc | 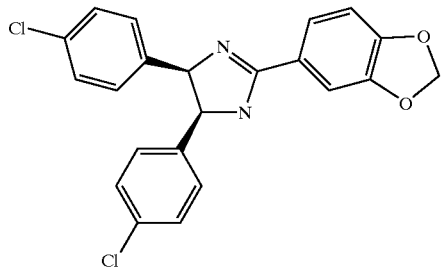 |
| 2dd | 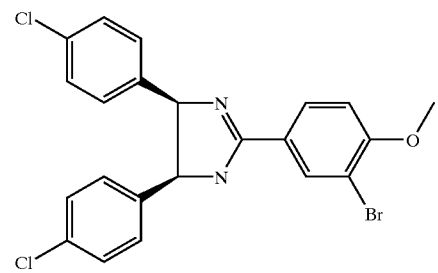 |
| 2ee | 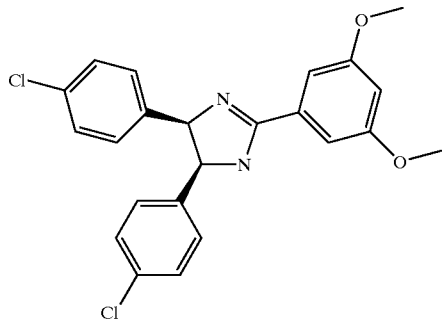 |
| 2ff | 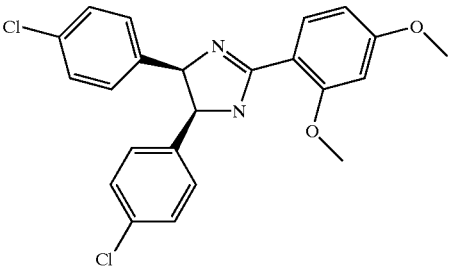 |
| 2gg | 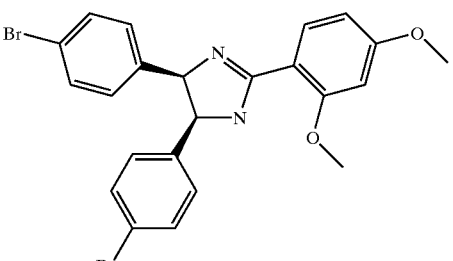 |
| 3 | 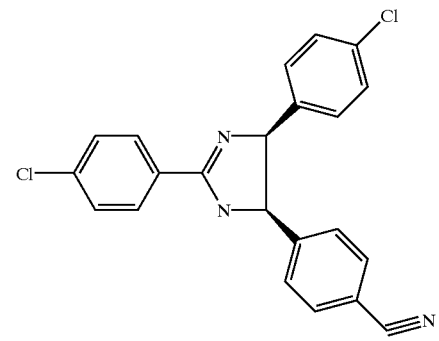 |

-continued
| Example | Structure |
|---|---|
| 4a | 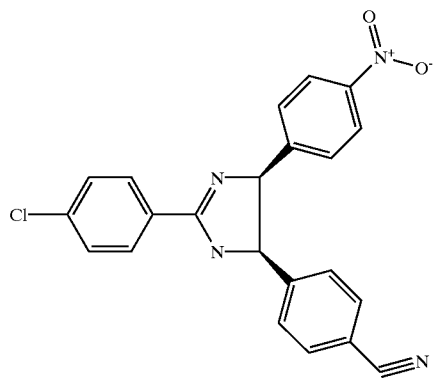 |
| 4b | 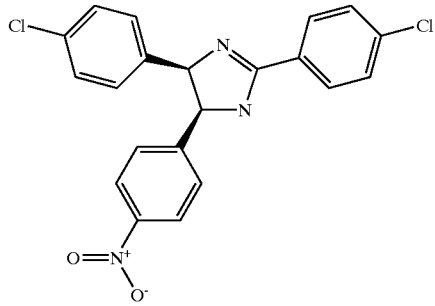 |
| 4c | 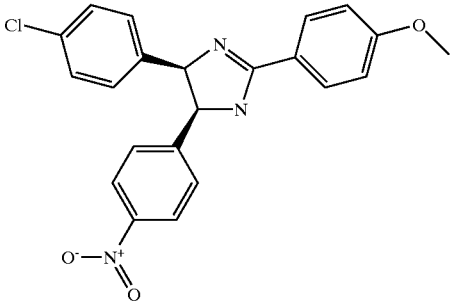 |
| 5 | 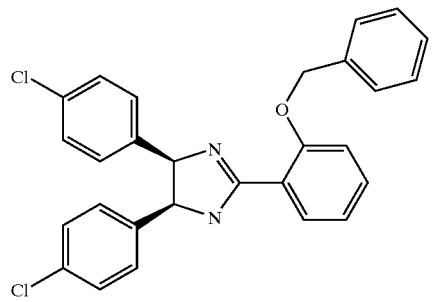 |
-continued
| Example | Structure |
|---|---|
| 6a | 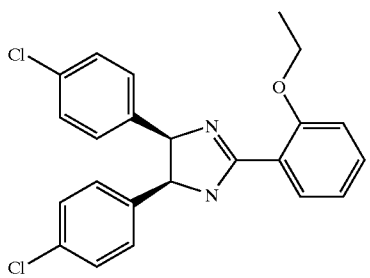 |
| 6b | 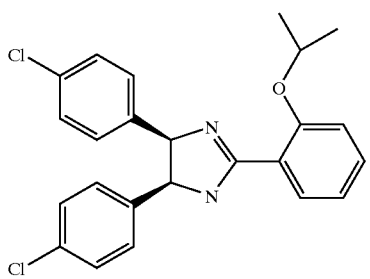 |
| 6c | 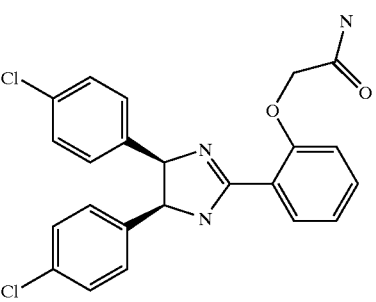 |
| 7 | 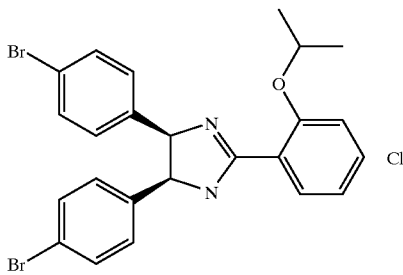 |
| 8 | 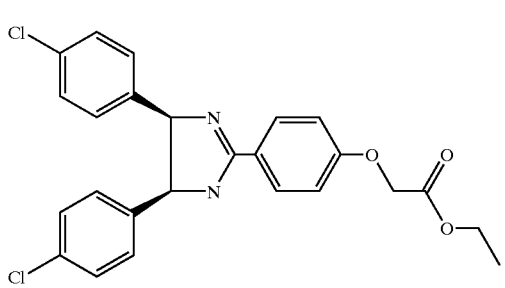 |

| Example | Structure |
|---|---|
| 9a | 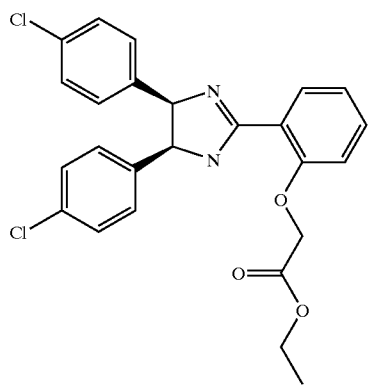 |
| 9b | 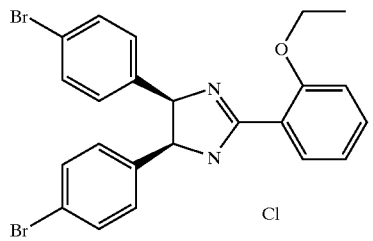 |
| 9c | 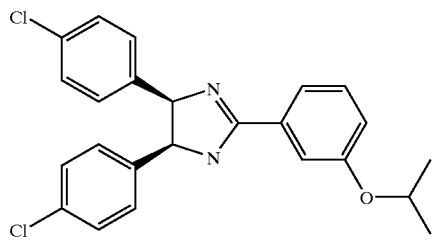 |
| 9d | 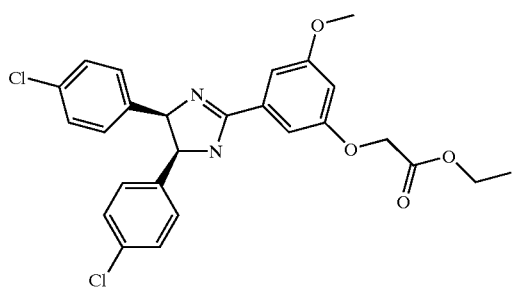 |
| 10 | 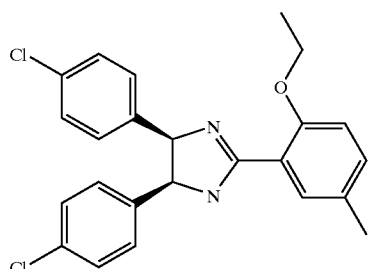 |
| 11a | 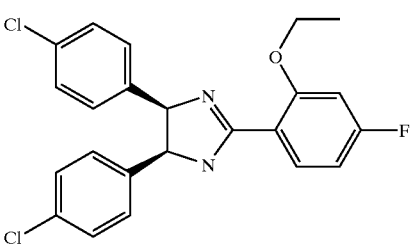 |
| 11b | 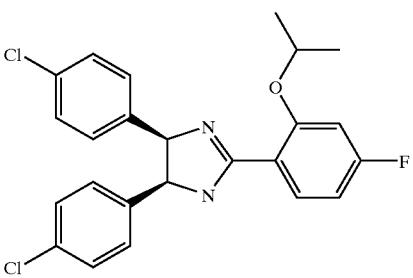 |
| 12 | 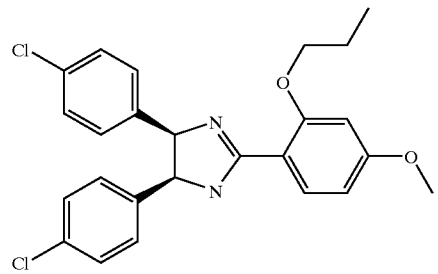 |
| 13a | 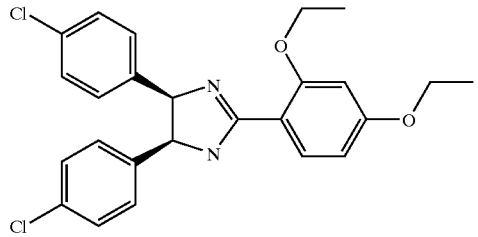 |
| 13b | 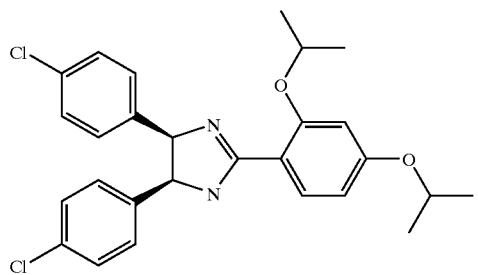 |

US 6,617,346 B1
-continued
| Example | Structure |
|---|---|
| 13c | 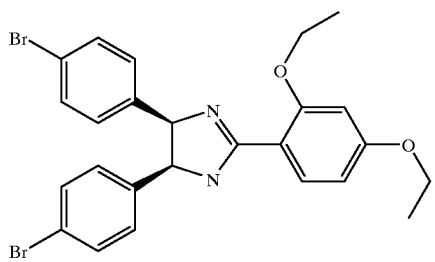 |
| 13d | 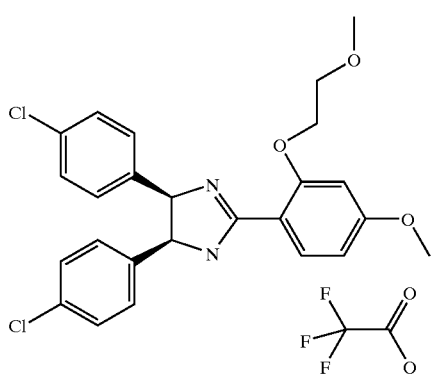 |
| 13e | 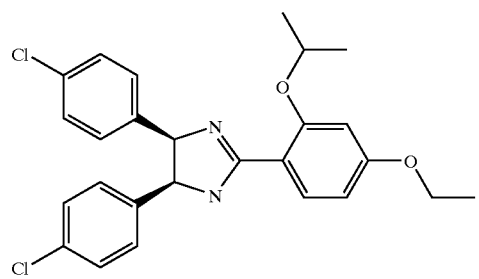 |
| 13f | 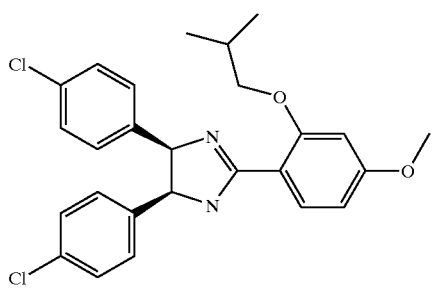 |
| 13g | 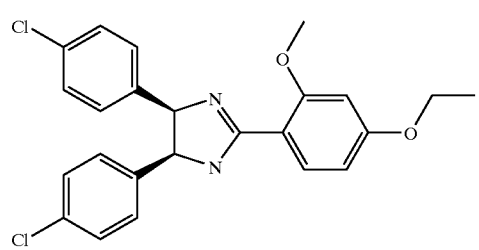 |
-continued
| Example | Structure |
|---|---|
| 13h | 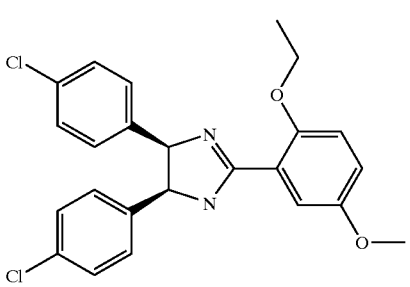 |
| 13i | 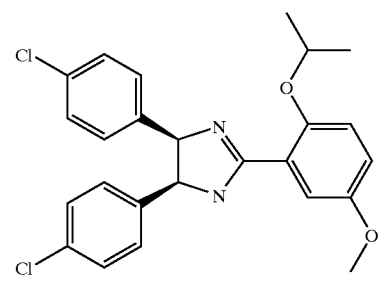 |
| 13j | 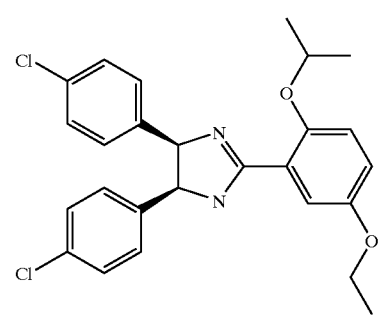 |
| 14 | 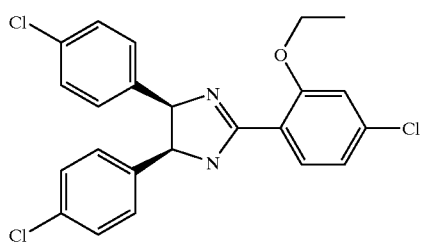 |
| 15 | 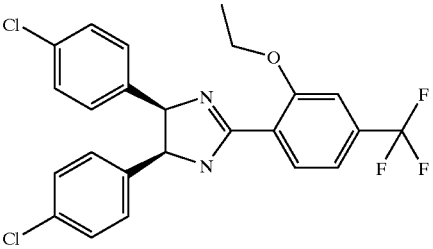 |

-continued
| Example | Structure |
|---|---|
| 16 | 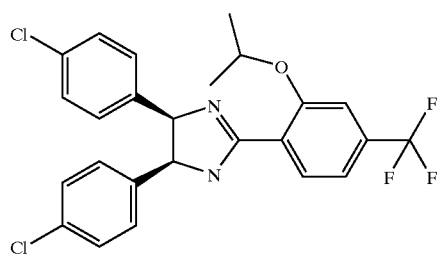 |
| 17 | 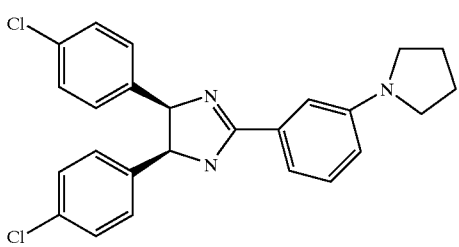 |
| 18 | 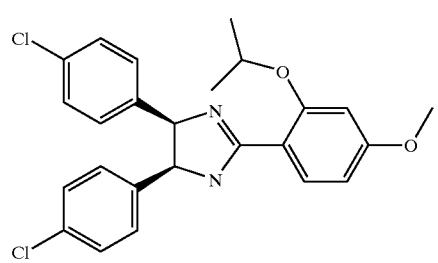 |
| 19a | 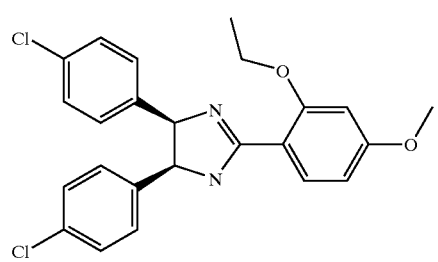 |
| 19b | 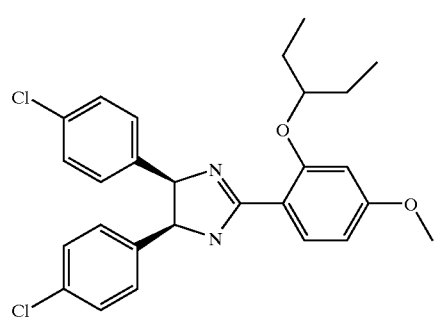 |
-continued
| Example | Structure |
|---|---|
| 19c | 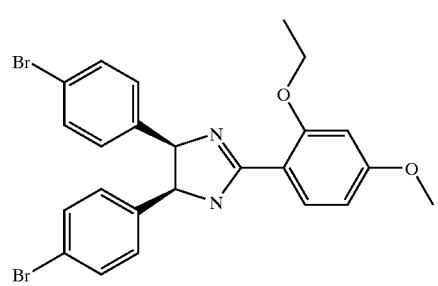 |
| 19d | 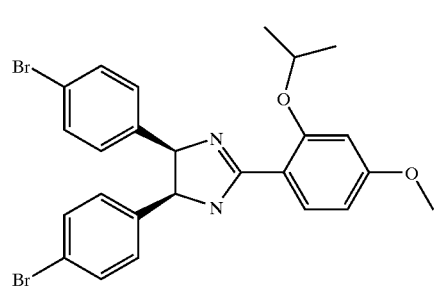 |
| 19e | 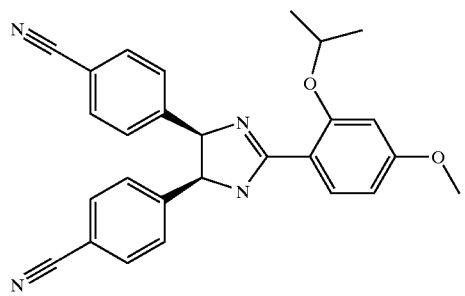 |
| 19f | 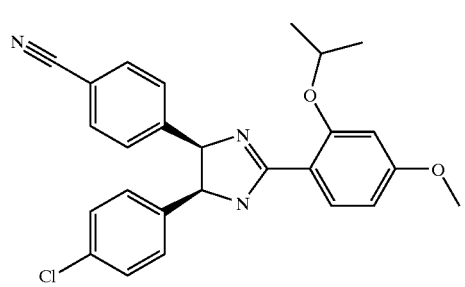 |
| 19g | 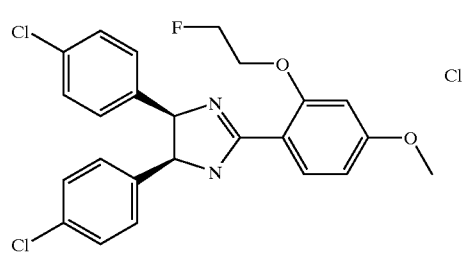 |

-continued
| Example | Structure |
|---|---|
| 20 | 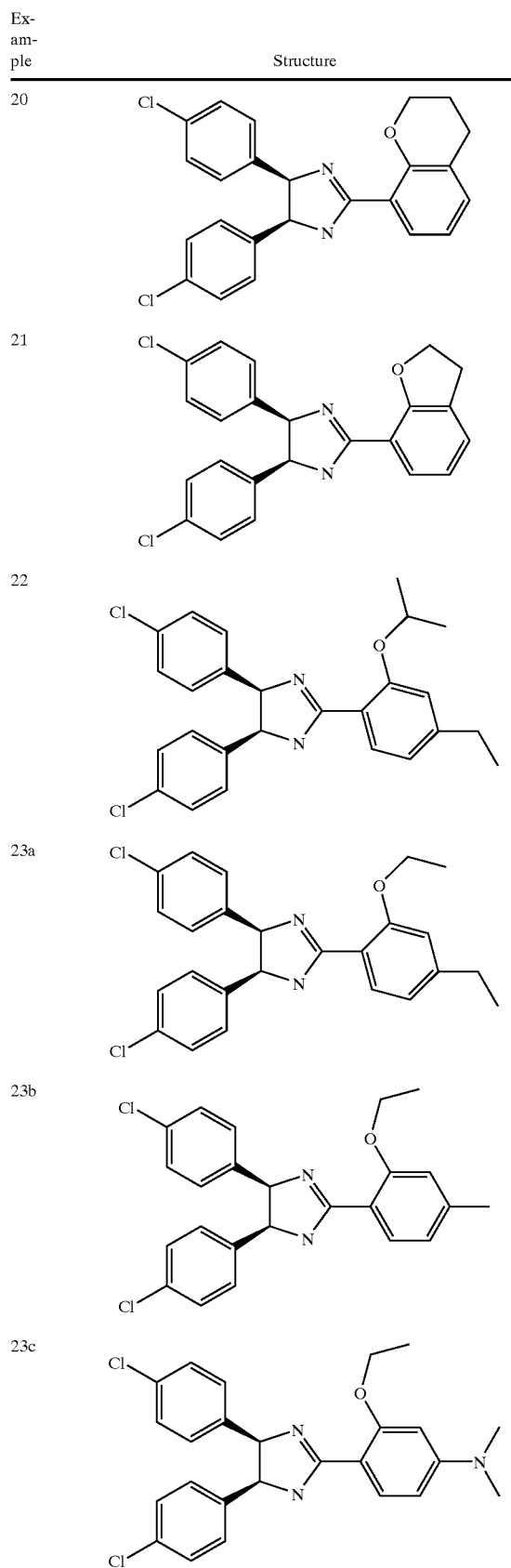 |
| 21 | 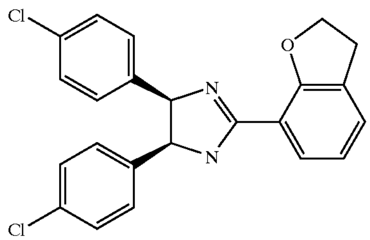 |
| 22 | 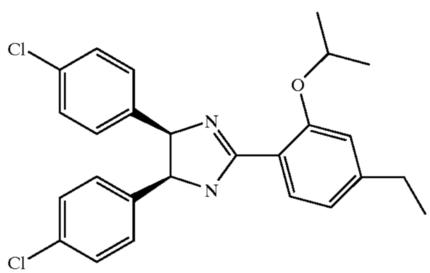 |
| 23a | 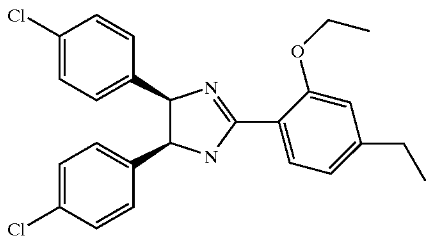 |
| 23b | 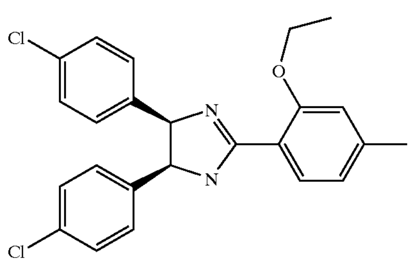 |
| 23c | 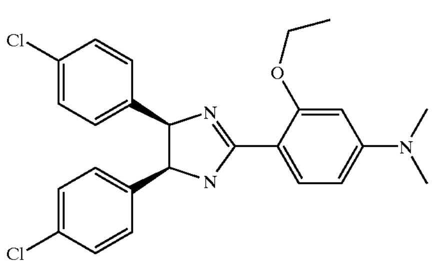 |
-continued
| Example | Structure |
|---|---|
| 24 | 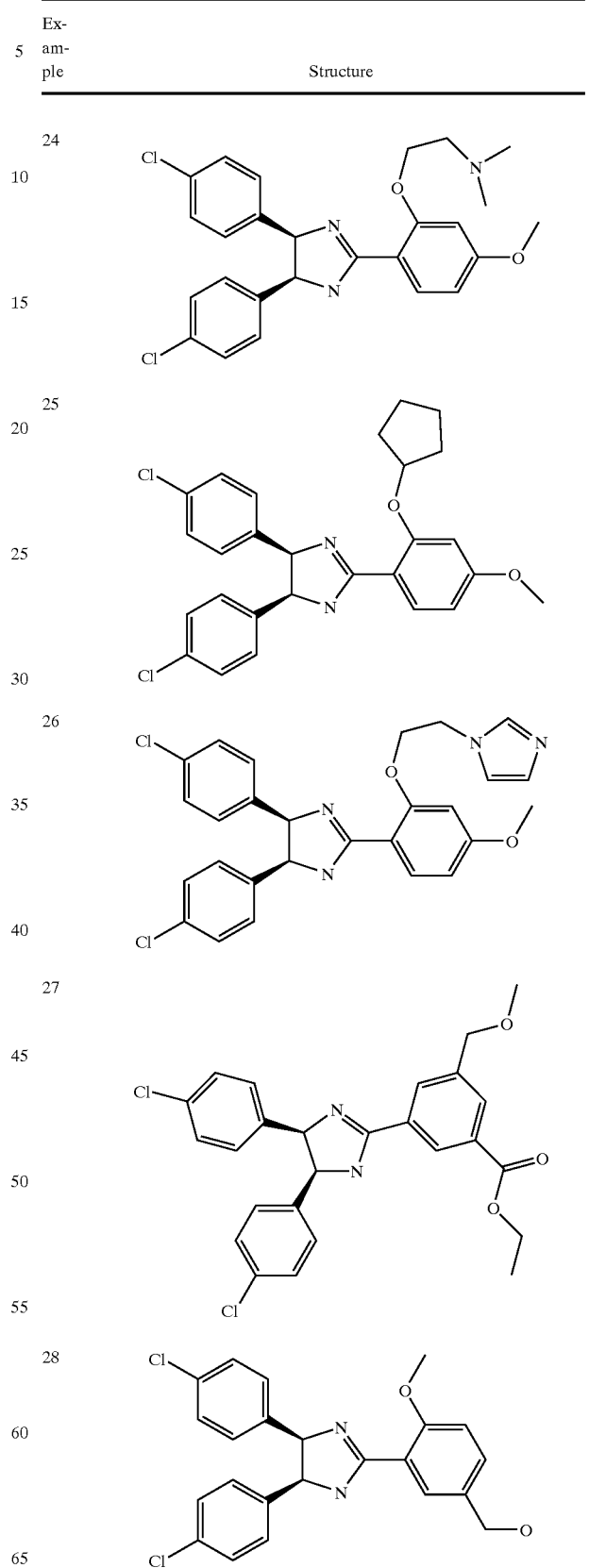 |
| 25 | 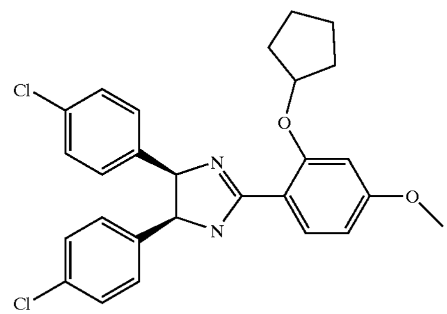 |
| 26 | 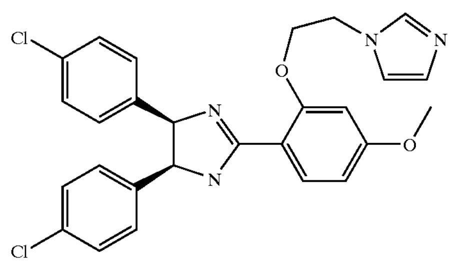 |
| 27 | 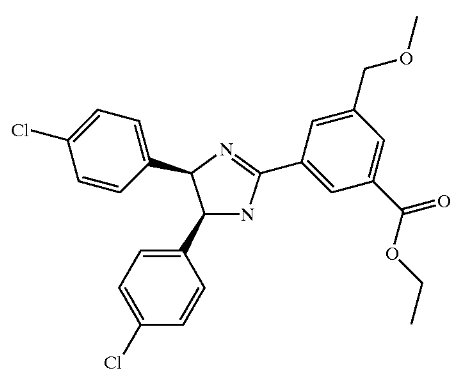 |
| 28 | 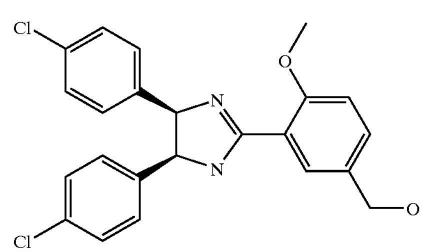 |

-continued
| Example | Structure |
|---|---|
| 29 | 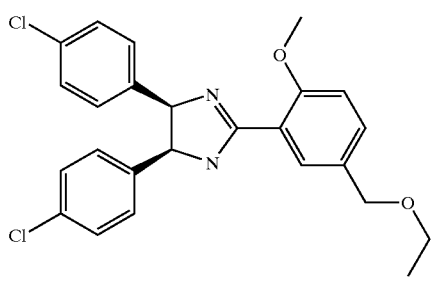 |
| 30 | 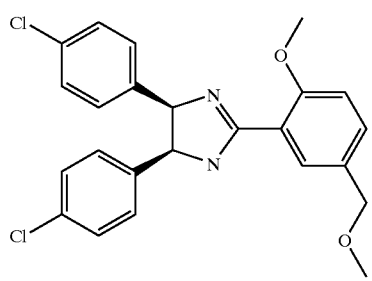 |
| 31 | 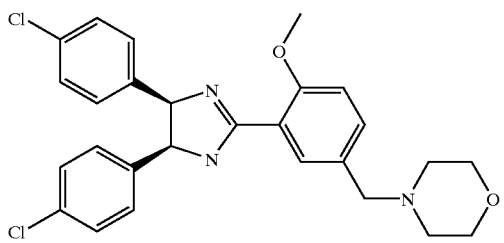 |
| 32 | 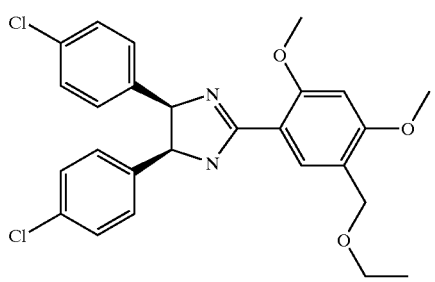 |
| 33 | 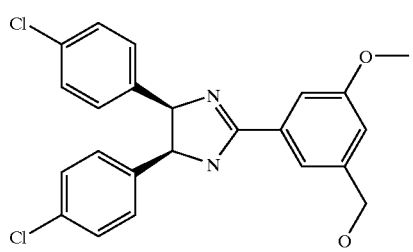 |
-continued
| Example | Structure |
|---|---|
| 34 | 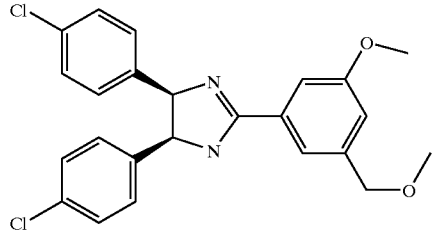 |
| 35 | 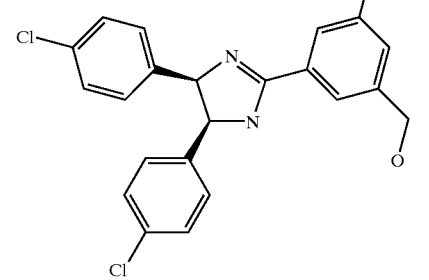 |
| 36 | 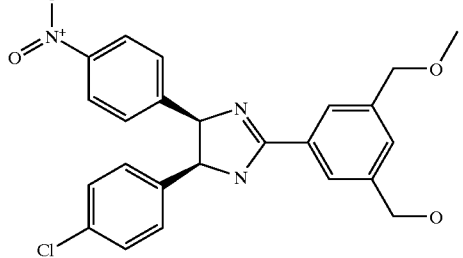 |
| 37 | 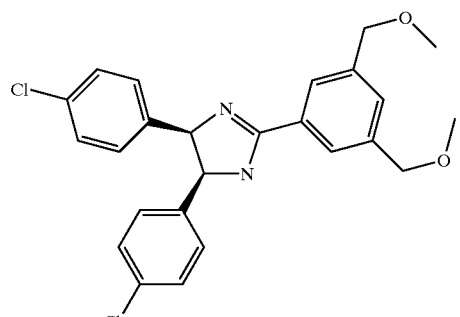 |
| 38 | 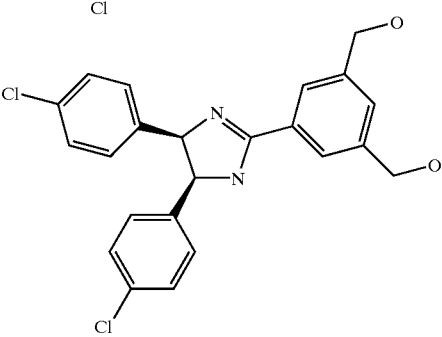 |

-continued
| Example | Structure |
|---|---|
| 39 | 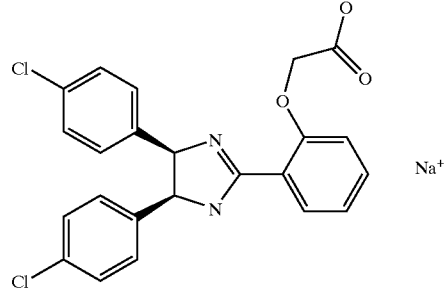 Na⁺ |
| 40a | 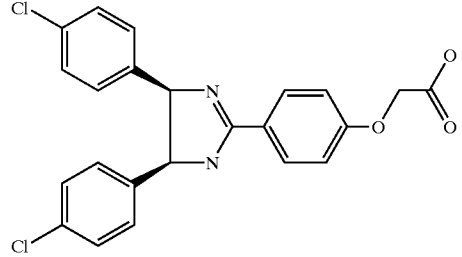 Na⁺ |
| 40b | 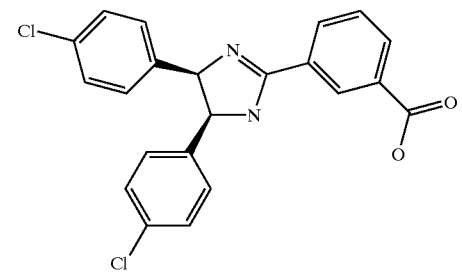 Na⁺ |
| 40c | 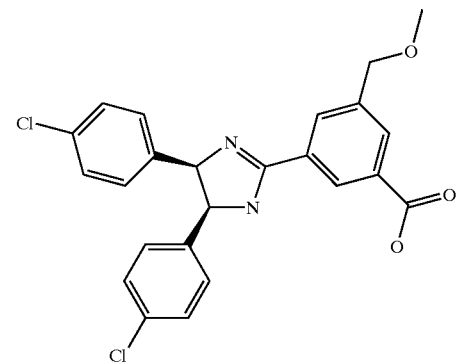 Na⁺ |
| 40d | 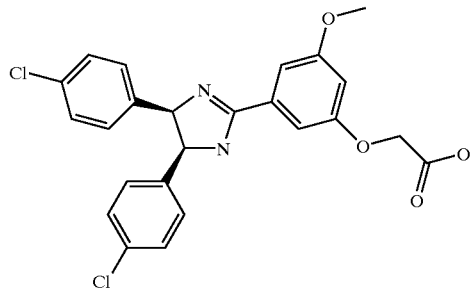 Na⁺ |
-continued
| Example | Structure |
|---|---|
| 40e | 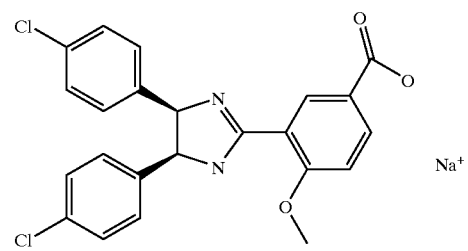 Na⁺ |
| 41 | 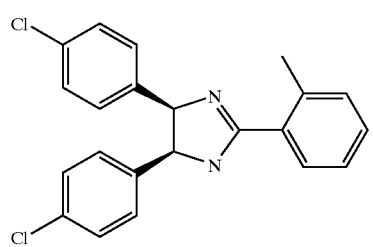 |
| 42 | 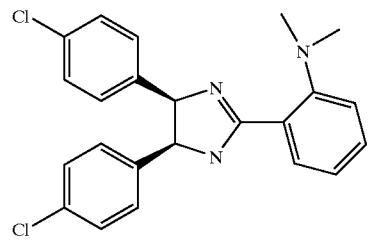 |
| 43 | 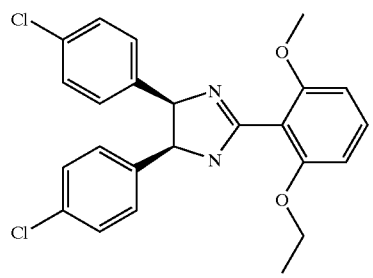 |
| 44 | 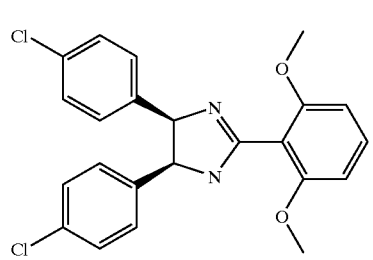 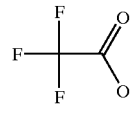 |

-continued

| Example | Structure |
|---|---|
| 45 | 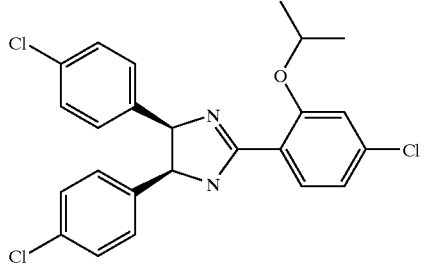 |
| 46 | 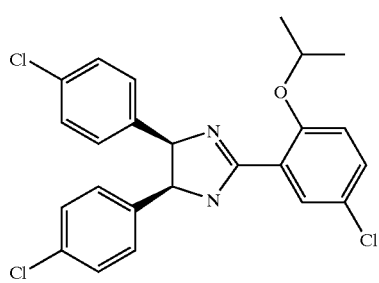 |
| 47a | 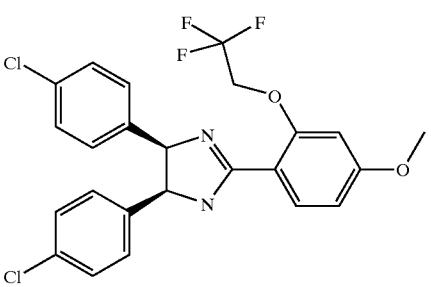 |
| 47b | 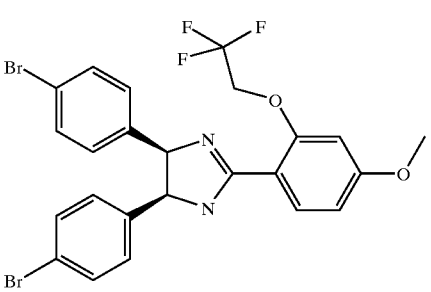 |
| 47c | 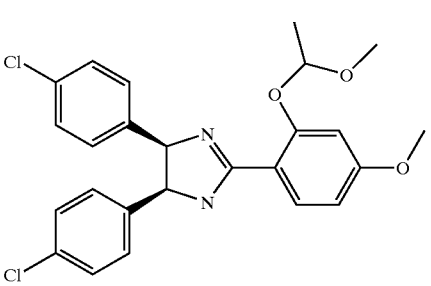 |

-continued

| Example | Structure |
|---|---|
| 47d | 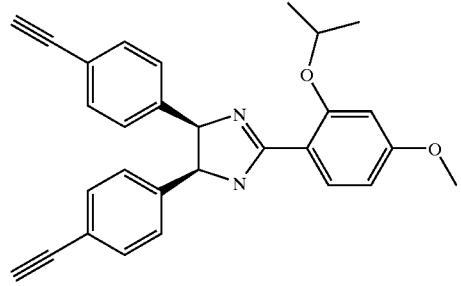 |
| 47e | 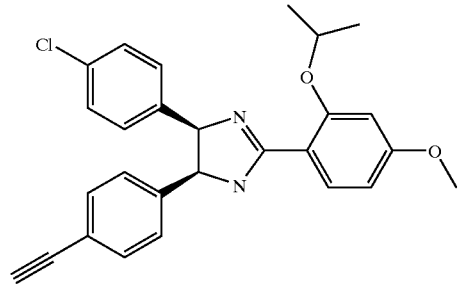 |

What is claimed is:

1. A compound of formula I

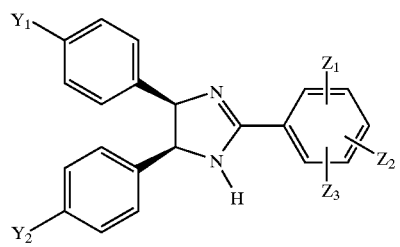

and the pharmaceutically acceptable salts and esters thereof, wherein $Z_1$, $Z_2$ and $Z_3$ are each independently selected from lower alkoxy, —$CH_2OCH_3$, and —$CH_2OCH_2CH_3$, or one of $Z_1$, $Z_2$ or $Z_3$ is —H and the other two are each independently selected from lower alkyl, lower alkoxy, —Cl, —Br, —F, —$CF_3$, —$CH_2OCH_3$, —$CH_2OCH_2CH_3$, —$OCH_2CH_2R_1$, —$CH_2$-morpholino, —$OR_2$, —$CH_2R_2$, —$OCH_2CF_3$, —$OCH(CH_3)CH_2OH$ and —COOQ, wherein Q is selected from —H and lower alkyl, or one of $Z_1$, $Z_2$ or $Z_3$ is —H and the other two taken together with the two carbon atoms and the bonds between them from the benzene ring to which they are substituted form a ring selected from 5- and 6-membered unsaturated rings, and 5- and 6-membered saturated rings that contain at least one hetero atom selected from S, N, and O, wherein $R_1$ is selected from —F, —$OCH_3$, —$N(CH_3)_2$, and unsaturated 5-membered rings containing at least one hetero atom wherein the hetero atom is selected from S, N and O, wherein $R_2$ is a 3- to 6-membered saturated ring, and $Y_1$ and $Y_2$ are each independently selected from —Cl, —Br, —NO$_2$, —C≡N and —C≡CH.

2. The compound according to claim 1 wherein $Y_1$ and $Y_2$ are each independently selected from —Cl and —Br.

3. The compound according to claim 2 wherein one of $Z_1$, $Z_2$ or $Z_3$ is —H and the other two are independently selected from lower alkoxy, —OCH$_2$CF$_3$ and —OCH$_2$CH$_2$F, wherein lower alkoxy is C1–C5 alkoxy.

4. The compound according to claim 1, wherein
$Z_1$, $Z_2$, and $Z_3$ are each independently selected from lower alkoxy which is C1–C5 alkoxy,
or one of $Z_1$, $Z_2$ or $Z_3$ is —H and the other two are independently selected from lower alkyl and lower alkoxy, wherein lower alkyl is C1–C2 alkyl and lower alkoxy is C1–C5 alkoxy.

5. A compound of formula II

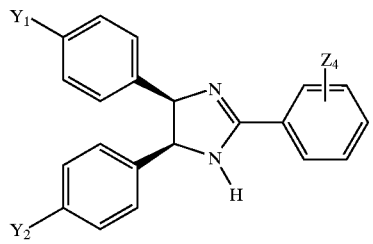

II and the pharmaceutically acceptable salts and esters thereof, wherein
$Z_4$ is selected from C1–C2 alkyl, lower alkoxy, —OH, —SCH$_3$, —CF$_3$, —NO$_2$, —COOQ$_2$, —N(CH$_3$)$_2$, —OCH$_2$-phenyl, —Cl, —Br, —F, —OCH$_2$C=OOQ$_1$, saturated 5- and 6-membered rings containing at least one hetero atom wherein the hetero atom is selected from S, N and O,
wherein $Q_1$ is selected from —H, —NH$_2$, and lower alkyl,
wherein $Q_2$ is selected from —H and lower alkyl,
$Y_1$ and $Y_2$ are independently selected from —Cl, —Br, —NO$_2$, —C≡N and —C≡CH,
with the proviso that where $Y_1$ and $Y_2$ are both —Cl, $Z_4$ is not —Cl, and
with the proviso that where $Y_1$ and $Y_2$ are both —NO$_2$, $Z_4$ is not —NO$_2$, and
with the proviso that where $Y_1$ and $Y_2$ are both —CN, $Z_4$ is not —CN.

6. The compound according to claim 1, selected from the group of:
4,5-Bis-(4-chloro-phenyl)-2-(2,3,4-trimethoxy-phenyl)-4,5-dihydro-1H-imidazole;
4,5-Bis-(4-chloro-phenyl)-2-(2,3-dimethoxy-phenyl)-4,5-dihydro-1H-imidazole;
4,5-Bis-(4-chloro-phenyl)-2-(2,5-dimethoxy-phenyl)-4,5-dihydro-1H-imidazole;
3-[4,5-Bis-(4-chloro-phenyl)-4,5-dihydro-1H-imidazol-2-yl]-4-methoxy-benzoic acid ethyl ester;
4,5-Bis-(4-chloro-phenyl)-2-(2-fluoro-6-methoxy-phenyl)-4,5-dihydro-1H-imidazole;
4,5-Bis-(4-chloro-phenyl)-2-naphthalen-2-yl-4,5-dihydro-1H-imidazole;
4,5-Bis-(4-chloro-phenyl)-2-(3,4-dimethyl-phenyl)-4,5-dihydro-1H-imidazole;
4,5-Bis-(4-chloro-phenyl)-2-(3,4-dimethoxy-phenyl)-4,5-dihydro-1H-imidazole;
2-Benzo[1,3]dioxol-5-yl-4,5-bis-(4-chloro-phenyl)-4,5-dihydro-1H-imidazole;
2-(3-Bromo-4-methoxy-phenyl)-4,5-bis-(4-chloro-phenyl)-4,5-dihydro-1H-imidazole;
4,5-Bis-(4-chloro-phenyl)-2-(3,5-dimethoxy-phenyl)-4,5-dihydro-1H-imidazole;
4,5-Bis-(4-chloro-phenyl)-2-(2,4-dimethoxy-phenyl)-4,5-dihydro-1H-imidazole;
4,5-Bis-(4-bromo-phenyl)-2-(2,4-dimethoxy-phenyl)-4,5-dihydro-1H-imidazole;
{3-[4,5-Bis-(4-chloro-phenyl)-4,5-dihydro-1H-imidazol-2-yl]-5-methoxy-phenoxy}-acetic acid ethyl ester;
4,5-Bis-(4-chloro-phenyl)-2-(2-ethoxy-5-methyl-phenyl)-4,5-dihydro-1H-imidazole;
4,5-Bis-(4-chloro-phenyl)-2-(2-ethoxy-4-fluoro-phenyl)-4,5-dihydro-1H-imidazole;
4,5-Bis-(4-chloro-phenyl)-2-(4-fluoro-2-isopropoxy-phenyl)-4,5-dihydro-1H-imidazole;
4,5-Bis-(4-chloro-phenyl)-2-(4-methoxy-2-propoxy-phenyl)-4,5-dihydro-1H-imidazole;
4,5-Bis-(4-chloro-phenyl)-2-(2,4-diethoxy-phenyl)-4,5-dihydro-1H-imidazole;
4,5-Bis-(4-chloro-phenyl)-2-(2,4-diisopropoxy-phenyl)-4,5-dihydro-1H-imidazole;
4,5-Bis-(4-bromo-phenyl)-2-(2,4-diethoxy-phenyl)-4,5-dihydro-1H-imidazole; and
4,5-Bis-(4-chloro-phenyl)-2-[4-methoxy-2-(2-methoxy-ethoxy)-phenyl]-4,5-dihydro-1H-imidazole, trifluoro-acetic acid salt.

7. The compound according to claim 1, selected from the group of:
4,5-Bis-(4-chloro-phenyl)-2-(4-ethoxy-2-isopropoxy-phenyl)-4,5-dihydro-1H-imidazole;
4,5-Bis-(4-chloro-phenyl)-2-(2-isobutoxy-4-methoxy-phenyl)-4,5-dihydro-1H-imidazole;
4,5-Bis-(4-chloro-phenyl)-2-(4-ethoxy-2-methoxy-phenyl)-4,5-dihydro-1H-imidazole;
4,5-Bis-(4-chloro-phenyl)-2-(2-ethoxy-5-methoxy-phenyl)-4,5-dihydro-1H-imidazole;
4,5-Bis-(4-chloro-phenyl)-2-(2-isopropoxy-5-methoxy-phenyl)-4,5-dihydro-1H-imidazole;
4,5-Bis-(4-chloro-phenyl)-2-(5-ethoxy-2-isopropoxy-phenyl)-4,5-dihydro-1H-imidazole;
2-(4-Chloro-2-ethoxy-phenyl)-4,5-bis-(4-chloro-phenyl)-4,5-dihydro-1H-imidazole;
4,5-Bis-(4-chloro-phenyl)-2-(2-ethoxy-4-trifluoromethyl-phenyl)-4,5-dihydro-1H-imidazole;
4,5-Bis-(4-chloro-phenyl)-2-(2-isopropoxy-4-trifluoromethyl-phenyl)-4,5-dihydro-1H-imidazole;
4,5-Bis-(4-chloro-phenyl)-2-(2-isopropoxy-4-methoxy-phenyl)-4,5-dihydro-1H-imidazole;
4,5-Bis-(4-chloro-phenyl)-2-(2-ethoxy-4-methoxy-phenyl)-4,5-dihydro-1H-imidazole;
4,5-Bis-(4-chloro-phenyl)-2-[2-(1-ethyl-propoxy)-4-methoxy-phenyl]-4,5-dihydro-1H-imidazole;
4,5-Bis-(4-bromo-phenyl)-2-(2-ethoxy-4-methoxy-phenyl)-4,5-dihydro-1H-imidazole;
4,5-Bis-(4-bromo-phenyl)-2-(2-isopropoxy-4-methoxy-phenyl)-4,5-dihydro-1H-imidazole;
4,5-Bis-(4-cyano-phenyl)-2-(2-isopropoxy-4-methoxy-phenyl)-4,5-dihydro-1H-imidazole;
4-[5-(4-Chloro-phenyl)-2-(2-isopropoxy-4-methoxy-phenyl)-4,5-dihydro-1H-imidazol-4-yl]-benzonitrile;

4,5-Bis-(4-chloro-phenyl)-2-[2-(2-fluoro-ethoxy)-4-methoxy-phenyl]-4,5-dihydro-1H-imidazole, hydrochloride salt;

4,5-Bis-(4-chloro-phenyl)-2-chroman-8-yl-4,5-dihydro-1H-imidazole;

4,5-Bis-(4-chloro-phenyl)-2-(2,3-dihydro-benzofuran-7-yl)-4,5-dihydro-1H-imidazole;

4,5-Bis-(4-chloro-phenyl)-2-(4-ethyl-2-isopropoxy-phenyl)-4,5-dihydro-1H-imidazole;

4,5-Bis-(4-chloro-phenyl)-2-(2-ethoxy-4-ethyl-phenyl)-4,5-dihydro-1H-imidazole; and 4,5-Bis-(4-chloro-phenyl)-2-(2-ethoxy-4-methyl-phenyl)-4,5-dihydro-1H-imidazole.

8. The compound according to claim 1, selected from the group of:

{4-[4,5-Bis-(4-chloro-phenyl)-4,5-dihydro-1H-imidazol-2-yl]-3-ethoxy-phenyl}-dimethyl-amine;

(2-{2-[4,5-Bis-(4-chloro-phenyl)-4,5-dihydro-1H-imidazol-2-yl]-5-methoxy-phenoxy}-ethyl)-dimethyl-amine;

4,5-Bis-(4-chloro-phenyl)-2-(2-cyclopentyloxy-4-methoxy-phenyl)-4,5-dihydro-1H-imidazole;

1-(2-{2-[4,5-Bis-(4-chloro-phenyl)-4,5-dihydro-1H-imidazol-2-yl]-5-methoxy-phenoxy}-ethyl)-1H-imidazole;

3-[4,5-Bis-(4-chloro-phenyl)-4,5-dihydro-1H-imidazol-2-yl]-5-methoxymethyl-benzoic acid ethyl ester;

4,5-Bis-(4-chloro-phenyl)-2-(5-hydroxymethyl-2-methoxy-phenyl)-4,5-dihydro-1H-imidazole;

4,5-Bis-(4-chloro-phenyl)-2-(5-ethoxymethyl-2-methoxy-phenyl)-4,5-dihydro-1H-imidazole;

4,5-Bis-(4-chloro-phenyl)-2-(2-methoxy-5-methoxymethyl-phenyl)-4,5-dihydro-1H-imidazole;

4-{3-[4,5-Bis-(4-chloro-phenyl)-4,5-dihydro-1H-imidazol-2-yl]-4-methoxy-benzyl}-morpholine;

4,5-Bis-(4-chloro-phenyl)-2-(5-ethoxymethyl-2,4-dimethoxy-phenyl)-4,5-dihydro-1H-imidazole;

{3-[4,5-Bis-(4-chloro-phenyl)-4,5-dihydro-1H-imidazol-2-yl]-5-methoxy-phenyl}-methanol;

4,5-Bis-(4-chloro-phenyl)-2-(3-methoxy-5-methoxymethyl-phenyl)-4,5-dihydro-1H-imidazole;

{3-[4,5-Bis-(4-chloro-phenyl)-4,5-dihydro-1H-imidazol-2-yl]-5-methoxymethyl-phenyl}-methanol;

{3-[5-(4-Chloro-phenyl)-4-(4-nitro-phenyl)-4,5-dihydro-1H-imidazol-2-yl]-5methoxymethyl-phenyl}-methanol;

2-(3,5-Bis-methoxymethyl-phenyl)-4,5-bis-(4-chloro-phenyl)-4,5-dihydro-1H-imidazole;

{3-[4,5-Bis-(4-chloro-phenyl)-4,5-dihydro-1H-imidazol-2-yl]-5-hydroxymethyl-phenyl}-methanol;

Sodium 3-[4,5-bis-(4-chloro-phenyl)-4,5-dihydro-1H-imidazol-2-yl]-5-methoxymethyl-benzoate;

Sodium {3-[4,5-bis-(4-chloro-phenyl)-4,5-dihydro-1H-imidazol-2-yl]-5-methoxy-phenoxy}-acetate;

Sodium 3-[4,5-bis-(4-chloro-phenyl)-4,5-dihydro-1H-imidazol-2-yl]-4-methoxy-benzoate;

4,5-Bis-(4-chloro-phenyl)-2-(2-ethoxy-6-methoxy-phenyl)-4,5-dihydro-1H-imidazole; and 4,5-Bis-(4-chloro-phenyl)-2-(2,6-dimethoxy-phenyl)-4,5-dihydro-1H-imidazole, trifluoroacetic acid salt.

9. The compound according to claim 1, selected from the group of:

2-(4-Chloro-2-isopropoxy-phenyl)-4,5-bis-(4-chloro-phenyl)-4,5-dihydro-1-imidazole;

2-(5-Chloro-2-isopropoxy-phenyl)-4,5-bis-(4-chloro-phenyl)-4,5-dihydro-1H-imidazole;

4,5-Bis-(4-chloro-phenyl)-2-[4-methoxy-2-(2,2,2-trifluoro-ethoxy)-phenyl]-4,5-dihydro-1H-imidazole;

4,5-Bis-(4-bromo-phenyl)-2-[4-methoxy-2-(2,2,2-trifluoro-ethoxy)-phenyl]-4,5-dihydro-1H-imidazole;

2-{2-[4,5-Bis-(4-chloro-phenyl)-4,5-dihydro-1H-imidazol-2-yl]-5-methoxy-phenoxy}-propan-1-ol;

4,5-Bis-(4-ethynyl-phenyl)-2-(2-isopropoxy-4-methoxy-phenyl)-4,5-dihydro-1H-imidazole; and 4-(4-Chloro-phenyl)-5-(4-ethynyl-phenyl)-2-(2-isopropoxy-4-methoxy-phenyl)-4,5-dihydro-1H-imidazole.

10. The compound according to claim 5, selected from the group of:

4,5-Bis-(4-chloro-phenyl)-2-(2-methoxy-phenyl)-4,5-dihydro-1H-imidazole;

4,5-Bis-(4-chloro-phenyl)-2-(2-methylsulfanyl-phenyl)-4,5-dihydro-1H-imidazole;

2-[4,5-Bis-(4-chloro-phenyl)-4,5-dihydro-1H-imidazol-2-yl]-phenol;

4,5-Bis-(4-chloro-phenyl)-2-(2-fluoro-phenyl)-4,5-dihydro-1H-imidazole;

2-(2-Chloro-phenyl)-4,5-bis-(4-chloro-phenyl)-4,5-dihydro-1H-imidazole;

3-[4,5-Bis-(4-chloro-phenyl)-4,5-dihydro-1H-imidazol-2-yl]-phenol;

3-[4,5-Bis-(4-chloro-phenyl)-4,5-dihydro-1H-imidazol-2-yl]-benzoic acid ethyl ester;

4,5-Bis-(4-chloro-phenyl)-2-(3-fluoro-phenyl)-4,5-dihydro-1H-imidazole;

4,5-Bis-(4-chloro-phenyl)-2-(3-methoxy-phenyl)-4,5-dihydro-1H-imidazole;

2-(4-Bromo-phenyl)-4,5-bis-(4-chloro-phenyl)-4,5-dihydro-1H-imidazole;

4,5-Bis-(4-chloro-phenyl)-2-p-tolyl-4,5-dihydro-1H-imidazole;

4,5-Bis-(4-chloro-phenyl)-2-(4-methoxy-phenyl)-4,5-dihydro-1H-imidazole;

4,5-Bis-(4-bromo-phenyl)-2-(4-chloro-phenyl)-4,5-dihydro-1H-imidazole;

4-[4,5-Bis-(4-chloro-phenyl)-4,5-dihydro-1H-imidazol-2-yl]-phenol;

4,5-Bis-(4-chloro-phenyl)-2-(4-trifluoromethyl-phenyl)-4,5-dihydro-1H-imidazole;

2-(4-Chloro-phenyl)-4,5-bis-(4-nitro-phenyl)-4,5-dihydro-1H-imidazole;

2-(4-Chloro-phenyl)-4,5-bis-(4-cyano-phenyl)-4,5-dihydro-1H-imidazole;

4,5-Bis-(4-chloro-phenyl)-2-(4-nitro-phenyl)-4,5-dihydro-1H-imidazole;

4,5-Bis-(4-chloro-phenyl)-2-(4-fluoro-phenyl)-4,5-dihydro-1H-imidazole; and 4,5-Bis-(4-chloro-phenyl)-2-(4-ethoxy-phenyl)-4,5-dihydro-1H-imidazole.

11. The compound according to claim 5, selected from the group:

4,5-Bis-(4-chloro-phenyl)-2-(4-methylsulfanyl-phenyl)-4,5-dihydro-1H-imidazole;

4-[2,5-Bis-(4-chloro-phenyl)-4,5-dihydro-3H-imidazol-4-yl]-benzonitrile;

4-[2-(4-Chloro-phenyl)-5-(4-nitro-phenyl)-4,5-dihydro-3H-imidazol-4-yl]-benzonitrile;

2,4-Bis-(4-chloro-phenyl)-5-(4-nitro-phenyl)-4,5-dihydro-1H-imidazole;

4-(4-Chloro-phenyl)-2-(4-methoxy-phenyl)-5-(4-nitro-phenyl)-4,5-dihydro-1H-imidazole;

2-(2-Benzyloxy-phenyl)-4,5-bis-(4-chloro-phenyl)-4,5-dihydro-1H-imidazole;

4,5-Bis-(4-chloro-phenyl)-2-(2-ethoxy-phenyl)-4,5-dihydro-1H-imidazole;

4,5-Bis-(4-chloro-phenyl)-2-(2-isopropoxy-phenyl)-4,5-dihydro-1H-imidazole;

2-{2-[4,5-Bis-(4-chloro-phenyl)-4,5-dihydro-1H-imidazol-2-yl]-phenoxy}-acetamide;

4,5-Bis-(4-bromo-phenyl)-2-(2-isopropoxy-phenyl)-4,5-dihydro-1H-imidazole;

{4-[4,5-Bis-(4-chloro-phenyl)-4,5-dihydro-1H-imidazol-2-yl]-phenoxy}-acetic acid ethyl ester;

{2-[4,5-Bis-(4-chloro-phenyl)-4,5-dihydro-1H-imidazol-2-yl]-phenoxy}-acetic acid ethyl ester;

4,5-Bis-(4-bromo-phenyl)-2-(2-ethoxy-phenyl)-4,5-dihydro-1H-imidazole, hydrochloride salt;

4,5-Bis-(4-chloro-phenyl)-2-(3-isopropoxy-phenyl)-4,5-dihydro-1H-imidazole, hydrochloride salt;

4,5-Bis-(4-chloro-phenyl)-2-(3-pyrrolidin-1-yl-phenyl)-4,5-dihydro-1H-imidazole;

Sodium {2-[4,5-bis-(4-chloro-phenyl)-4,5-dihydro-1H-imidazol-2-yl]-phenoxy}-acetate;

Sodium {4-[4,5-bis-(4-chloro-phenyl)-4,5-dihydro-1H-imidazol-2-yl]-phenoxy}-acetate;

Sodium 3-[4,5-bis-(4-chloro-phenyl)-4,5-dihydro-1H-imidazol-2-yl]-benzoate;

4,5-Bis-(4-chloro-phenyl)-2-o-tolyl-4,5-dihydro-1H-imidazole; and

{2-[4,5-Bis-(4-chloro-phenyl)-4,5-dihydro-1H-imidazol-2-yl]-phenyl}-dimethyl-amine.

\* \* \* \* \*

UNITED STATES PATENT AND TRADEMARK OFFICE
CERTIFICATE OF CORRECTION

PATENT NO.     : 6,617,346 B1
DATED          : September 9, 2003
INVENTOR(S)    : Norman Kong et al.

It is certified that error appears in the above-identified patent and that said Letters Patent is hereby corrected as shown below:

Column 71,
Line 49, delete "1H-imidazol-2-yl]-5methoxymethyl-phenyl}-" and insert
-- 1H-imidazol-2-yl]-5-methoxymethyl-phenyl}- --.

Signed and Sealed this

Sixth Day of January, 2004

JAMES E. ROGAN
*Director of the United States Patent and Trademark Office*